(12) United States Patent
Kobayashi et al.

(10) Patent No.: US 7,662,478 B2
(45) Date of Patent: *Feb. 16, 2010

(54) POLYMER AND POLYMER LIGHT-EMITTING DEVICE USING THE SAME

(75) Inventors: Satoshi Kobayashi, Tsukuba (JP); Takanobu Noguchi, Tsukuba (JP); Yoshiaki Tsubata, Tsukuba (JP); Makoto Kitano, Tsukuba (JP); Shuji Doi, Tsukuba (JP); Takahiro Ueoka, Tsukuba (JP); Akiko Nakazono, Tsukuba (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/954,223

(22) Filed: Oct. 1, 2004

(65) Prior Publication Data

US 2005/0042195 A1 Feb. 24, 2005

Related U.S. Application Data

(63) Continuation of application No. 10/309,101, filed on Dec. 4, 2002, now abandoned.

(30) Foreign Application Priority Data

Dec. 7, 2001 (JP) ............................. 2001-373924

(51) Int. Cl.
*B32B 25/20* (2006.01)
(52) U.S. Cl. .................... 428/447; 556/430; 556/81; 549/29; 549/505; 568/21; 568/12
(58) Field of Classification Search ................ 428/447; 556/430, 81; 549/29, 505; 568/21, 12
See application file for complete search history.

(56) References Cited

U.S. PATENT DOCUMENTS

| 5,741,921 | A | 4/1998 | Kreuder et al. |
| 5,807,974 | A | 9/1998 | Kim et al. |
| 5,856,434 | A | 1/1999 | Stern et al. |
| 5,859,211 | A | 1/1999 | Kreuder et al. |
| 5,885,368 | A | 3/1999 | Lupo et al. |
| 5,986,121 | A | 11/1999 | Uchida et al. |
| 6,015,631 | A | 1/2000 | Park |
| 6,329,082 | B1 | 12/2001 | Kreuder et al. |
| 6,696,180 | B2 | 2/2004 | Doi et al. |
| 6,984,459 | B1 | 1/2006 | Noguchi et al. |

FOREIGN PATENT DOCUMENTS

| DD | 249 275 A1 | 9/1987 |
| DE | 249275 A1 | 9/1987 |
| DE | 43 31 401 A1 | 3/1995 |
| DE | 4331401 A1 | 3/1995 |
| DE | 19846767 A1 | 4/2000 |
| EP | 0567835 A1 | 11/1993 |
| EP | 1113017 A1 | 7/2001 |
| EP | 0754691 B1 | 11/2003 |
| JP | 58-021684 | 2/1983 |
| JP | 58-154718 A | 9/1983 |
| JP | 58-56373 B2 | 12/1983 |
| JP | 10-506426 A | 6/1998 |
| JP | 2000-252065 A | 9/2000 |
| JP | 2000-284480 A | 10/2000 |
| JP | 2001-123156 A | 5/2001 |
| JP | 2001-123157 A | 5/2001 |
| JP | 2001-172284 A | 6/2001 |
| JP | 2002-255960 A | 9/2002 |
| KR | 2001-0021172 | 3/2001 |
| WO | 99/54385 A1 | 10/1999 |
| WO | WO 99/54385 A1 | 10/1999 |
| WO | WO 02/26856 A1 | 4/2002 |
| WO | 02/072661 A1 | 9/2002 |

OTHER PUBLICATIONS

Database WPI, Section Ch, Week 200103, Derwent Publications Ltd., London, GB; AN 2001-019116, XP002236253 & JP 2000 252065 A (Sumitomo Chem Co., Ltd.), Sep. 14, 2000.
Chan et al. Macromolecules, 28 (1995), 6410-6415.
H. Sirringhaus; "Dibenzothienobisbenzothiophene - a Novel Fused-Ring Oligomer with High Field-Effect Mobility"; Journal of Materials Chemistry; 1999; vol. 9; pp. 2095-2101.
R. Gerdil et al.; "A Polarographic and Spectrographic Study of Dibenzothiopene and Some of Its Isologs"; Journal of the American Chemical Society; 1966; vol. 88, No. 4; pp. 733-737.

(Continued)

*Primary Examiner*—Kuo-Liang Peng
(74) *Attorney, Agent, or Firm*—Sughrue Mion, PLLC

(57) ABSTRACT

Provided is a polymer comprising a repeating unit represented by formula (1),

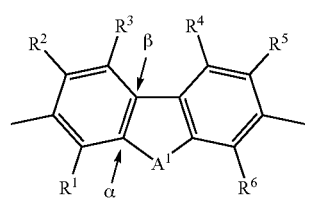

(1)

wherein, $A^1$ represents a divalent group in which the bond distance ratio (bond distance of $C(\alpha)$-$A^1$/bond distance of $C(\alpha)$-$C(\beta)$) is 1.10 or more; $R^1$, $R^2$, $R^3$, $R^4$, $R^5$, and $R^6$, each independently represent a hydrogen atom, alkyl group, alkyloxy group, aryloxy group, arylalkyloxy group, etc. The polymer is useful as a light-emitting material, a charge transporting material, etc.

26 Claims, No Drawings

OTHER PUBLICATIONS

H. Gilman at al.; "Cyclic Organosilicon Compounds: II. Reactions Involving Certain Functional and Related Dibenzosilole Compounds"; Journal of the American Chemical Society; 1958; vol. 80; pp. 3243-3246.

H. Gilman at al.; "Cyclic Organosilicon Compounds: I. Synthesis of Compounds Containing the Dibenzosilole Nucleus": Journal of the American Chemical Society; 1958; vol. 80; pp. 1883-1886.

EP Communication, dated Apr. 28, 2009, issued in corresponding EP Application No. 09004354.8, 5 pages.

POLYMER AND POLYMER LIGHT-EMITTING DEVICE USING THE SAME

This is a continuation of application Ser. No. 10/309,101 filed Dec. 4, 2002, which was abandoned on Jul. 1, 2004 now abandoned.

BACKGROUND OF THE INVENTION

1. Field of the Invention

The present invention relates to a new polymer, a process for producing the same, a polymeric fluorescent substance thereof, and a polymer light-emitting device (hereinafter, may be referred to as "polymer LED") using the same.

2. Description of the Related Art

High molecular weight light-emitting materials and high molecular weight charge transporting materials are variously studied since they are soluble in solvents, unlike low molecular weight materials, and can be formed into light emitting layers or charge transporting layers by coating method. As the example, polyfluorene derivatives are known.

SUMMARY OF THE INVENTION

The object of the present invention is to provide a new polymer which can be used as a light-emitting material, a charge transporting material, etc., a process for producing the same, and a polymer light-emitting device using said polymer.

That is, the present invention relates to a polymer having a polystyrene reduced number average molecular weight of $10^3$-$10^8$, and comprising a repeating unit represented by the below formula (1),

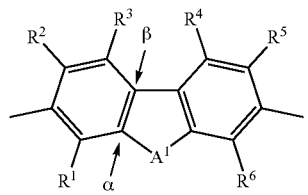

(1)

wherein, $A^1$ is a divalent group represented by -Z- or -Z-Z- in which Z is an atomic group which may have a substituent; $A^1$ represents a divalent group in which the bond distance ratio (bond distance C2-$A^1$/bond distance C2-C1) is 1.10 or more, in which C2 is the carbon of α position, and C1 is the carbon of β position, respectively to $A^1$; $R^1$, $R^2$, $R^3$, $R^4$, $R^5$, and $R^6$, each independently represent a hydrogen atom, a halogen atom, an alkyl group, alkenyl group, alkynyl group, alkyloxy group, alkylthio group, an alkylamino group, aryl group, aryloxy group, arylthio group, arylamino group, arylalkyl group, arylalkyloxy group, aryl alkylthio group, arylalkylamino group, substituted silyl group, acyl group, acyloxy group, imino group, amide group, arylalkenyl group, arylalkynyl group, monovalent heterocyclic group, or cyano group; $R^2$ and $R^3$ may be connected to form a ring; and $R^4$ and $R^5$ may be connected to form a ring.

DETAILED DESCRIPTION OF THE INVENTION

In the above formula, as the atom contained in Z, a hetero atom is preferable, and as the hetero atom, Si, P, S, Ge, Sn, Se and Te are exemplified.

Examples of the atomic group Z having substituent are as follows.

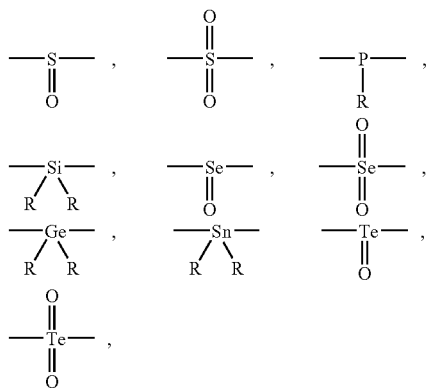

In the formula, R each independently represents a hydrogen atom, a halogen atom, an alkyl group, alkyloxy group, alkylthio group, alkylamino group, aryl group, aryloxy group, arylthio group, arylamino group, arylalkyl group, arylalkyloxy group, arylalkylthio group, arylalkylamino group, substituted silyl group, acyl group, acyloxy group, imino group, amide group, arylalkenyl group, arylalkynyl group, monovalent heterocyclic group, or cyano group.

The bond-distance ratio in the above formula (1) is computable by optimizing the molecular structure of a compound using quantum-chemistry calculation. As the quantum-chemistry calculation method, semi-empirical and non-empirical molecular orbital methods, and a density functional method, etc. can be used. For example, by a density functional method included in quantum-chemistry calculation program Gaussian 98, a structure-optimizing calculation of a compound can be performed using 6-31 g* as a basis function, and b3lyp as a density functional approximation, and the bond-distance ratio can be determined. (Ref: J. Chem. Phys., 98, 5648(1993)).

The bond distance C2-$A^1$ is the distance from C2 to the atom of the group $A^1$ to which C2 is directly bonded. When the repeating unit of formula (1) is asymmetrical, both bond distance ratios are 1.10 or more.

$R^1$, $R^2$, $R^3$, $R^4$, $R^5$ and $R^6$ in the above formula (1) each independently represent a hydrogen atom, a halogen atom, an alkyl group, alkenyl group, alkynyl group, alkyloxy group, alkylthio group, alkylamino group, aryl group, aryloxy group, arylthio group, arylamino group, arylalkyl group, arylalkyloxy group, arylalkylthio group, arylalkylamino group, substituted silyl group, acyl group, acyloxy group, imino group, amide group, arylalkenyl group, arylalkynyl group, monovalent heterocyclic group, or cyano group. $R^2$ and $R^3$ may be connected to form a ring; and $R^4$ and $R^5$ may be connected to form a ring.

Preferably, $R^2$ and $R^5$ are each independently alkyloxy group, alkylthio group, alkylamino group, aryloxy group, arylthio group, arylamino group, arylalkyloxy group, arylalkylthio group, or arylalkylamino group among them, and more preferably, alkyloxy group, aryloxy group, or arylalkyloxy group.

As the halogen atom, exemplified are fluorine, chlorine, bromine, and iodine.

The alkyl group may be any of linear, branched or cyclic, and usually has about 1 to 20 carbon atoms, and the group may have a substituent. Specifically, exemplified are: a methyl group, ethyl group, propyl group, i-propyl group, butyl, i-butyl, t-butyl, pentyl group, hexyl group, cyclohexyl group, heptyl group, octyl group, 2-ethyl hexyl group, nonyl group, decyl group, 3,7-dimethyloctyl group, lauryl group, trifluoromethyl group, pentafluoroethyl group, perfluorobutyl, perfluoro hexyl group, perfluorooctyl group, etc.; and preferably pentyl group, hexyl group, octyl group, 2-ethylhexyl group, decyl group, and 3,7-dimethyloctyl group.

The alkenyl group may be any of linear, branched or cyclic, and usually has about 2 to 20 carbon atoms, and the group may have a substituent. Specifically, exemplified are: ethenyl group, propenyl group, 2-propenyl group, 1-methyl propenyl group, 2-methylpropenyl group, 1,2-dimethyl propenyl group, butenyl group, 2-methylbutenyl group, 1,3-butadienyl group, pentenyl group, hexenyl group, cyclohexenyl group, heptenyl group, octenyl group, 2-ethyl hexenyl group, trifluoroethenyl group, perfluorobutenyl group, perfluorohexenyl group, perfluorooctenyl group, etc.

The alkynyl group may be any of linear, branched or cyclic, and usually has about 2 to 20 carbon atoms, and the group may have a substituent. Specifically, exemplified are: ethynyl group, propynyl group, 2-propynyl group, 2-methyl propynyl group, butynyl group, 2-methylbutynyl group, 1,3-butanediyl group, pentynyl group, hexynyl group, cyclohexynyl group, heptynyl group, octynyl group, 2-ethyl hexynyl group, fluoroethynyl group, perfluorobutynyl group, perfluorohexynyl group, perfluorooctynyl group, etc.

The alkyloxy group may be any of linear, branched or cyclic, and usually has about 1 to 20 carbon atoms, and the group may have a substituent. Specifically, exemplified are: methoxy group, ethoxy group, propyloxy group, i-propyloxy group, butoxy group, i-butoxy group, t-butoxy group, pentyloxy group, hexyloxy group, cyclohexyloxy group, heptyloxy group, octyloxy group, 2-ethylhexyloxy group, nonyloxy group, decyloxy group, 3,7-dimethyloctyloxy group, lauryloxy group, trifluoromethoxy group, pentafluoroethoxy group, perfluorobutoxy group, perfluorohexyl group, perfluorooctyl group, methoxymethyloxy group, 2-methoxyethyloxy group, etc.; and preferably pentyloxy group, hexyloxy group, octyloxy group, 2-ethylhexyloxy group, decyloxy group, and 3,7-dimethyloctyloxy group.

The alkylthio group may be any of linear, branched or cyclic, and usually has about 1 to 20 carbon atoms, and the group may have a substituent. Specifically, exemplified are: methylthio group, ethylthio group, propylthio group, and i-propylthio group, butylthio group, i-butylthio group, t-butylthio group, pentylthio group, hexylthio group, cyclo hexylthio group, heptylthio group, octylthio group, 2-ethyl hexylthio group, nonylthio group, decylthio group, 3,7-dimethyloctylthio group, laurylthio group, trifluoro methylthio group, etc.; and preferably pentylthio group, hexylthio group, octylthio group, 2-ethylhexylthio group, decylthio group, and 3,7-dimethyloctylthio group.

The alkylthio group may be any of linear, branched or cyclic, and usually has about 1 to 40 carbon atoms, and the group may be monoalkylamino group or dialkylamino group. Specifically, exemplified are: methylamino group, dimethyl amino group, ethylamino group, diethylamino group, propyl amino group, dipropylamino group, i-propylamino group, diisopropyl amino group, butylamino group, i-butylamino group, t-butylamino group, pentylamino group, hexylamino group, cyclohexylamino group, heptylamino group, octyl amino group, 2-ethylhexylamino group, nonylamino group, decylamino group, 3,7-dimethyloctylamino group, laurylamino group, cyclopentylamino group, dicyclopentylamino group, cyclohexylamino group, dicyclohexylamino group, pyrrolidyl group, piperidyl group, ditrifluoromethylamino group, etc.; and preferably pentylamino group, hexylamino group, octyl amino group, 2-ethylhexylamino group, decylamino group, and 3,7-dimethyloctylamino group.

The aryl group may have a substituent, and usually has about 6 to 60 carbon atoms. Specifically, exemplified are: phenyl group, $C_1$-$C_{12}$ alkoxyphenyl group ($C_1$-$C_{12}$ shows 1-12 carbon atoms), $C_1$-$C_{12}$ alkylphenyl group, 1-naphthyl group, 2-naphthyl group, pentafluorophenyl group, etc., and preferably $C_1$-$C_{12}$ alkoxyphenyl group, and $C_1$-$C_{12}$ alkylphenyl group.

The aryloxy group may have a substituent on the aromatic ring, and usually has about 6 to 60 carbon atoms. Specifically, exemplified are: phenoxy group, $C_1$-$C_{12}$ alkoxyphenoxy group, $C_1$-$C_{12}$ alkylphenoxy group, 1-naphtyloxy group, 2-naphtyloxy group, pentafluorophenyloxy group, pyridyloxy group, pyridazinyloxy group, pyrimidyloxy group, pyrazyloxy group, triazinyloxy group, etc.; and preferably $C_1$-$C_{12}$ alkoxyphenoxy group, and $C_1$-$C_{12}$ alkyl phenoxy group.

The arylthio group may have a substituent on the aromatic ring, and usually has about 6 to 60 carbon atoms. Specifically, exemplified are: phenylthio group, $C_1$-$C_{12}$ alkoxyphenylthio group, $C_1$-$C_{12}$ alkylphenylthio group, 1-naphthylthio group, 2-naphthylthio group, pentafluoro phenylthio group, pyridylthio group, pyridazinylthio group, pyrimidylthio group, pyrazylthio group, triazinylthio group etc.; and preferably $C_1$-$C_{12}$ alkoxyphenylthio group, and $C_1$-$C_{12}$ alkylphenylthio.

The arylamino group may have a substituent on the aromatic ring, and usually has about 6 to 60 carbon atoms. Specifically, exemplified are: phenylamino group, diphenyl amino group, $C_1$-$C_{12}$ alkoxyphenylamino group, di($C_1$-$C_{12}$ alkoxyphenyl)amino group, di($C_1$-$C_{12}$ alkylphenyl)amino group, 1-naphtylamino group, 2-naphtylamino group, pentafluorophenylamino group, pyridylamino group, pyridazinylamino group, pyrimidylamino group, pyrazylamino group, triazinylamino group etc.; and preferably $C_1$-$C_{12}$ alkylphenylamino group, and di($C_1$-$C_{12}$ alkylphenyl)amino group.

The arylalkyl group may have a substituent, and usually has about 7 to 60 carbon atoms. Specifically, exemplified are: phenyl-$C_1$-$C_{12}$ alkyl group, $C_1$-$C_{12}$ alkoxyphenyl-$C_1$-$C_{12}$ alkyl group, $C_1$-$C_{12}$ alkylphenyl-$C_1$-$C_{12}$ alkyl group, 1-naphtyl-$C_1$-$C_{12}$ alkyl group, 2-naphtyl-$C_1$-$C_{12}$ alkyl group, etc., and preferably $C_1$-$C_{12}$ alkoxyphenyl-$C_1$-$C_{12}$ alkyl group, and $C_1$-$C_{12}$ alkylphenyl-$C_1$-$C_{12}$ alkyl group.

The arylalkyloxy group may have a substituent, and usually has about 7 to 60 carbon atoms. Specifically, exemplified are: phenyl-$C_1$-$C_{12}$ alkyloxy group, $C_1$-$C_{12}$ alkyloxy phenyl-$C_1$-$C_{12}$ alkyloxy group, $C_1$-$C_{12}$ alkylphenyl-$C_1$-$C_{12}$ alkyloxy group, 1-naphtyl-$C_1$-$C_{12}$ alkyloxy group, 2-naphtyl-$C_1$-$C_{12}$ alkyloxy group, etc.; and preferably $C_1$-$C_{12}$ alkyloxy phenyl-$C_1$-$C_{12}$ alkyloxy group, and $C_1$-$C_{12}$ alkylphenyl-$C_1$-$C_{12}$ alkyloxy group.

The arylalkylthio group may have a substituent, and usually has about 7 to 60 carbon atoms. Specifically, exemplified are: phenyl-$C_1$-$C_{12}$ alkylthio group, $C_1$-$C_{12}$ alkyloxy phenyl-$C_1$-$C_{12}$ alkylthio group, $C_1$-$C_{12}$ alkylphenyl-$C_1$-$C_{12}$ alkylthio group, 1-naphtyl-$C_1$-$C_{12}$ alkylthio group, 2-naphtyl-$C_1$-$C_{12}$ alkylthio group, etc.; and preferably $C_1$-$C_{12}$ alkyloxy phenyl-$C_1$-$C_{12}$ alkylthio group, and $C_1$-$C_{12}$ alkylphenyl-$C_1$-$C_{12}$ alkylthio group.

The arylalkylamino group usually has about 7 to 60 carbon atoms. Specifically, exemplified are: phenyl-$C_1$-$C_{12}$ alkyl amino group, $C_1$-$C_{12}$ alkoxyphenyl-$C_1$-$C_{12}$ alkylamino group, $C_1$-$C_{12}$ alkylphenyl-$C_1$-$C_{12}$ alkylamino group, di($C_1$-$C_{12}$ alkoxy phenyl-$C_1$-$C_{12}$ alkyl)amino group, di($C_1$-$C_{12}$ alkylphenyl-$C_1$-$C_{12}$ alkyl)amino group, 1-naphtyl-$C_1$-$C_{12}$ alkylamino group, 2-naphtyl-$C_1$-$C_{12}$ alkylamino group, etc.; and preferably $C_1$-$C_{12}$ alkylphenyl-$C_1$-$C_{12}$ alkylamino group, and di($C_1$-$C_{12}$ alkylphenyl-$C_1$-$C_{12}$ alkyl)amino group.

As the substituted silyl group, specifically exemplified are: trialkylsilyl groups, such as trimethylsilyl group, triethylsilyl group, tripropylsilyl group, tri-i-propylsilyl group, dimethyl-i-propylsilyl group, diethyl-i-propylsilyl group, t-butyldimethylsilyl group, pentyldimethylsilyl group, hexyldimethylsilyl group, heptyldimethyl silyl group, octyldimethylsilyl group, 2-ethylhexyldimethylsilyl group, nonyldimethylsilyl group, decyldimethylsilyl group, 3,7-dimethyloctyl-dimethylsilyl group, and lauryldimethylsilyl group, and the like; triarylsilyl groups, such as triphenyl silyl group, tri-p-xylylsilyl group, and the like; tri(arylalkyl)silyl groups, such as tribenzylsilyl group, and the like; (alkyl)(aryl)silyl groups, such as diphenylmethylsilyl group, t-butyl diphenylsilyl group, dimethylphenylsilyl group, and the like; mono(arylalkyl)silyl groups, such as phenyl-$C_1$-$C_{12}$ alkylsilyl group, $C_1$-$C_{12}$ alkyloxyphenyl-$C_1$-$C_{12}$ alkylsilyl group, $C_1$-$C_{12}$ alkylphenyl-$C_1$-$C_{12}$ alkylsilyl group, 1-naphtyl-$C_1$-$C_{12}$ alkylsilyl group, 2-naphtyl-$C_1$-$C_{12}$ alkylsilyl group, and the like; and mono(arylalkyl)dialkylsilyl groups, such as phenyl-$C_1$-$C_{12}$ alkyldimethyl silyl group, and the like.

Pentyldimethylsilyl group, hexyldimethylsilyl group, octyldimethylsilyl group, 2-ethylhexyl-dimethylsilyl group, decyldimethylsilyl group, 3,7-dimethyloctyldimethylsilyl group, $C_1$-$C_{12}$ alkyloxyphenyl-$C_1$-$C_{12}$ alkylsilyl group, $C_1$-$C_{12}$ alkylphenyl-$C_1$-$C_{12}$ alkylsilyl group are preferable.

The acyl group has usually 2 to 20 carbon atoms, and specifically exemplified are acetyl group, propionyl group, butyryl group, isobutyryl group, pivaloyl group, benzoyl group, trifluoroacetyl group, pentafluorobenzoyl group, etc.

The acyloxy group usually has 2 to 20 carbon atoms, and specifically exemplified are acetyloxy group, propionyloxy group, butyryloxy group, isobutyryloxy group, pivaloyloxy group, benzoyloxy group, trifluoroacetyloxy group, pentafluorobenzoyloxy group, etc.

The imino group usually has about 2 to 20 carbon atoms. Specifically, groups represented by following structural formulas etc. are exemplified.

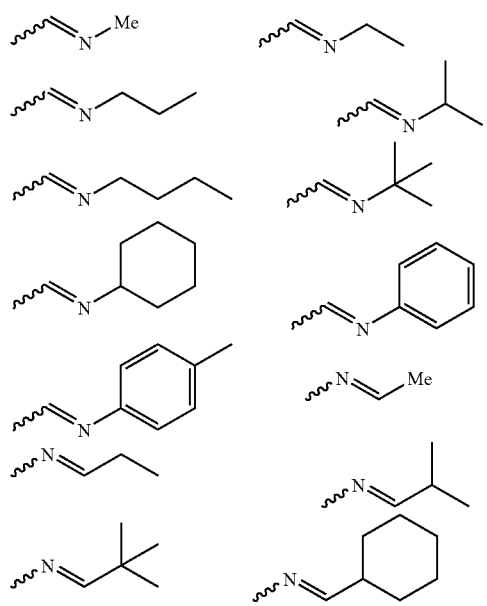

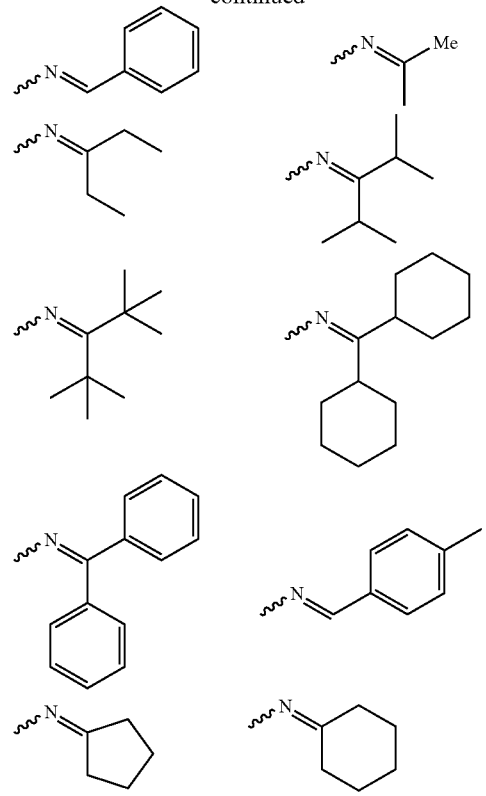

The amide group usually has 2 to 20 carbon atoms, and specifically exemplified are formamide group, acetamide group, propioamide group, butyroamide group, benzamide group, trifluoroacetamide group, pentafluorobenzamide group, diformamide group, diacetoamide group, dipropioamide group, dibutyroamide group, dibenzamide group, ditrifluoro acetamide group, dipentafluorobenzamide group, succinimide group, phthalic-imide group, etc.

The arylalkenyl group usually has 7 to 60 carbon atoms, and specifically exemplified are phenyl-$C_2$-$C_{12}$ alkenyl group, $C_1$-$C_{12}$ alkyloxyphenyl-$C_2$-$C_{12}$ alkenyl group, $C_1$-$C_{12}$ alkyl phenyl-$C_2$-$C_{12}$ alkenyl group, 1-naphtyl-$C_2$-$C_{12}$ alkenyl group, 2-naphtyl-$C_2$-$C_{12}$ alkenyl group, etc.; and preferably $C_1$-$C_{12}$ alkyloxy phenyl-$C_2$-$C_{12}$ alkenyl group, and $C_1$-$C_{12}$ alkyl phenyl-$C_2$-$C_{12}$ alkenyl group.

The arylalkynyl group usually has 7 to 60 carbon atoms, and specifically exemplified are phenyl-$C_2$-$C_{12}$ alkynyl group, $C_1$-$C_{12}$ alkyloxyphenyl-$C_2$-$C_{12}$ alkynyl group, $C_1$-$C_{12}$ alkyl phenyl-$C_2$-$C_{12}$ alkynyl group, 1-naphtyl-$C_2$-$C_{12}$ alkynyl group, 2-naphtyl-$C_2$-$C_{12}$ alkynyl group, etc.; and preferably $C_1$-$C_{12}$ alkyloxyphenyl-$C_2$-$C_{12}$ alkynyl group, and $C_1$-$C_{12}$ alkylphenyl-$C_2$-$C_{12}$ alkynyl group.

The monovalent heterocyclic group means an atomic group in which a hydrogen atom is removed from a heterocyclic compound, and usually has about 4 to 60 carbon atoms. Specifically, exemplified are: thienyl group, $C_1$-$C_{12}$ alkyl thienyl group pyroryl group, furyl group, pyridyl group, $C_1$-$C_{12}$ alkylpyridyl group, etc.; and preferably thienyl group, $C_1$-$C_{12}$ alkylthienyl group, pyridyl group, and $C_1$-$C_{12}$ alkylpyridyl group.

Among them, $A^1$ in the above formula (1) is preferably a divalent group represented by the below formula (4), (5), or (6).

(4)

[in the formula, $R^7$ represents an alkyl group, alkyloxy group, alkylthio group, alkylamino group, aryl group, aryloxy group, arylthio group, arylamino group, arylalkyl group, arylalkyloxy group, arylalkylthio group, arylalkylamino group, acyl group, acyloxy group, amide group, or monovalent heterocyclic group.]

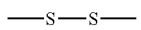
(5)

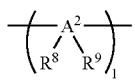
(6)

[in the formula, $A^2$ represents Si, Ge, or Sn. $R^8$ and $R^9$ each independently represent alkyl group, alkyloxy group, alkylthio group, alkylamino group, aryl group, aryloxy group, arylthio group, arylamino group, arylalkyl group, arylalkyloxy group, arylalkylthio group, arylalkylamino group, acyloxy group, amide group, or monovalent heterocyclic group. l represents 1 or 2.]

Among them, in the above formula (1), preferables are: a polymer whose $A^1$ is a divalent group represented by the above formula (4); a polymer whose $A^1$ is a divalent group represented by the above formula (5); a polymer whose $A^1$ is a divalent group represented by formula (6), $A^2$ is Si, and l is 1; and a polymer whose $A^1$ is a divalent group represented by formula (6), $A^2$ is Si, and l is 2.

Specific examples of the divalent group whose $A^1$ is represented by the above formula (4) include followings.

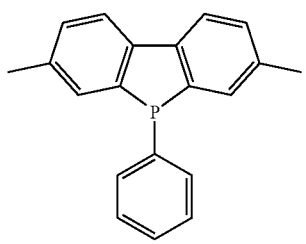

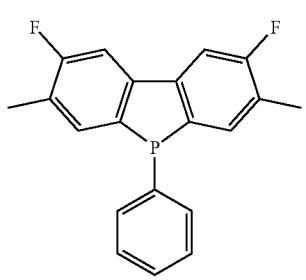

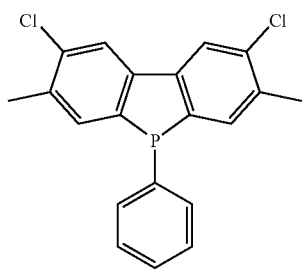

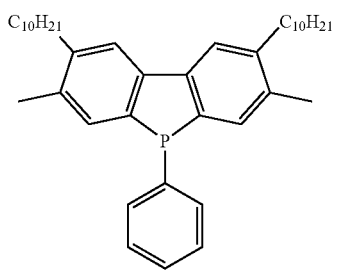

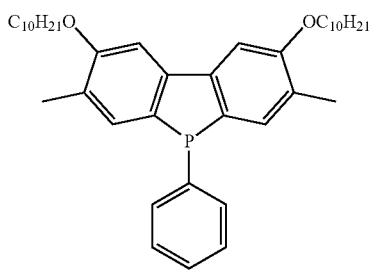

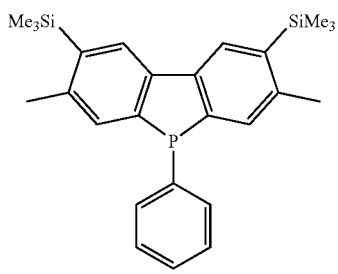

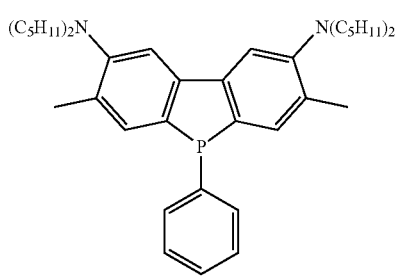

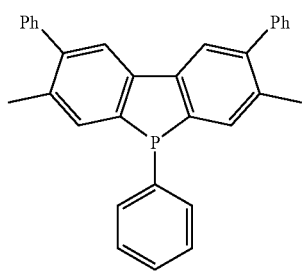

-continued
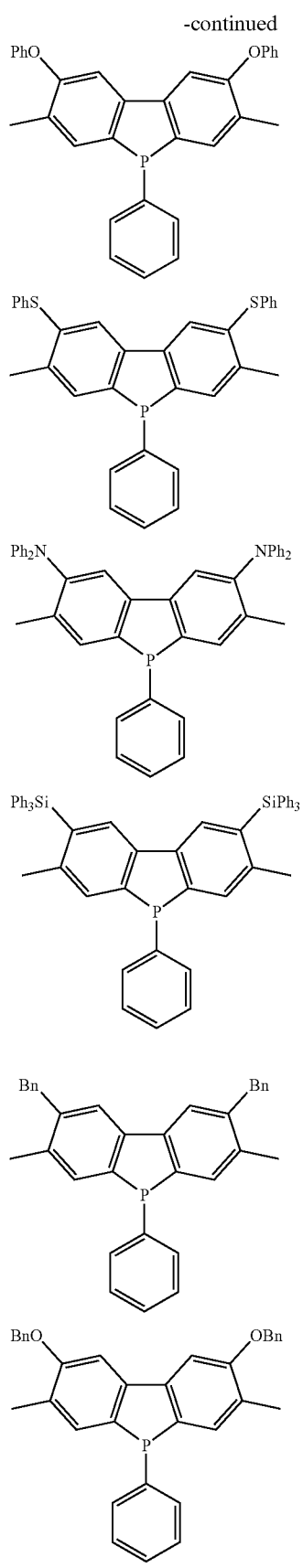
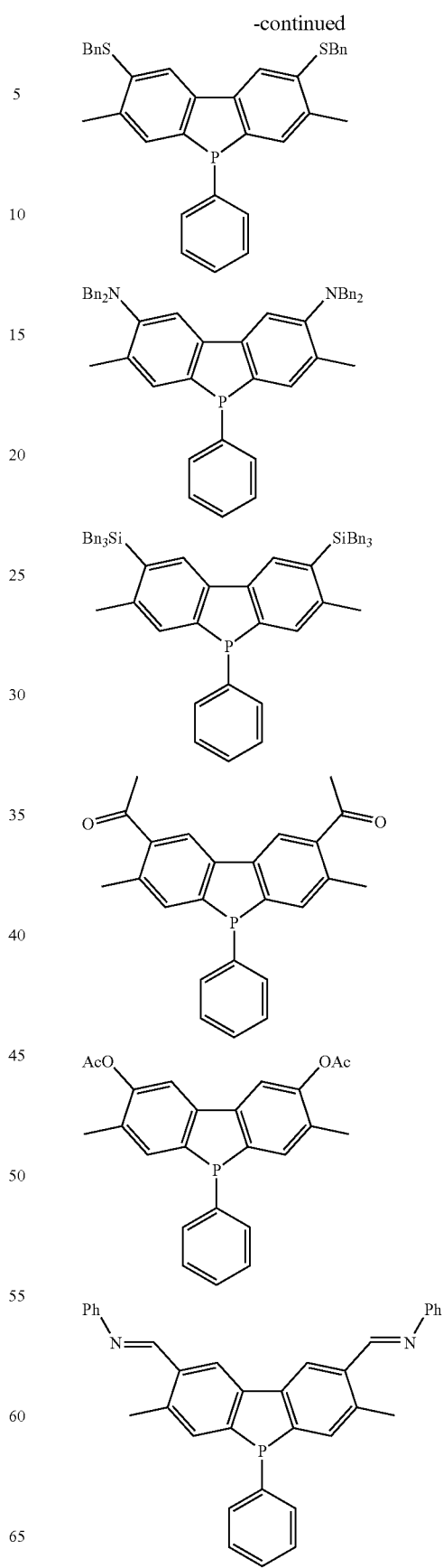

-continued
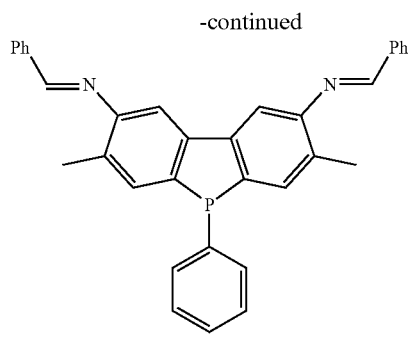
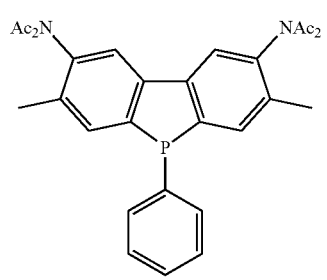
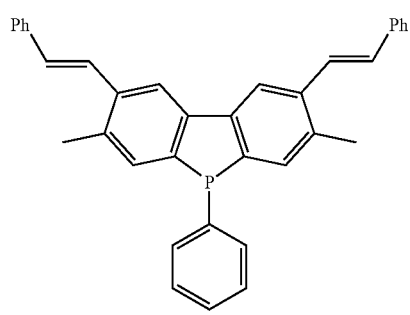
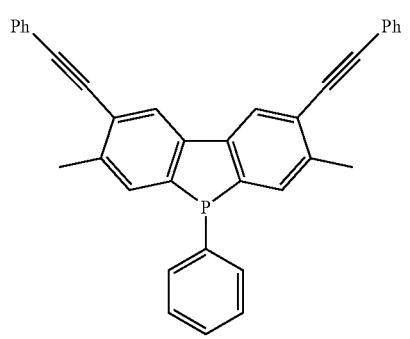
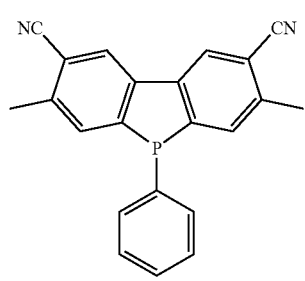
-continued
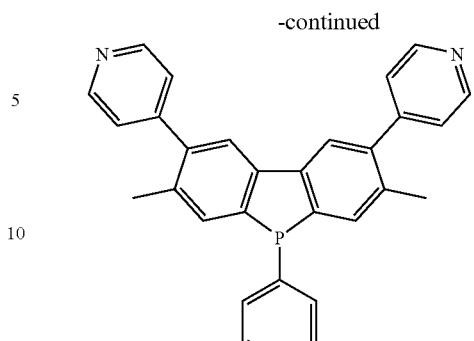
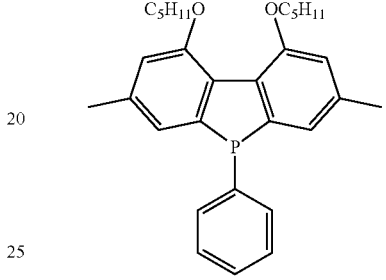
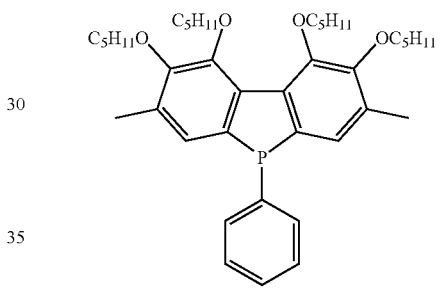
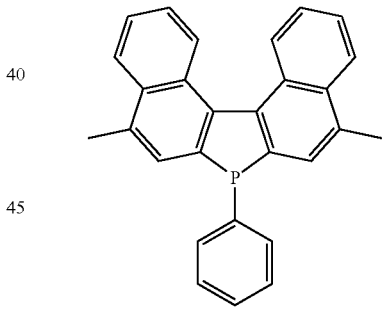
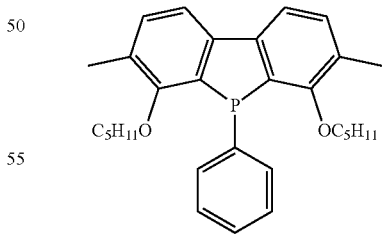
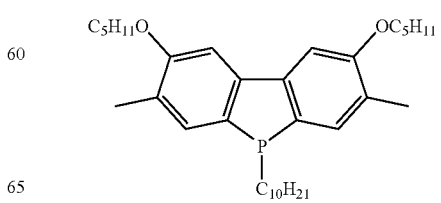

-continued
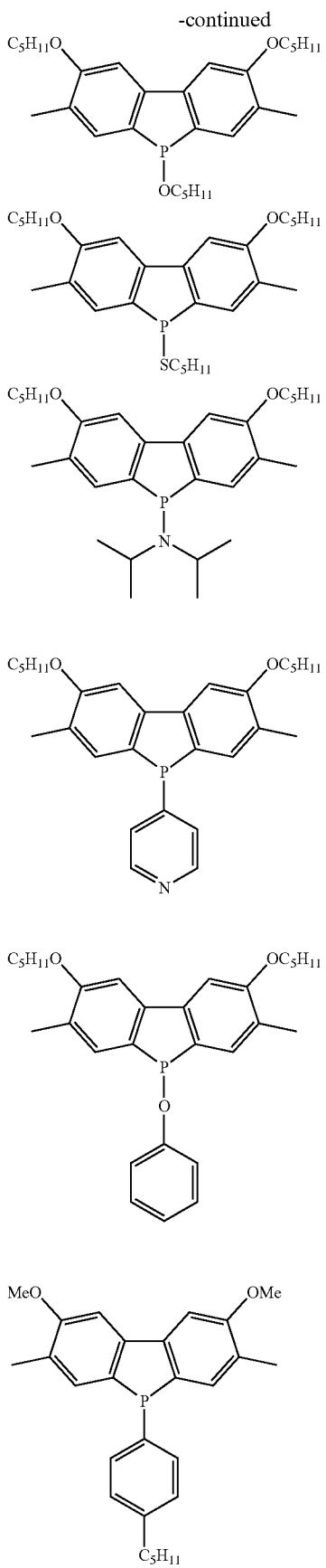
-continued
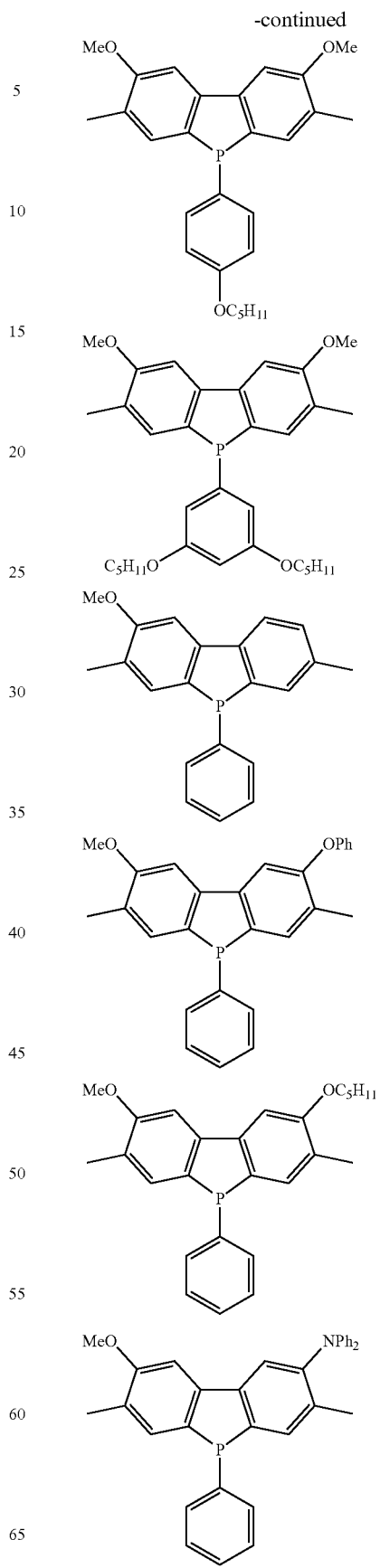

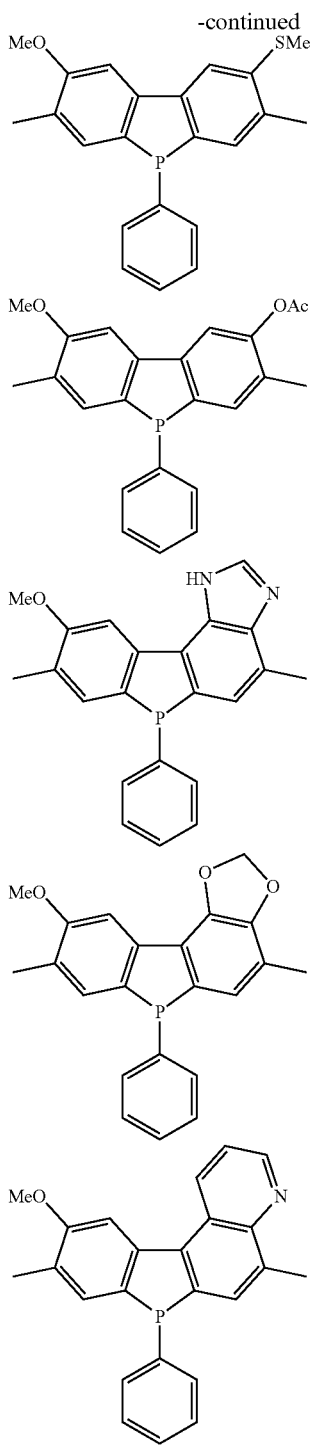
Specific examples of the divalent group whose $A^1$ is represented by the above formula (5) include followings.
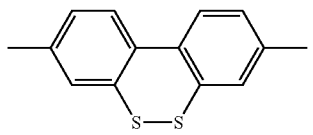
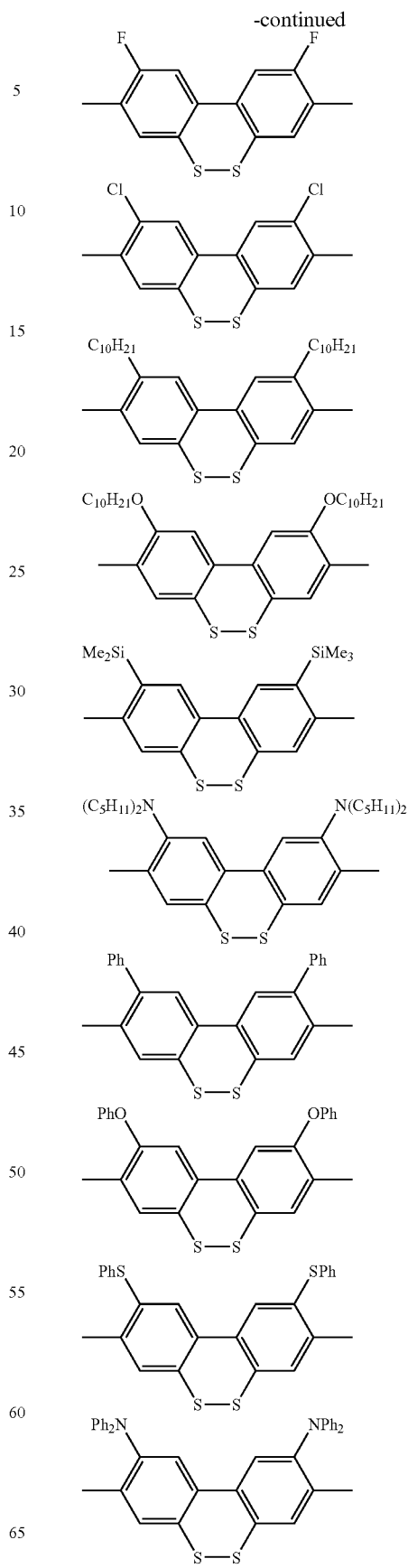

-continued
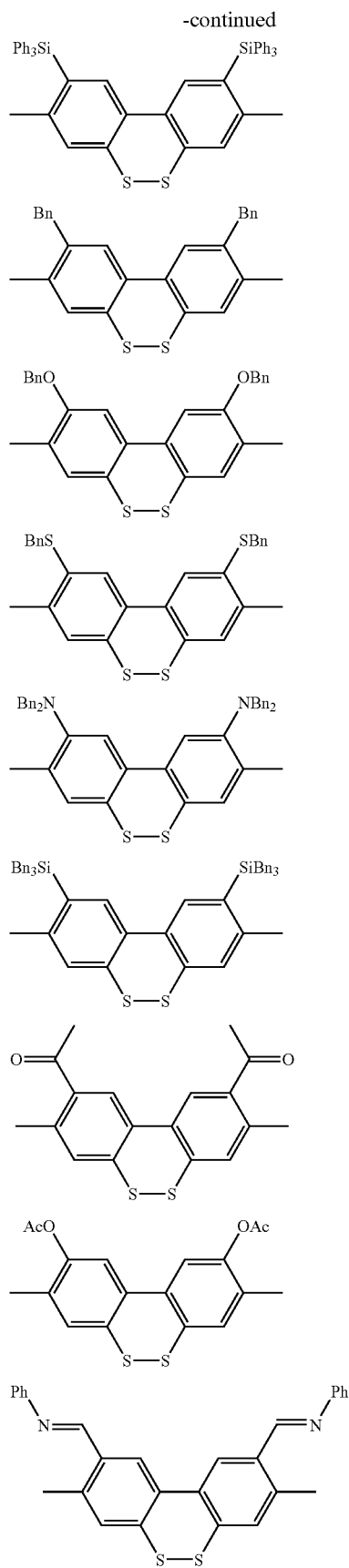
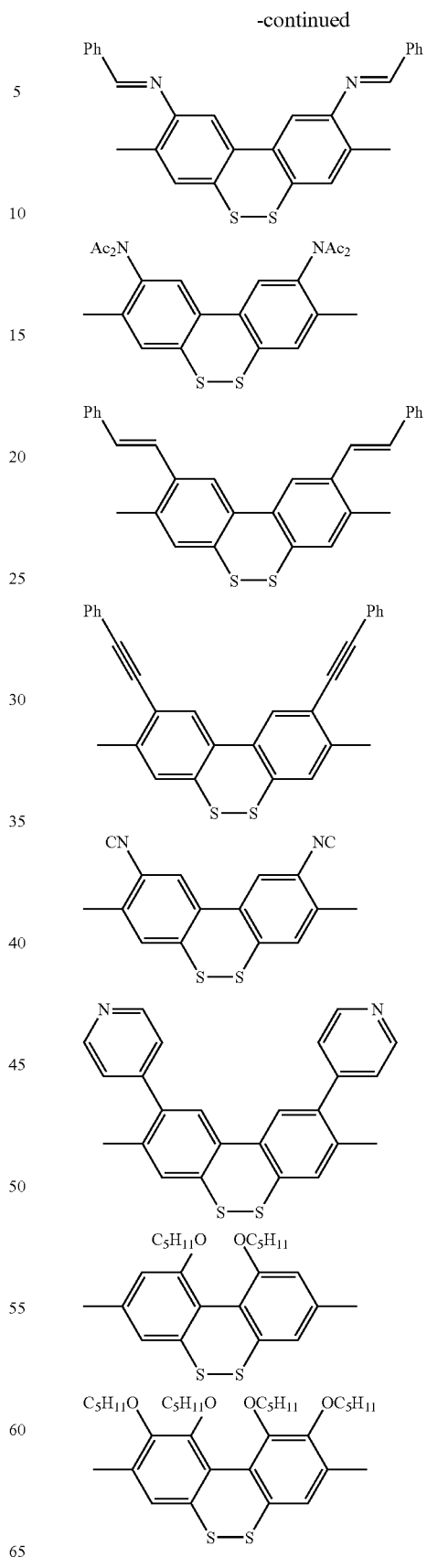

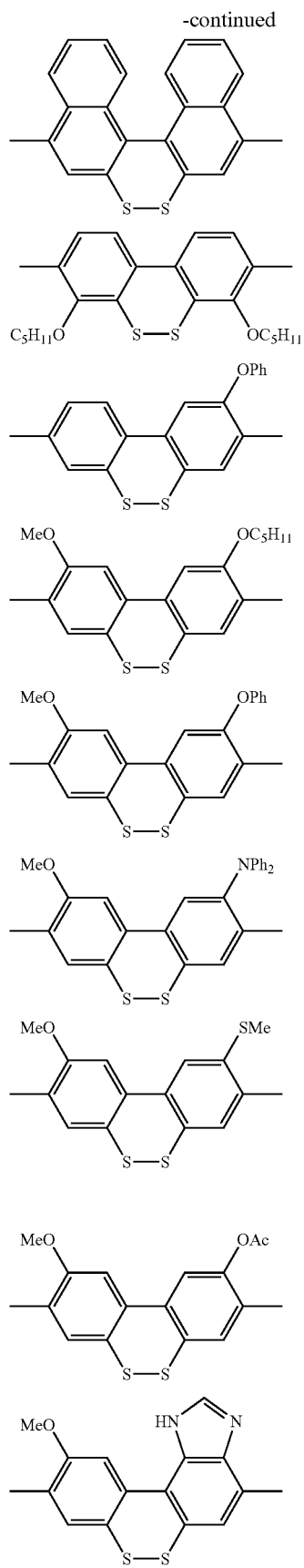
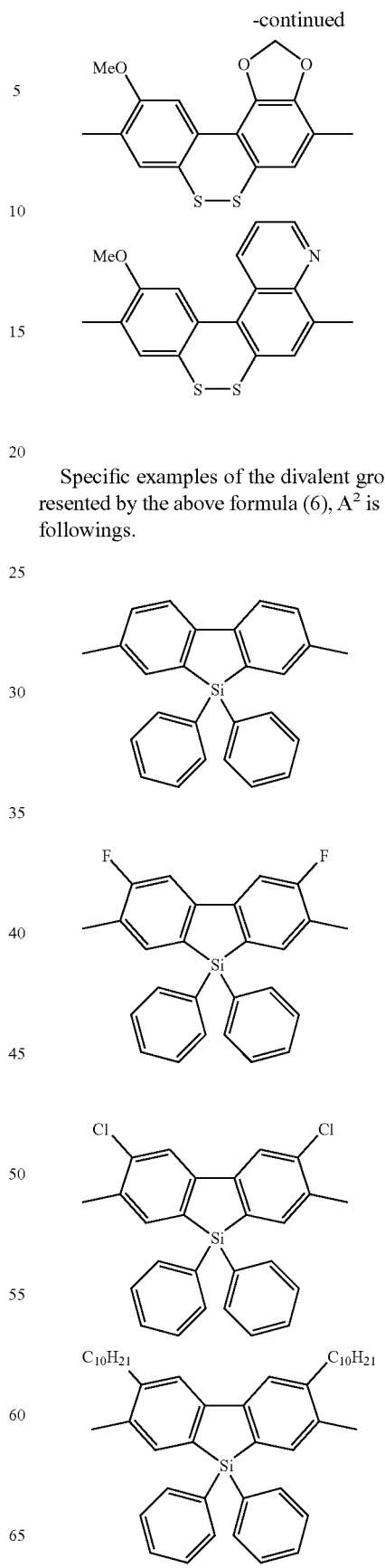
Specific examples of the divalent group whose $A^1$ is represented by the above formula (6), $A^2$ is Si, and l is 1 include followings.

-continued
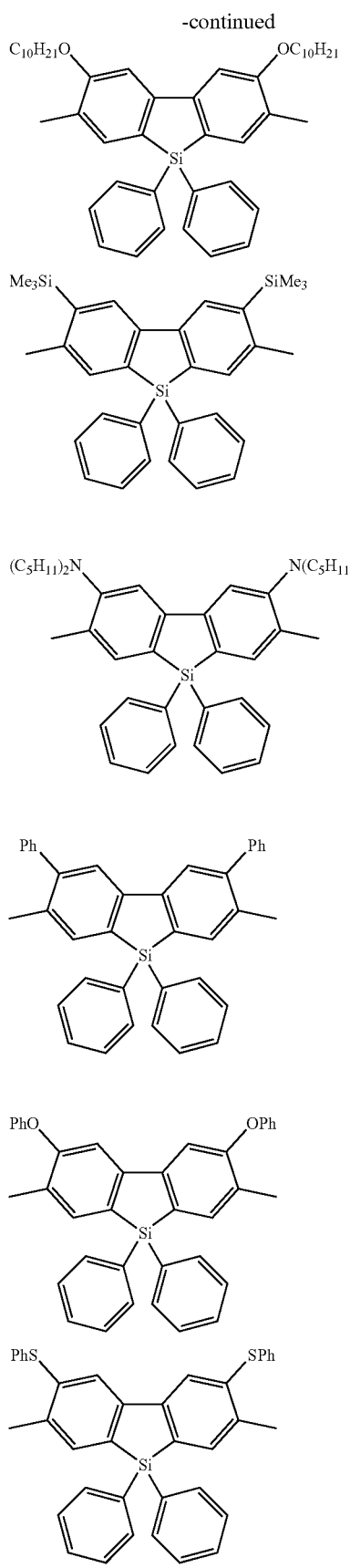
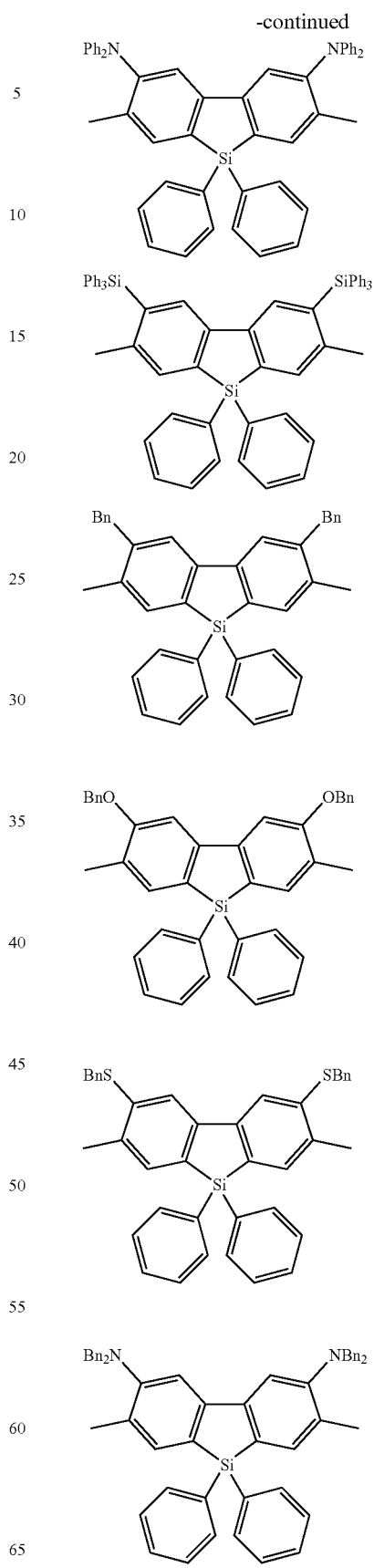

-continued
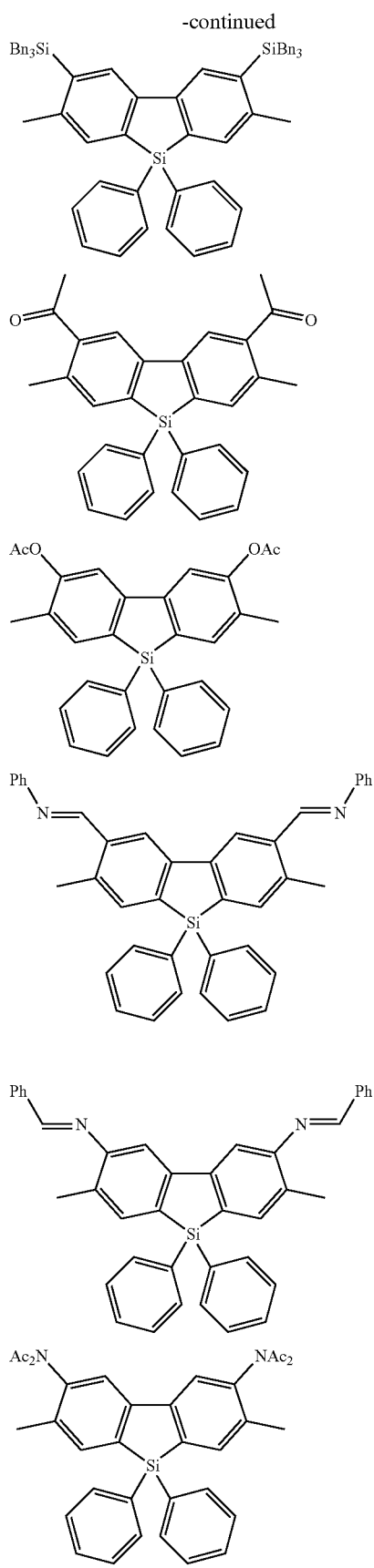
-continued
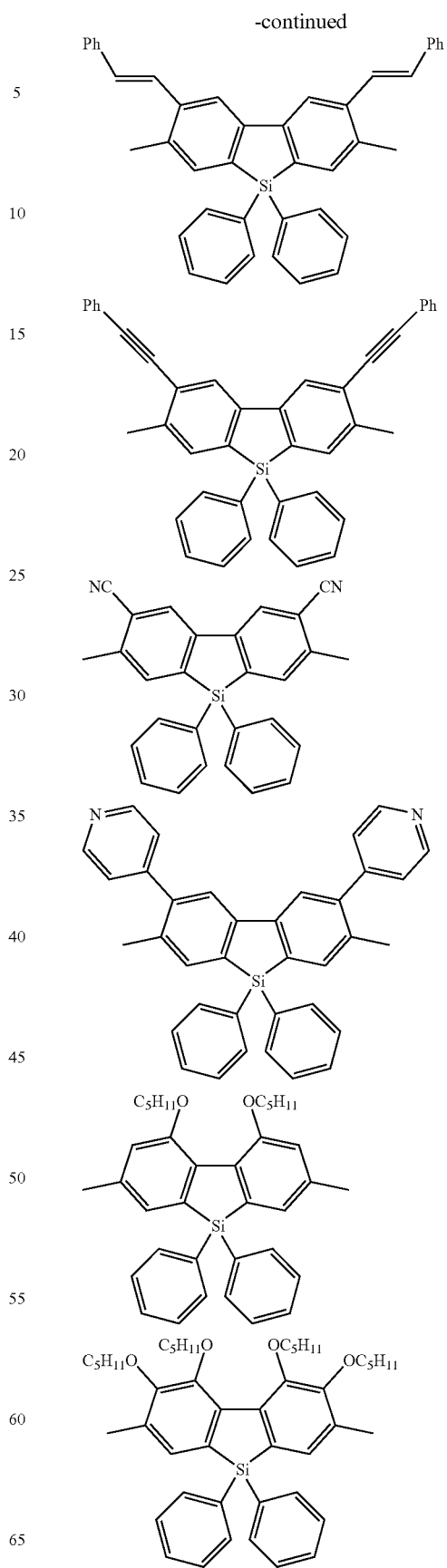

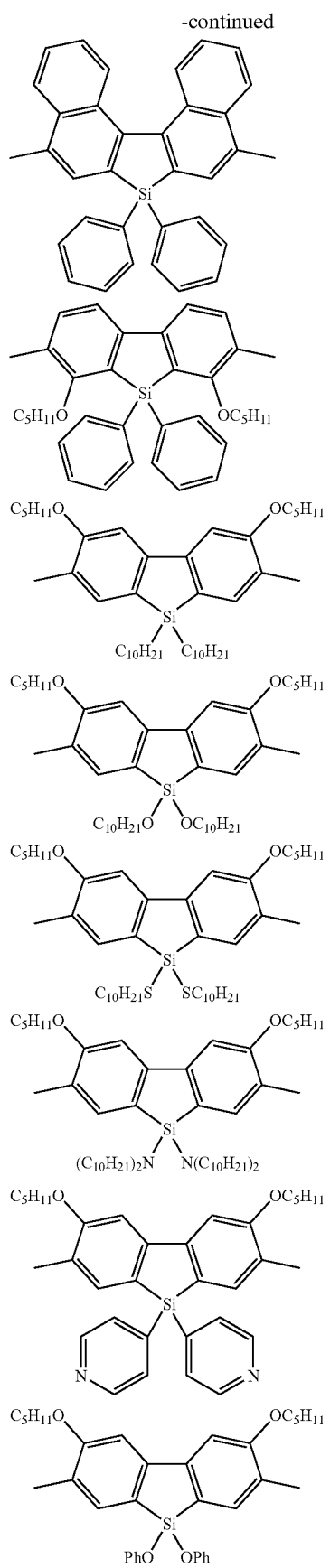
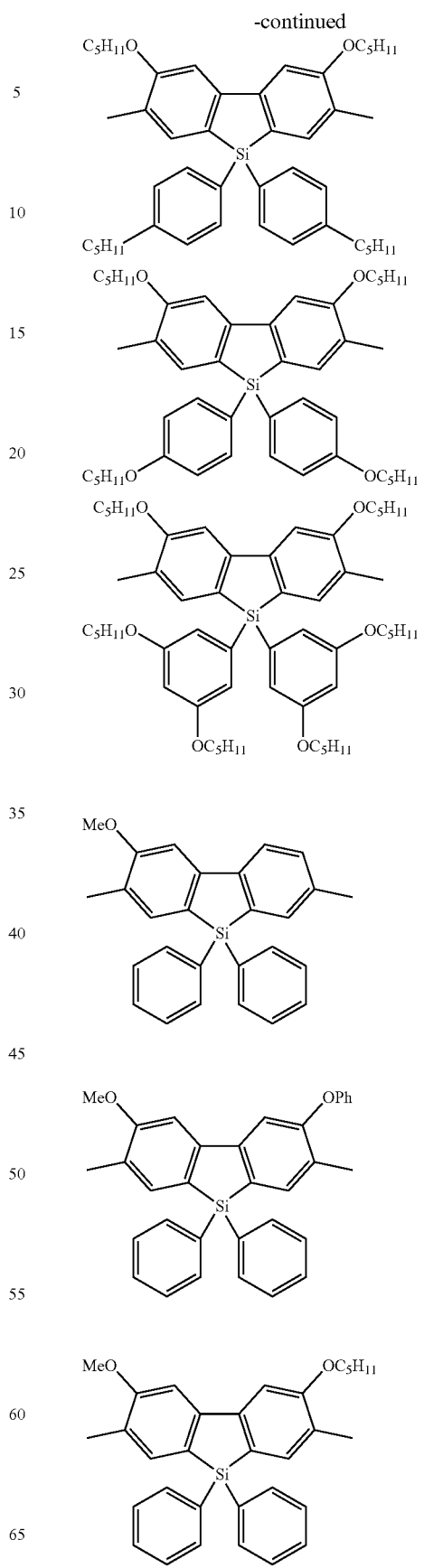

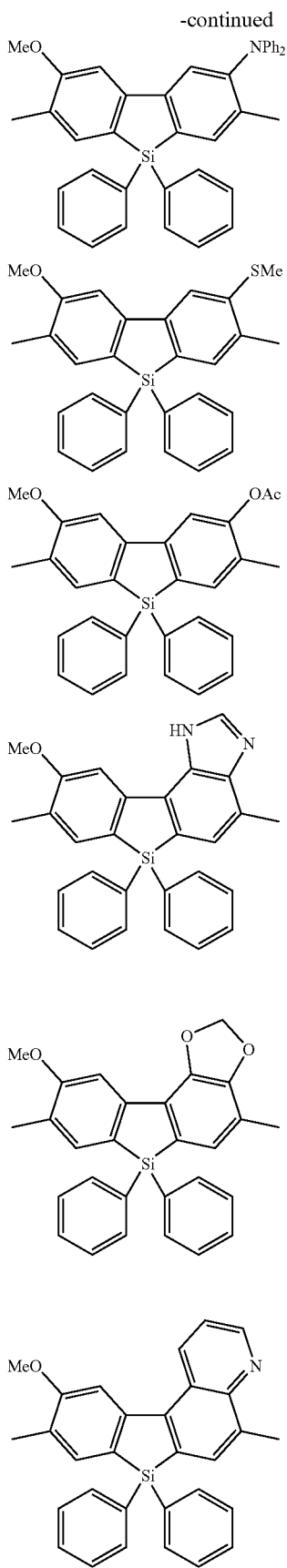
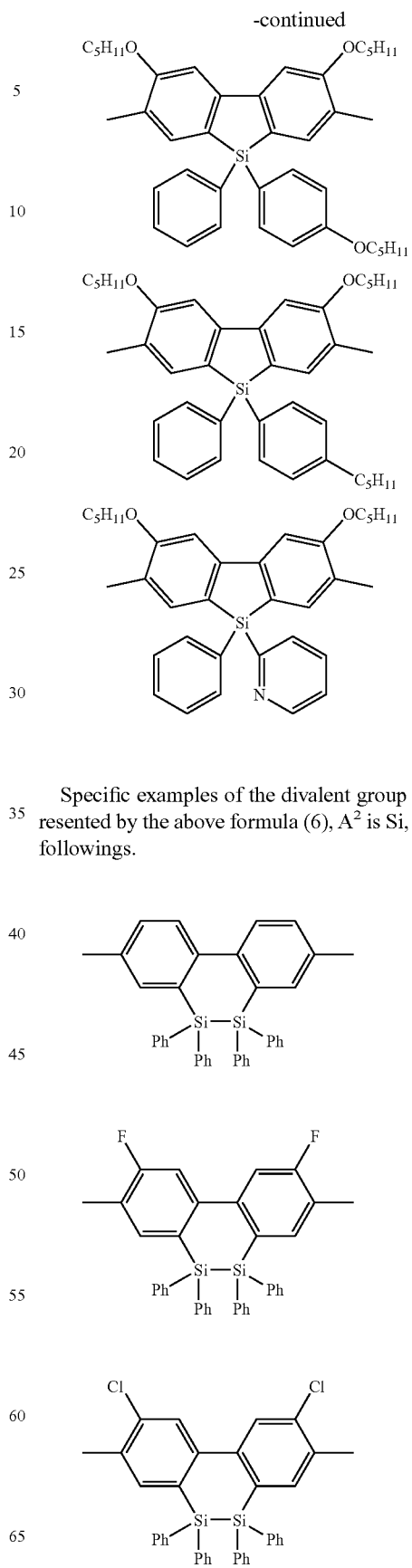
Specific examples of the divalent group whose $A^1$ is represented by the above formula (6), $A^2$ is Si, and l is 2 include followings.

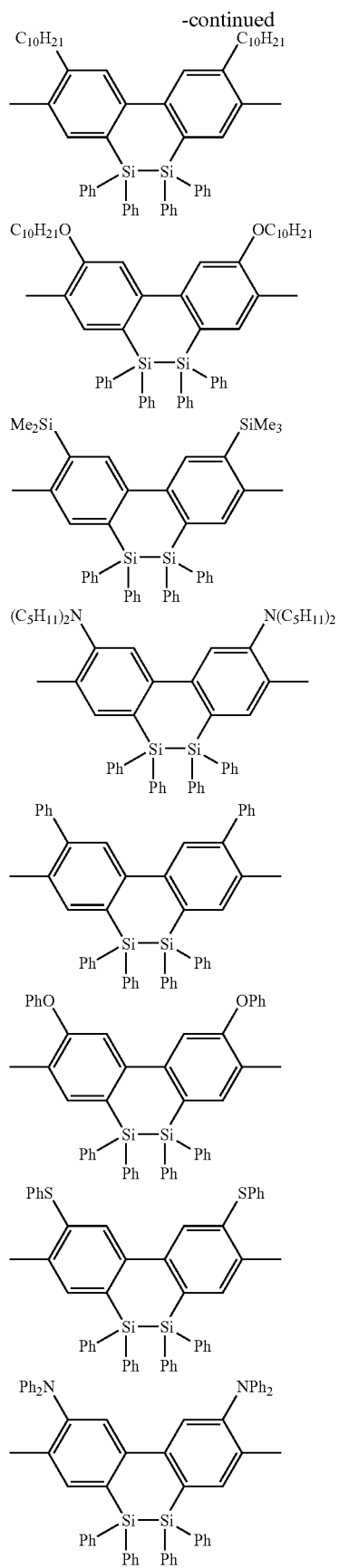
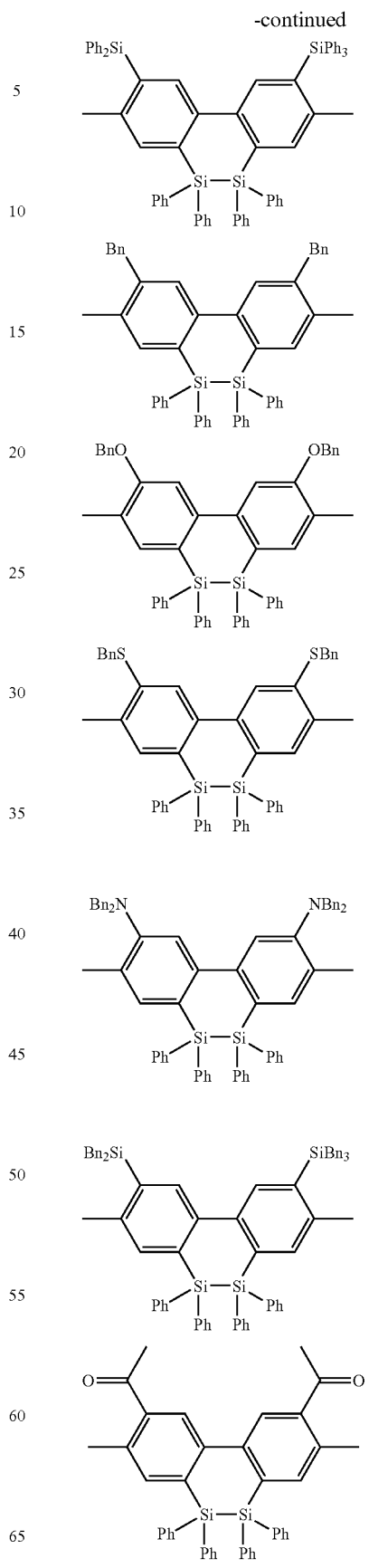

-continued
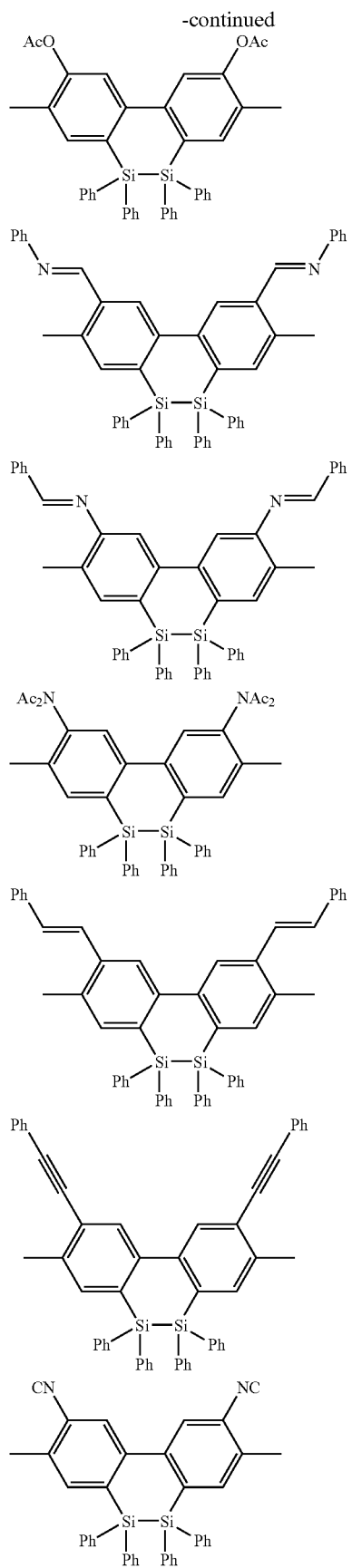
-continued
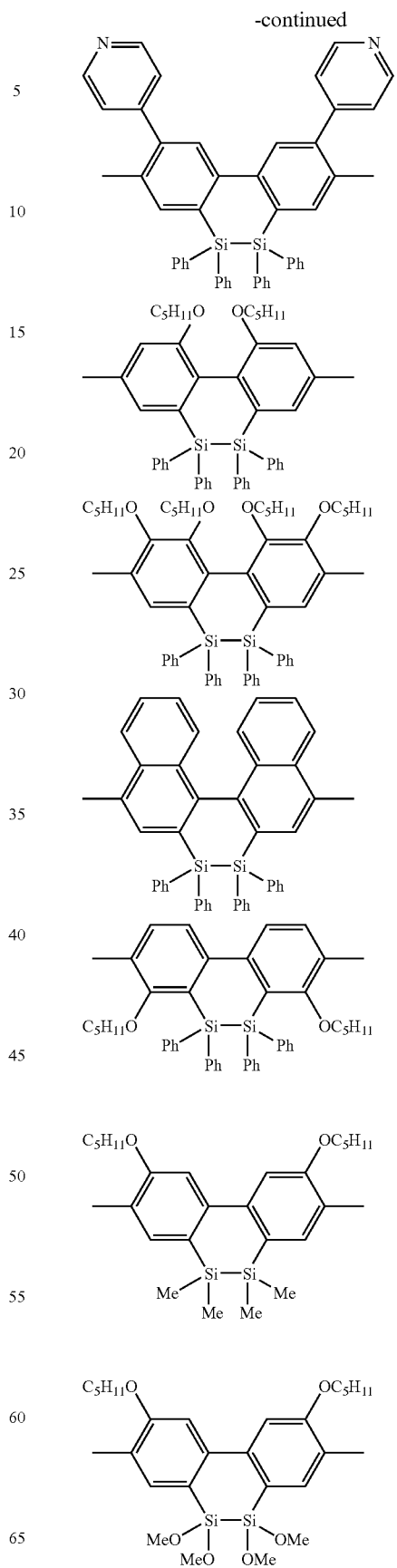

-continued
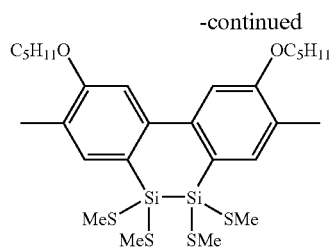
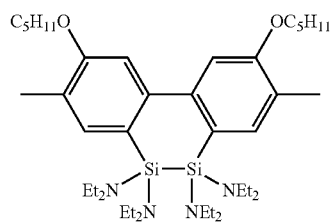
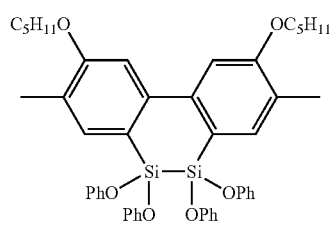
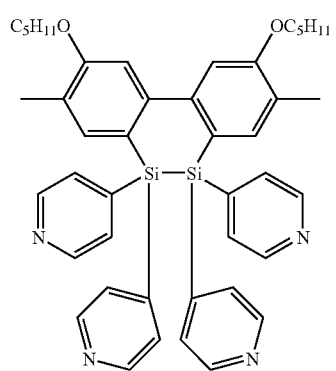
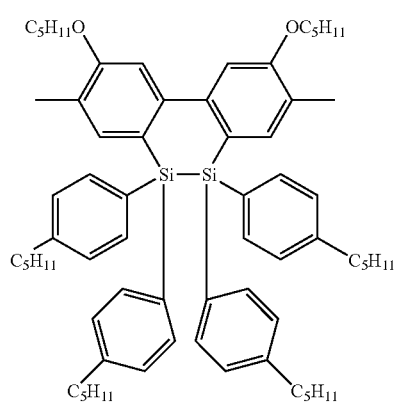
-continued
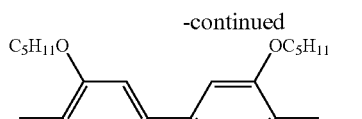
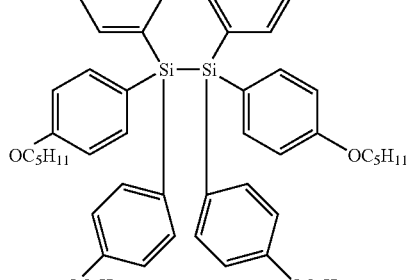
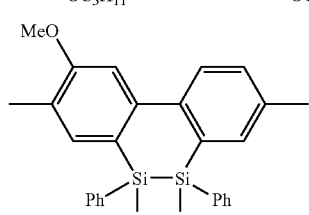
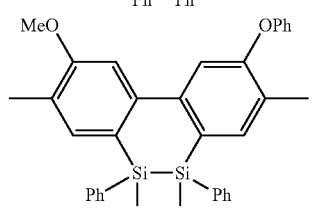
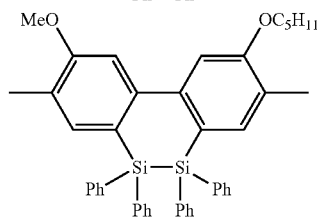
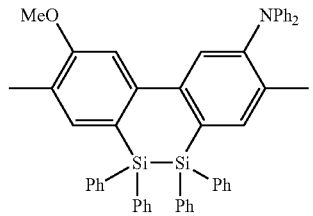
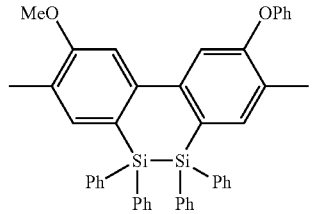
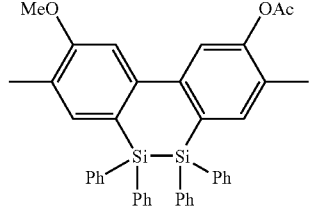

-continued

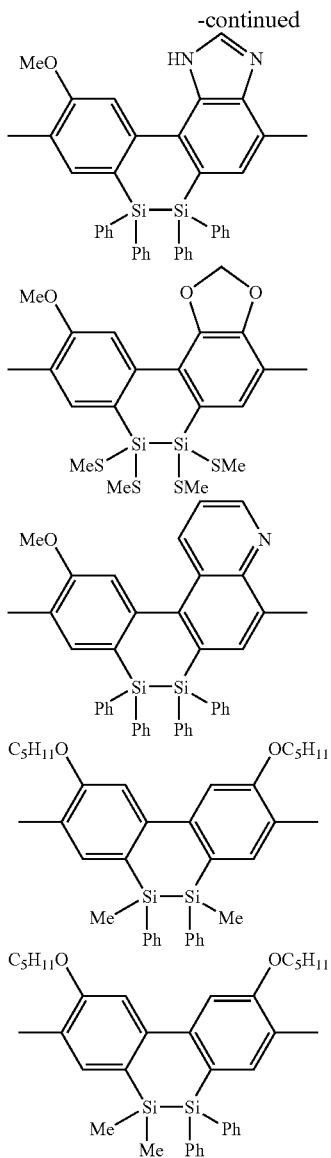

In the above formula, Me represents a methyl group, Ph represents a phenyl group, Bn represents a benzyl, and Ac represents an acetyl group.

The polymer of the present invention may contain two or more kinds of repeating units represented by the above formula (1).

The amount of the repeating unit shown by the above formula (1) is usually 1 to 100% by mole based on the sum of total moles of all repeating units contained in the polymer of the present invention, preferably 40 to 90% by mole, and more preferably 70 to 85% by mole.

The polymer of the present invention may contain a repeating unit other than the repeating unit represented by the above formula (1). As the repeating unit other than formula (1), exemplified are a repeating unit represented by the below formula (7), and a repeating unit represented by formula (8)after-mentioned.

(7)

[in the formula, $Ar^6$ represents an arylene group or a divalent heterocyclic group, $R^{17}$ and $R^{18}$ each independently represent a hydrogen atom, an alkyl group, aryl group, monovalent heterocyclic group, or cyano group; and n represents 0 or 1.]

In view of the life time of a device, the repeating unit represented by the after-mentioned formula (8) is preferable.

The $Ar^6$ may have a substituent, such as an alkyl group, alkyloxy group, alkylthio group, alkylamino group, aryl group, aryloxy group, arylthio group, arylamino group, arylalkyl group, arylalkyloxy group, arylalkylthio group, arylalkylamino group, substituted silyl group, acyl group, acyloxy group, imino group, amide group, imide group, arylalkenyl group, arylalkynyl group, monovalent heterocyclic group, or cyano group. Specific examples of these substituents represent the same as aforementioned. When $Ar^6$ has a plurality of substituents, they may be mutually the same or different.

The arylene group in the present invention includes those containing a benzene ring, a condensed ring, and two or more of independent benzene rings or condensed rings bonded through a group such as a direct bond, a vinylene group or the like. The arylene group has usually 6 to 60 carbon atoms, preferably 6 to 20 carbon atoms. As the arylene group, exemplified are phenylene group (for example, following formula (26)), naphthalenediyl group (following formula (27)), anthracenylene group (following formula (28)), biphenylene group (following formula (29)), triphenylene group (following formula (30)), condensed ring compound group (following formula (31)), etc.

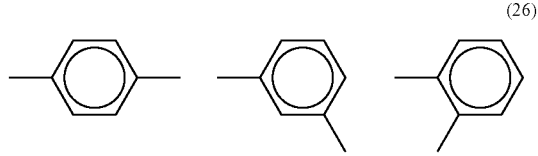

(26)

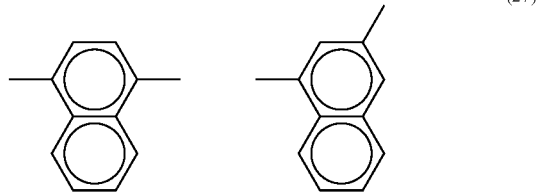

(27)

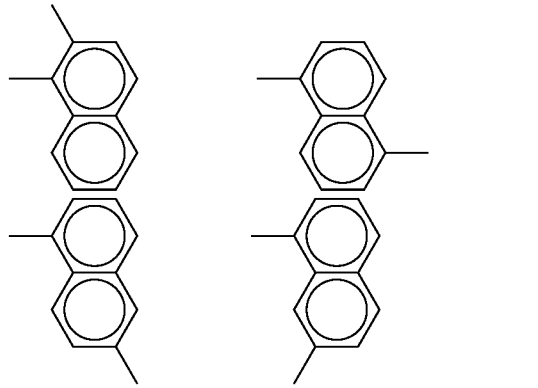

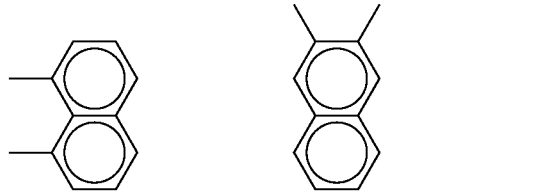

-continued
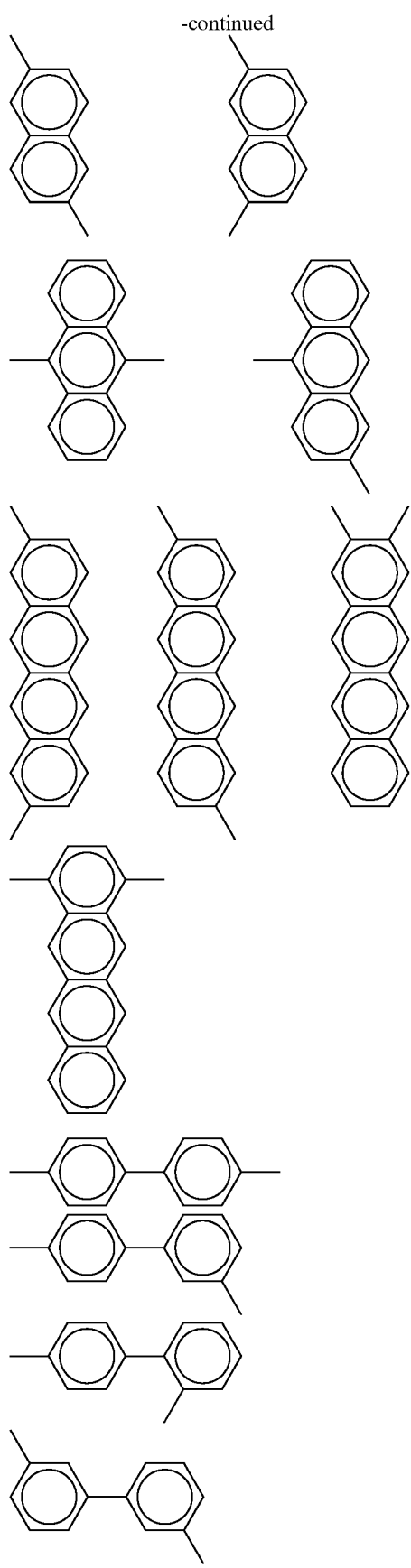
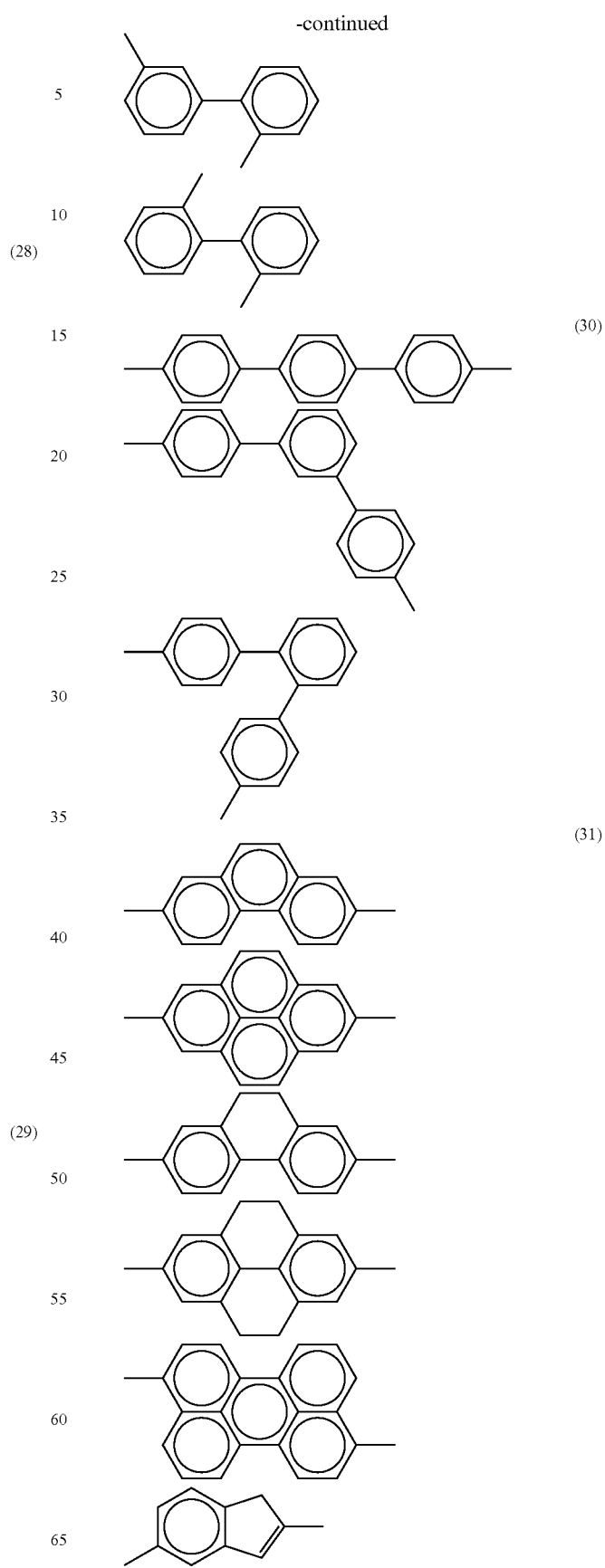

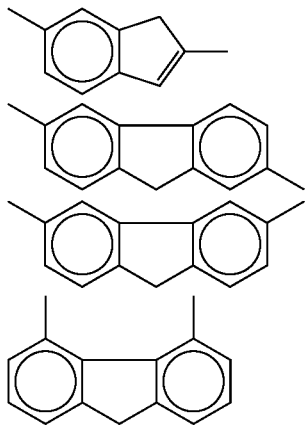

In the present invention, the divalent heterocyclic group is an atomic group in which two hydrogen atoms are removed from a heterocyclic compound, and usually has 4 to 60 carbon atoms, preferably 4 to 20 carbon atoms. They may have a substituent on the hetero-ring and the carbon atoms of the substituent are not counted as the carbon atoms of the heterocyclic group.

The heterocyclic compound means an organic compound having a cyclic structure in which at least one heteroatom such as oxygen, sulfur, nitrogen, phosphorus, boron, etc. is contained in the cyclic structure as the element other than carbon atoms.

As the divalent heterocyclic compound group, followings are exemplified.

Divalent heterocyclic compound group containing a nitrogen as a hetero atom; pyridine-diyl group (following formula (32)), diaza phenylene group (following formula (33)), quinolinediyl group (following formula (34)), quinoxaline diyl group (following formula (35)), acridine diyl group (following formula (36)), bipyridyl diyl group (following formula (37)), phenanthroline diyl group (following formula (38)), etc.; groups containing a hetero atom, such as silicon, nitrogen, sulfur, selenium, etc. and having a fluorene structure (following formula (39));

5 membered-ring heterocyclic compound group containing a hetero atom such as silicon, nitrogen, sulfur, selenium, etc. (following formula (40));

5 membered-ring condensation heterocyclic compound group containing a hetero atom such as silicon, nitrogen, sulfur, selenium, etc. (following formula (41)), benzothiadiazole-4,7-diyl group, benzo-oxadiazole-4,7-diyl group, etc.;

group in which 5 membered ring heterocyclic compound group containing silicon, nitrogen, sulfur, selenium, etc. as a hetero atom is connected with a phenyl group at the α position of the hetero atom to form a dimer or oligomer (following formula (42)); and group in which 5 membered ring heterocyclic compound group containing silicon, nitrogen, sulfur, selenium, etc. as a hetero atom is connected with a phenyl group at the α position of the hetero atom (following formula (43)).

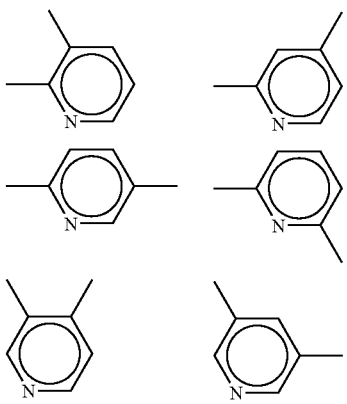

(32)

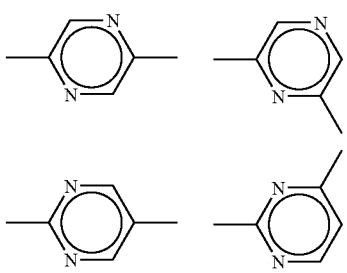

(33)

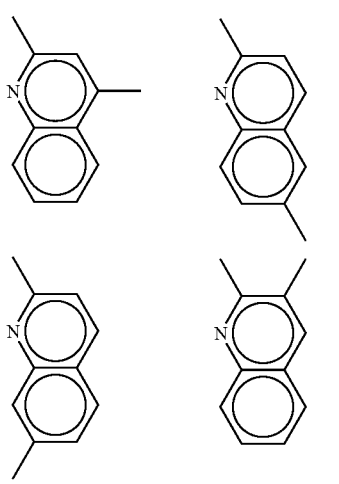

(34)

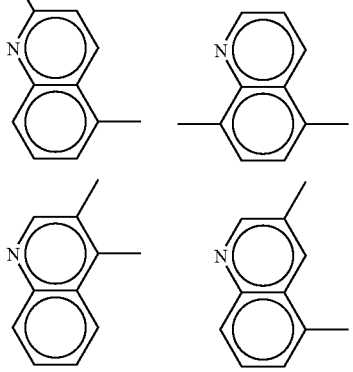

-continued
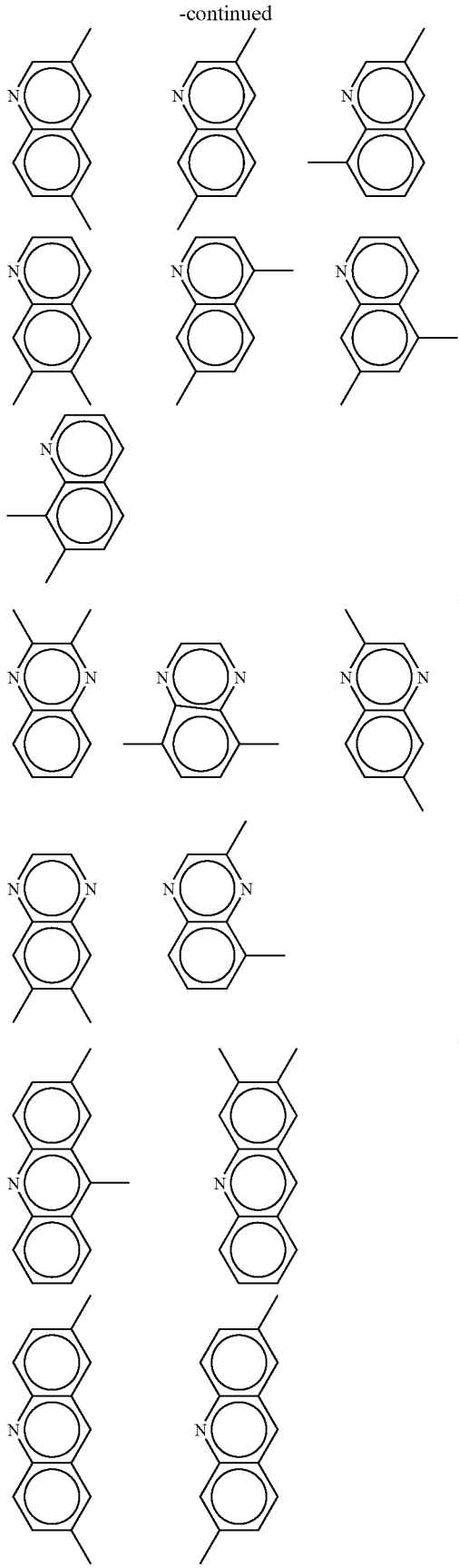
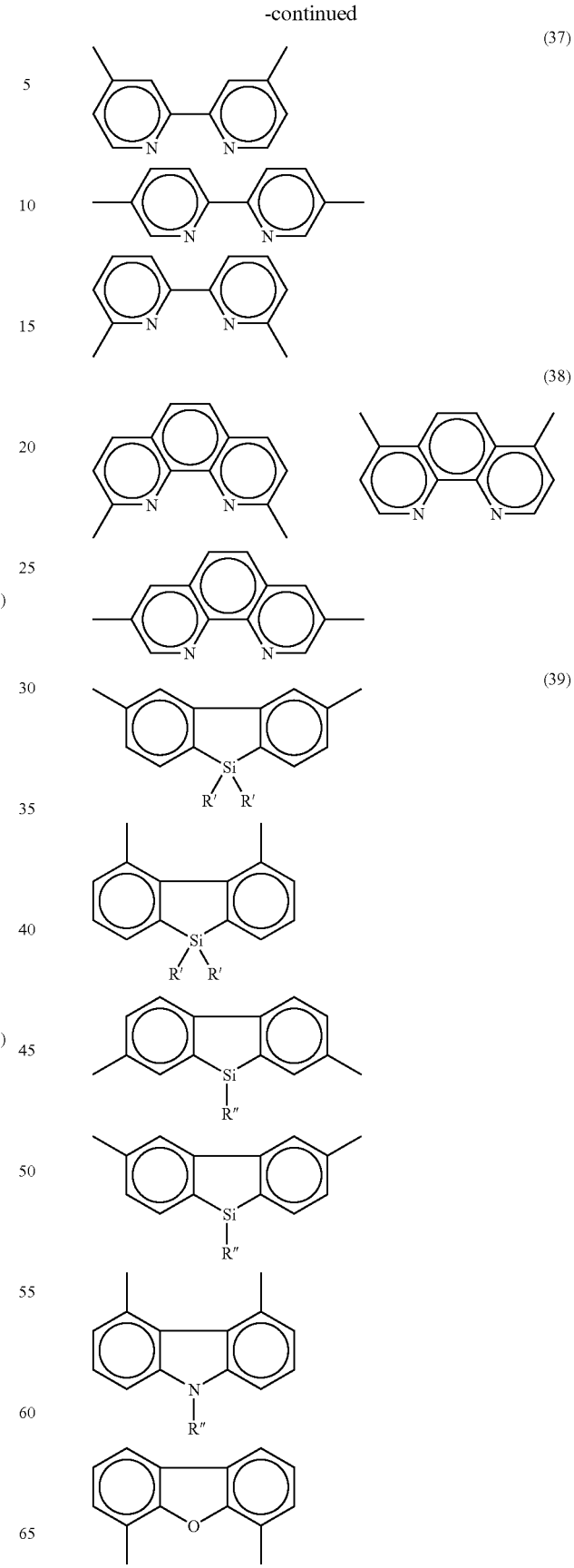

-continued

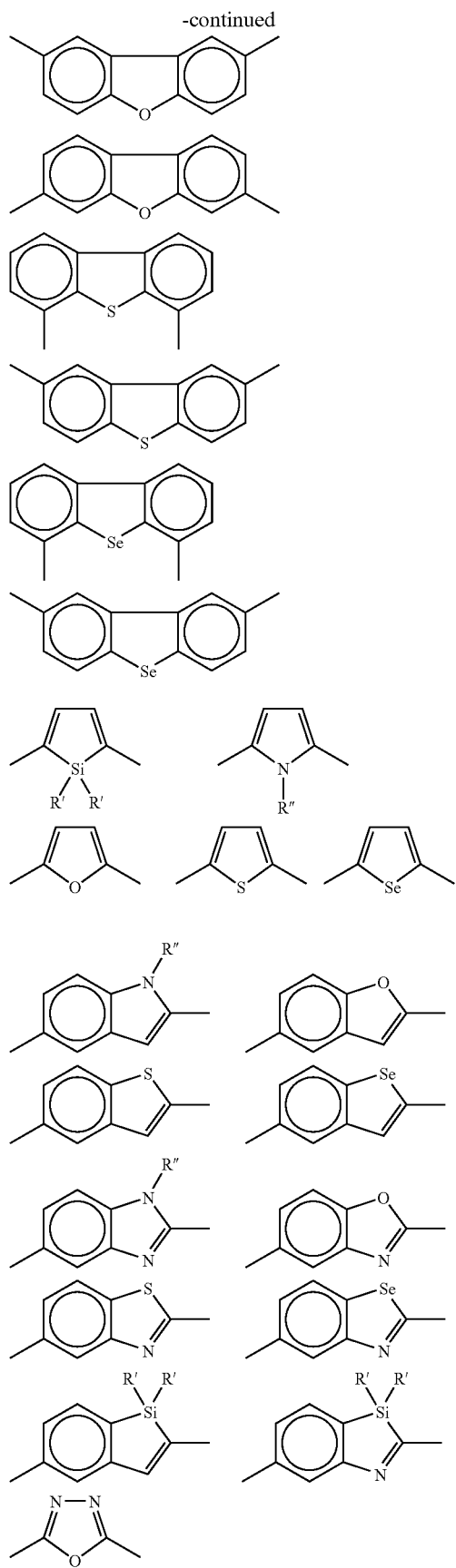

(40)

(41)

-continued

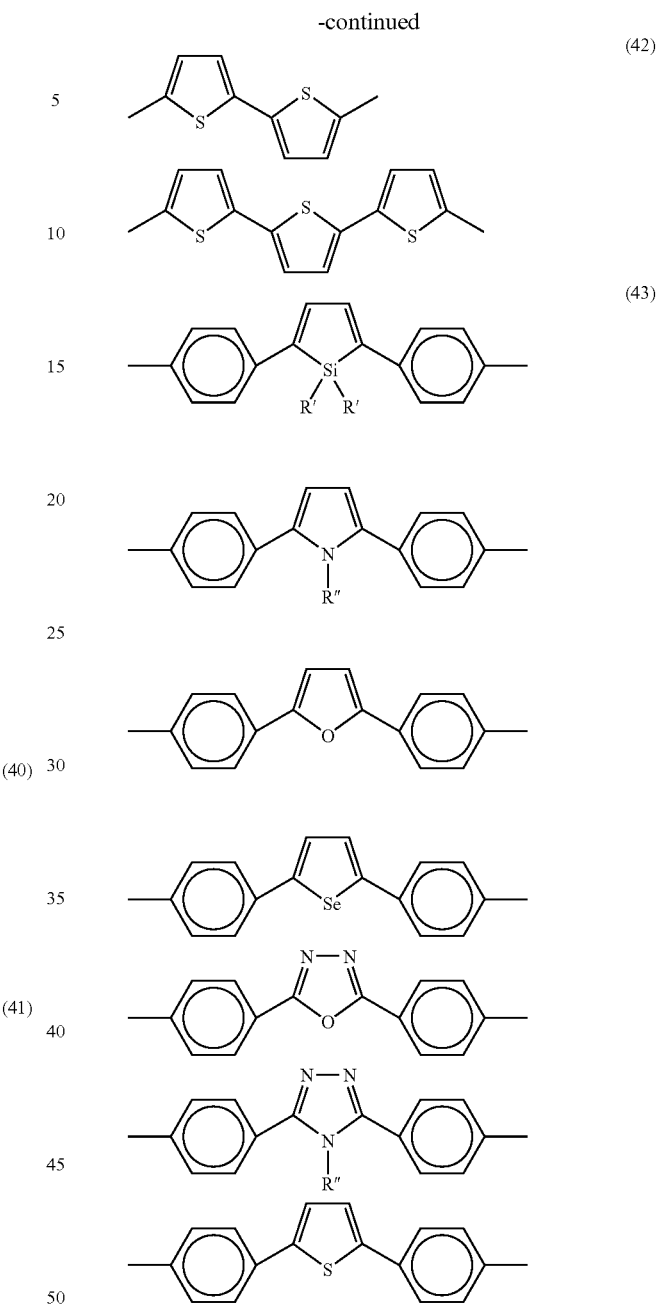

(42)

(43)

In the above formula, R' each independently represents a hydrogen atom, a halogen atom, an alkyl group, alkyloxy group, alkylthio group, alkyl amino group, aryl group, aryloxy group, arylthio group, aryl amino group, arylalkyl group, arylalkyloxy group, aryl alkylthio group, arylalkylamino group, acyloxy group, amide group, arylalkenyl group, arylalkynyl group, monovalent heterocyclic group, or cyano group. R" represents a hydrogen atom, an alkyl group, aryl group, arylalkyl group, silyl group, acyl group, or monovalent heterocyclic group.

The divalent heterocyclic group includes, for example, a triplet luminescence complex etc. and the following divalent metal-complex groups are exemplified.

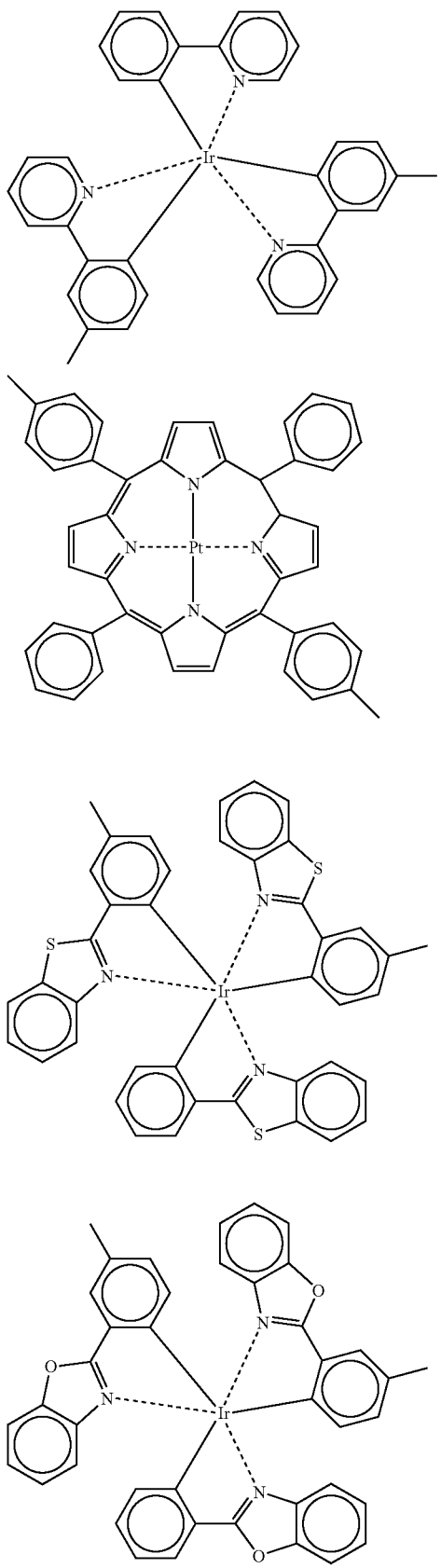
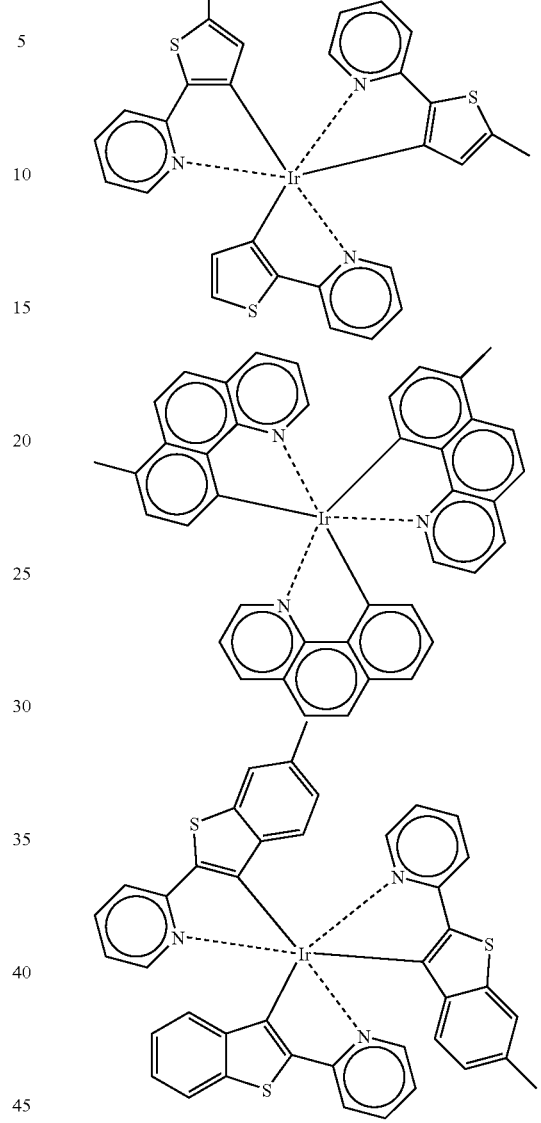

As the examples of the arylene group or divalent heterocyclic group, the arylene groups or divalent heterocyclic groups contained in the materials conventionally used as EL luminescence materials are also exemplified. These materials are disclosed in, for example, WO 99/12989, WO 00/55927, WO 01/49769A1, WO01/49768A2, WO98/06773, U.S. Pat. No. 5,777,070, WO 99/54385, WO 00/46321, and U.S. Pat. No. 6,169,163B1.

The repeating unit other than the repeating unit represented by the above formula (1), preferably contains a repeating unit represented by the below formula (8), in view of life time of a device.

(8)

[in the formula, $Ar^1$ and $Ar^2$ each independently represent an arylene group or divalent heterocyclic group; $R^{11}$ represents an alkyl group, aryl group, monovalent heterocyclic group, a group represented by the below formula (9) or (10); m represents an integer of 1 to 4,

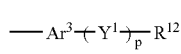 (9)

(in the formula, $Ar^3$ represents an arylene group or divalent heterocyclic group; $R^{12}$ represents a hydrogen atom, an alkyl group, aryl group, monovalent heterocyclic group, or a group represented by the below formula (10); $Y^1$ represents $-CR^{13}=CR^{14}-$, or $-C\equiv C-$; $R^{13}$ and $R^{14}$ each independently represent a hydrogen atom, an alkyl group, aryl group, monovalent heterocyclic group, or cyano group; p represents an integer of 0-2),

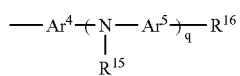 (10)

(in the formula, $Ar^4$ and $Ar^5$ each independently represent an arylene group or a divalent heterocyclic group; $R^{15}$ represents an alkyl group, aryl group, or monovalent heterocyclic group; $R^{16}$ represents a hydrogen atom, an alkyl group, aryl group, or monovalent heterocyclic group; q represents an integer of 1 to 4)].

Specific examples of the arylene group, and divalent heterocyclic group for $Ar^1$—$Ar^5$ in the above formulas (8)-(10) are the same as those aforementioned. Specific examples of the alkyl group, aryl group, and monovalent heterocyclic group for $R^{11}$—$R^{16}$ in the above formulas (8)-(10) are the same as those aforementioned.

As the preferable examples of the repeating unit represented by the above formula (8), exemplified are the followings which may have a substituent on the benzene ring or heterocyclic ring. As the substituent, a halogen atom, an alkyl group, alkyloxy group, alkylthio group, alkylamino group, aryl group, aryloxy group, arylthio group, arylamino group, arylalkyl group, arylalkyloxy group, arylalkylthio group, arylalkylamino group, acyl group, acyloxy group, amide group, imino group, silyl group, silyloxy group, silylthio group, silylamino group, monovalent heterocyclic group, arylalkenyl group, arylethynyl group, and cyano group are exemplified.

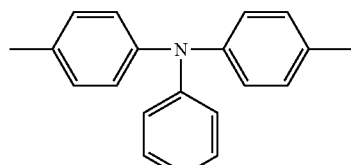

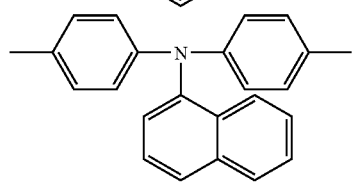

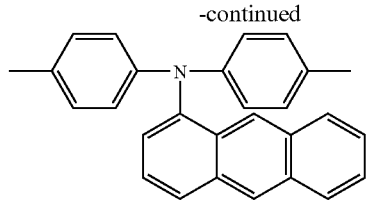

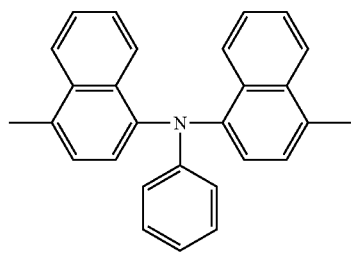

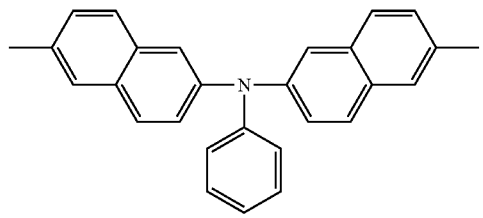

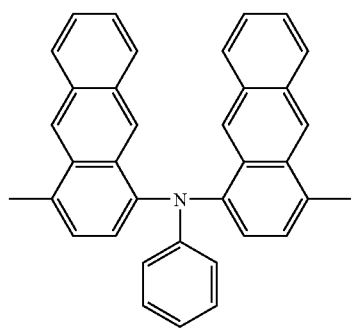

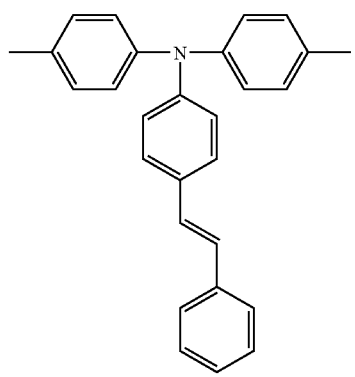

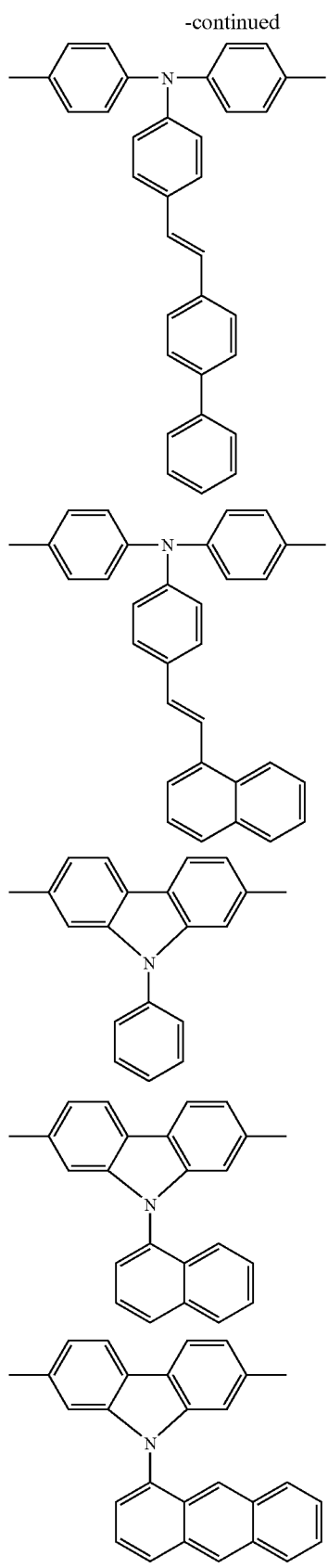
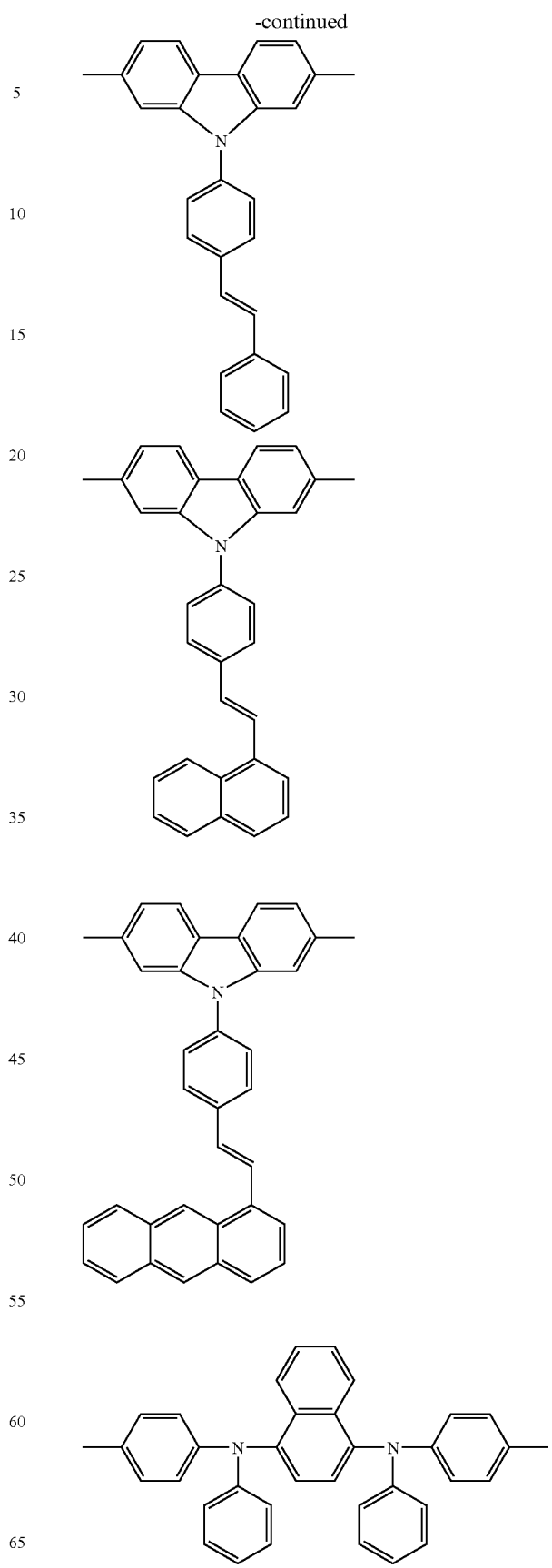

-continued

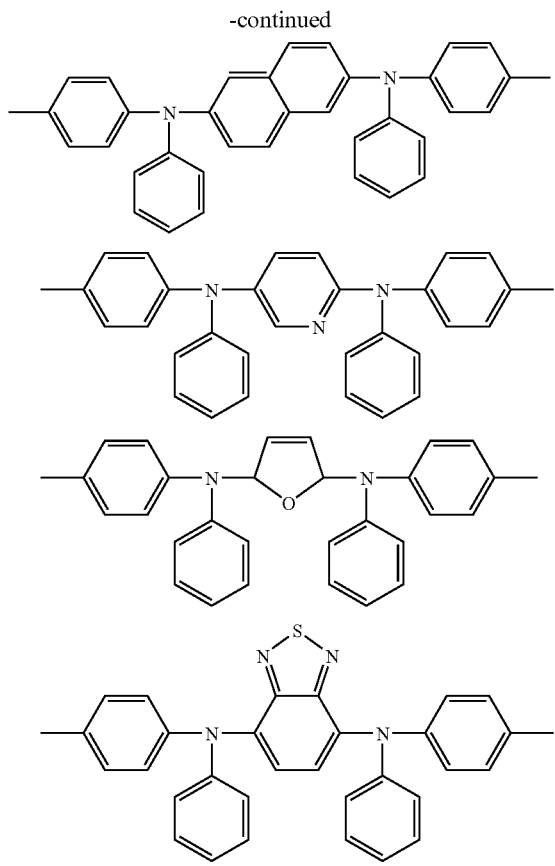

The repeating units contained in the polymer of the present invention may be connected by non-conjugated units, and may have a non-conjugated portion in the repeating units themselves.

As the non-conjugated unit, exemplified are groups shown below, those in which the group shown below is combined with a vinylene groups, and those in which two or more kinds of the groups shown below are combined. R is a group selected from the group consisting of a hydrogen atom, alkyl group having 1 to 20 carbon atoms, aryl group having 6 to 60 carbon atoms, and a heterocyclic group having 4 to 60 carbon atoms, and Ar represents a hydrocarbon group having 6 to 60 carbon atoms.

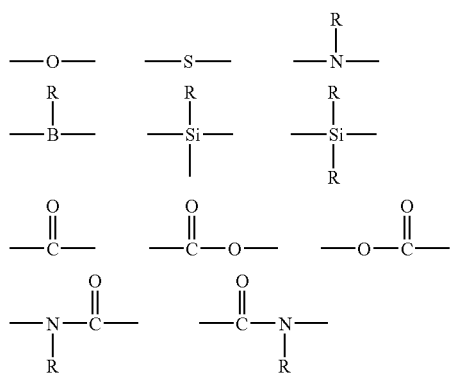

-continued

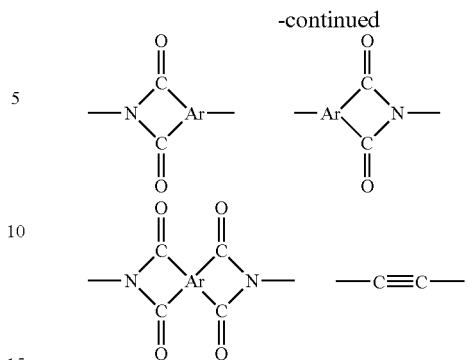

The polymer may also be a random, block or graft copolymer, or a polymer having an intermediate structure thereof, for example, a random copolymer having block property. From the viewpoint for obtaining a polymer having high fluorescent quantum yield, random copolymers having block property and block or graft copolymers are more preferable than complete random copolymers. Further, the polymer have a branched main chain and more than three terminals, and a dendrimer.

The end group of polymer may also be protected with a stable group since if a polymerization active group remains intact, there is a possibility of reduction in light emitting property and life-time when the fluorescent substance is made into an device. Those having a conjugated bond continuing to a conjugated structure of the main chain are preferable, and there are exemplified structures connected to an aryl group or heterocyclic compound group via a carbon-carbon bond. Specifically, substituents of the chemical formula 10 in JP-A No. 9-45478 are exemplified.

The polymer has a polystyrene reduced number average molecular weight of $10^3$ to $10^8$. Degree of polymerization thereof changes according to the structure of the repeating units or the ratio thereof. From the viewpoint of film-molding property, generally the total number of repeating units are preferably 20 to 10000, more preferably 30 to 10000, and further preferably 50 to 5000.

As good solvents for the polymer, there are exemplified chloroform, methylene chloride, dichloroethane, tetrahydrofuran, toluene, xylene, mesitylene, tetralin, decalin, n-butylbenzene and the like. The polymer can be usually dissolved in these solvents in an amount of 0.1 wt % or more, though the amount differs depending on the structure and molecular weight of the polymer.

The polymer of the present invention can be manufactured by condensation polymerization, using a compound represented by the below formula (11).

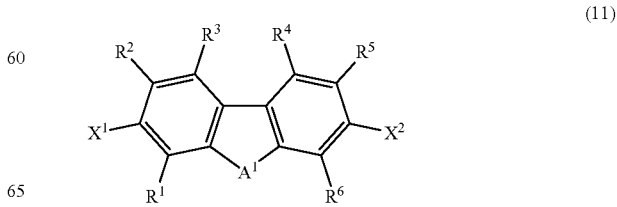

(11)

(in the formula, $R^1$, $R^2$, $R^3$, $R^4$, $R^5$, $R^6$, and $A^1$ represent the same as those in formula (1); $x^1$ and $x^2$ each independently represent a substituent capable of condensation polymerization.)

As the substituents capable of condensation polymerization, exemplified are: a halogen atom, alkyl sulfonate group, aryl sulfonate group, arylalkyl sulfonate group, borate group, sulfonium methyl group, phosphonium methyl group, phosphonate methyl group, monohalogenated-methyl group, boric-acid group, formyl group, cyano group, vinyl group, etc.; and preferably a halogen atom, alkyl sulfonate group, aryl sulfonate group, and arylalkyl sulfonate group.

Here, as the alkyl sulfonate group, methane sulfonate group, ethane sulfonate group, trifluoromethane sulfonate group, etc. are exemplified. As the aryl sulfonate group, benzene sulfonate group, p-toluene sulfonate group, etc. are exemplified. As the aryl sulfonate group, benzyl sulfonate group etc. are exemplified.

As the boric-acid ester group, groups represented by the below formulas are exemplified.

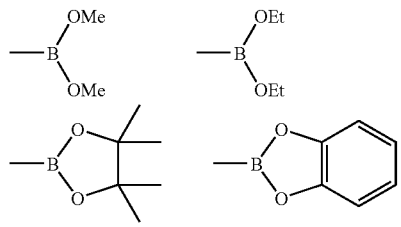

In the formula, Me shows a methyl group and Et shows an ethyl group.

As the sulfonium methyl group, groups represented by the below formulas are exemplified.

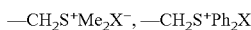

(X shows a halogen atom and Ph shows a phenyl group.)

As the phosphonium methyl group, groups represented by the below formulas are exemplified.

—$CH_2P^+Ph_3X^-$ (X shows a halogen atom)

As the phosphonate methyl group, groups represented by the below formulas are exemplified.

—$CH_2PO(OR')_2$ (R' shows an alkyl group, an aryl group, or an arylalkyl group.)

As the monohalogenated-methyl group, fluoromethyl group, chloromethyl group, bromomethyl group, and iodomethyl group are exemplified.

For example, in the above formula (1), a polymer whose $A^1$ is a divalent group represented by the above formula (4) can be manufactured by using a compound whose $A^1$ is a divalent group represented by the above formula (4) in the above formula (11).

Moreover, a polymer whose $A^1$ is a divalent group represented by the above (5) formula in the above formula (1) can be manufactured, by using a compound whose $A^1$ is a divalent group represented by the above (5) formula in the above formula (11).

A polymer whose $A^1$ is a divalent group represented by the above (6) formula in the above formula (1), $A^2$ is Si, and l is 1, can be manufactured by using a compound whose $A^1$ is a divalent group represented by the above (6) formula in the above formula (11), and $A^2$ is Si, and l is 1 is used.

Furthermore, a polymer whose $A^1$ is a divalent group, represented by the above (6) formula in the above formula (1), $A^2$ is Si, and l is 2, can be manufactured by using a compound whose $A^1$ is a divalent group represented by the above (6) formula in the above formula (11), and $A^2$ is Si, and l is 2 is used.

Moreover, when the polymer of the present invention has a repeating unit other than the repeating unit of formula (1), a condensation polymerization just can be carried out using together with a monomer as the repeating unit other than the repeating unit of formula (1).

As the monomer used as the repeating unit other than the repeating unit of formula (1), compounds of the below formulas (7-2) and (8-2) are exemplified, and the below formula (8-2) is preferable.

 (7-2)

(In the formula, $Ar^6$, $R^{17}$ and $R^{18}$ represent the same as those in formula (7); $x^1$ and $x^2$ are the same as those in formula (11); n represents an integer of 0-1.)

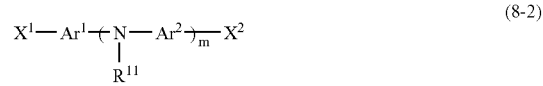 (8-2)

(In the formula, $Ar^1$, $Ar^2$, and $R^{11}$ represent the same as those in formula (8); $x^1$ and $x^2$ represent the same as those in formula (11); m represents an integer of 0-4.)

In the manufacture method of the polymer of the present invention, as the method of carrying out condensation polymerization of a compound represented by the above formula (11) which is a raw material, and a monomer as the repeating unit other than the repeating unit of formula (1), known condensation reactions can be used according to the kind of substituents used for condensation polymerization in each of monomers according to requirements.

As a method of producing the polymer of the present invention, for example, a method described in JP-A No. 5-202355 is exemplified, when a vinylene group is contained in the main chain. Namely, there are exemplified methods such as polymerization of a compound having a formyl group with a compound having a phosphonium methyl group, or of a compound having a formyl group and a phosphonium methyl group, according to a Wittig reaction, polymerization of a compound having a vinyl group with a compound having a halogen atom, according to a Heck reaction, polycondensation of a compound having two or more halogenated methyl groups, according to a de-hydrohalogenating method, polycondensation of a compound having two or more sulfonium salt groups, according to a sulfonium salt-decomposing method, polymerization of a compound having a formyl group with a compound having a cyano group, according to a Knoevenagel reaction, polymerization of a compound having two or more formyl groups, according to McMurry reaction, and the like.

When a vinylene group is not contained in the main chain, for example, a method of polymerization from corresponding monomers by a Suzuki coupling reaction, a method of polymerization by a Grignard reaction, a method of polymerization using a Ni(0) catalyst, a method of polymerization using an oxidizer such as $FeCl_3$ and the like, a method of oxidation polymerization electrochemically, a method of decomposition of an intermediate polymer having a suitable releasing group, and the like are exemplified.

Of these, the polymerization method by a Wittig reaction, the polymerization method by a Heck reaction, the polymerization method by a Horner-Wadsworth-Emmons method, the polymerization method by a Knoevenagel reaction, the polymerization method by a Suzuki coupling reaction, the polymerization method by a Grignard reaction and the polymerization method using a Ni(0) catalyst are preferable since structure control is easy in these methods.

Among the manufacture methods of the present invention, it is suitable to conduct a condensation polymerization of a compound as a monomer represented by the above formula (11) in which $x^1$ and $x^2$ are each independently a halogen atom, alkyl sulfonate group, aryl sulfonate group or arylalkyl sulfonate group, preferably a halogen atom, using a palladium catalyst or a nickel catalyst.

In the manufacture method of the present invention, the-compound of the above formula (11) used as a raw material monomer, and a monomer, such as the above formula (7-2) or a formula (8-2) are, if necessary, dissolved in an organic solvent, and reacted at a temperature of below the boiling point and above the melting point of the organic solvent, using an alkali or a suitable catalyst, if necessary. For example, known methods can be used, described in "Organic Reactions", vol. 14, pp. 270 to 490, John Wiley & Sons, Inc., 1965, "Organic Reactions", vol. 27, pp. 345 to 390, John Wiley & Sons, Inc., 1982, "Organic Synthesis", Collective Volume VI, pp. 407 to 411, John Wiley & Sons, Inc., 1988, Chemical Review, vol. 95, p. 2457 (1995), Journal of Organometallic Chemistry, vol. 576, p. 147 (1999), Journal of Praktical Chemistry, vol. 336, p. 247 (1994), Makromolecular Chemistry Macromolecular Symposium, vol. 12, p. 229 (1987), and the like.

It is preferable that the organic solvent used is subjected to a deoxygenation treatment sufficiently and the reaction is progressed under an inert atmosphere, generally for suppressing a side reaction, though the treatment differs depending on compounds and reactions used. Further, it is preferable to conduct a dehydration treatment likewise (however, this is not applicable in the case of a reaction in a two-phase system with water, such as a Suzuki coupling reaction).

In order to promote the reaction, an alkali or a catalyst is added appropriately. These may be selected according to the reaction. It is preferable that the alkali or catalyst is soluble sufficiently in a solvent used for the reaction. As the method of mixing an alkali or catalyst, there is exemplified a method of adding a solution of an alkali or catalyst slowly while stirring under an inner atmosphere of argon and nitrogen and the like or a method of slowly adding the reaction solution to a solution of an alkali or catalyst, inversely.

It is preferable to polymerize, after purifying the monomer before a polymerization by methods, such as distillation, sublimation purification, and recrystallization, since the purity may affect the performance of devices, such as luminescence characteristics, when using the polymer of the present invention for polymer LED. Moreover, it is preferable to carry out purification processing such as reprecipitation purification, and fractionation by chromatography etc. after polymerization.

A compound represented by the below formula (12) which is a divalent group whose $A^1$ in the above formula (11) is represented by the above (4) formula,

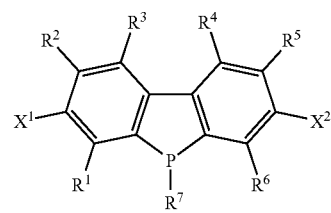

can be prepared by: after metalating the two iodine atoms of the compound below formula (13) selectively,

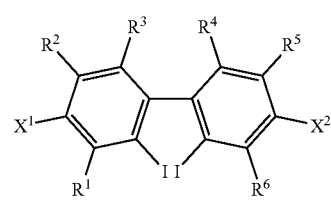

[in the formula, $R^1$, $R^2$, $R^3$, $R^4$, $R^5$, $R^6$, $x^1$ and $x^2$ represent the same as the above], and reacting it with a dihalogenated phosphorous compound represented by the below formula (14),

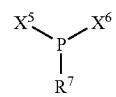

[in the formula, $R^7$ represents the same as the above; x5 and x6 each independently represents a chlorine atom, a bromine atom, or an iodine atom.]

The reaction can be carried out under inert atmospheres, such as nitrogen and argon, in the presence of a solvent. As the solvent used for reaction, exemplified are: saturated hydrocarbons, such as pentane, hexane, heptane, octane, and cyclohexane; unsaturated hydrocarbons, such as benzene, toluene, xylene, and ethylbenzene; ethers, such as dimethyl ether, diethyl ether, methyl-t-butyl ether, di-t-butyl ether, tetrahydrofuran, tetrahydropyran, and dioxane; and amines, such as trimethylamine, triethylamine, N,N,N',N'-tetramethylethylenediamine, and pyridine. These may be used as alone or a mixture thereof.

As the metalating agent, methyl lithium, n-butyl lithium, sec-butyl lithium, t-butyl lithium, phenyl lithium, etc. are exemplified. The reaction temperature is usually −30° C. or less, and preferably −80° C. or less in order to metalate selectively.

Moreover, it may be reacted with the dihalogenated phosphorous compound represented by the above formula (14) after exchanging the metal of the compound metalated by the above method.

As the metal exchanging reagent, magnesium salts, such as magnesium chloride and a magnesium bromide: copper salt, such as copper chloride (I), copper chloride (II), copper bromide (I), copper bromide (II), and copper iodide (I); and zinc salts, such as zinc chloride, and zinc bromide, and zinc iodide, are exemplified. In view of yield, magnesium salt is preferable.

As for the reaction with a dihalogenated phosphorous compound represented by the above formula (14), it is preferable to carry out at from −100° C. to the boiling point of a solvent.

After the reaction, it can be obtained by a usual post-treatment, for example, quenching with water, then extracting by an organic solvent, and distilling of the solvent. When the product is unstable to water, it can be obtained by a method of distilling a solvent after removing inorganic salt by filtration.

Isolation and purification of the product can be performed by a method, such as recrystallization, distillation, or fractionation by chromatography.

Moreover, a compound represented the below formula (15) whose $A^1$ is a divalent group represented by the above formula (5) in the above formula (11),

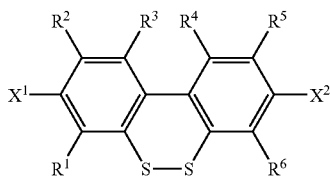
(15)

can be manufactured by: after metalating the two iodine atoms of the compound represented by the above formula (13), and reacting it with sulfur.

About the reaction method, it is the same as that of the synthetic process of the compound represented by the above formula (12). About the reaction with sulfur, it may be added as any form of solid, or dissolved or suspended in a solvent. The temperature of the reaction is from −100° C. to 30° C., and preferably from −80° C. to 0° C. About the post-treatment of reaction, and the purification method, it is also the same as that of the compound represented by the above formula (12).

A compound represented by the below formula (20) whose $A^1$ is a divalent group represented by the above formula (6) in the above formula (11), and $A^2$ is Si, and l is 2,

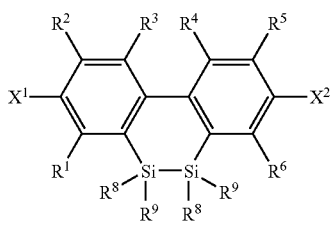

can be manufactured by: after metalating the two iodine atoms of the compound represented by the above formula (13), and reacting it with 1,2-dihalogenated disilyl compound represented by the below formula (22),

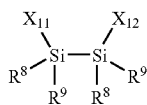
(22)

[in the formula, $R^8$ and $R^9$ represent the same as the above. x11 and x12 each independently represent a chlorine atom, a bromine atom, or an iodine atom.]

About the reaction method, post-treatment, and purification method, it is the same as those of the compound represented by the above formula (12).

Moreover, similarly with the compound represented by the above formula (12), the compound represented by the below formula (3-2) can be manufactured by reacting it with the dihalogenated compound after metalating the two iodine atoms of the compound represented by the above formula (13) selectively. About the method of reaction, post-treatment, and purification method, it is the same as those of the compound represented by the above formula (12).

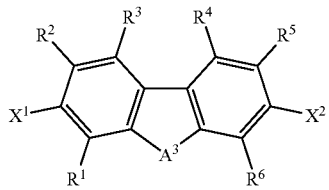
(3-2)

(In the formula, $R^1, R^2, R^3, R^4, R^5$, and $R^6$ represent the same as those in formula (11). $x^1$ and $x^2$ are represent the same as those in formula (11). $A^3$ represents a divalent group selected from

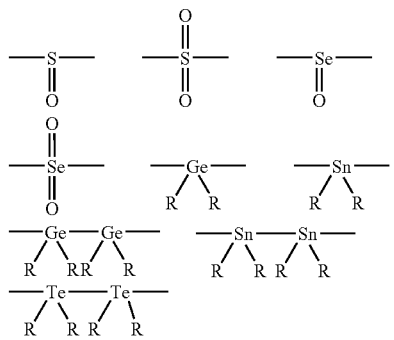

In the formula, R represents the same as aforementioned.) About the reaction method, post-treatment, and purification method, it is the same as those of the compound represented by the above formula (12).

A dibenzosilole derivative represented by the below formula (18) whose $A^1$ is a divalent group represented by the above formula (6) in the above formula (11), and $A^2$ is Si, and l is 1,

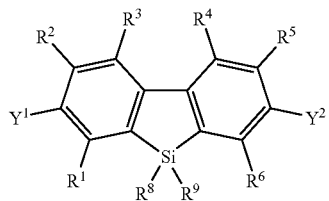
(18)

can be manufactured by reacting a compound (dibenzosilole derivative) represented by the below formula (19), with a halogenation reagent, preferably an N-halogeno compound,

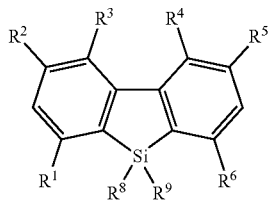

(19)

(in the formula, $R^1$, $R^2$, $R^3$, $R^4$, $R^5$, $R^6$, $R^8$, and $R^9$ represent the same as those in formula (11).)

The reaction can be carried out under inert atmosphere such as nitrogen and argon, in the presence of a solvent. The reaction temperature is preferably from −80° C. to the boiling point of the solvent.

Moreover, it can be manufactured also by a method in which a halogenation reagent is reacted, after reacting the compound represented by formula (19) with a base.

As the N-halogeno compound, N-chloro succinimide, N-chloro phthalic imide, N-chloro diethylamine, N-chloro dibutyl amine, N-chloro cyclohexyl amine, N-bromosuccinimide, N-bromo phthalic-imide, N-bromo ditrifluoromonomethylamine, N-iodo succinimide, N-iodophthalic imide, etc. are exemplified. As the other halogenation reagents, fluorine, fluoroxy trifluoromethane, oxygen difluoride, perchloryl fluoride, cobalt fluoride (III), silver fluoride (II), selenium fluoride (IV), manganese fluoride (III), chlorine, iodine trichloride, aluminum trichloride, tellurium chloride (IV), molybdenum chloride, antimony chloride, iron chloride (III), titanium tetrachloride, phosphorus pentachloride, thionyl chloride, bromine, 1,2-dibromo ethane, boron tribromide, copper bromide, silver bromide, t-butyl bromide, bromine oxide, iodine, iodine monochloride, etc. are ecemplified.

As the solvent used for reaction, exemplified are: saturated hydrocarbons, such as pentane, hexane, heptane, octane, cyclohexane; unsaturated hydrocarbons, such as benzene, toluene, ethylbenzene, xylene; halogenated saturated hydrocarbons, such as carbon tetrachloride, chloroform, dichloromethane, chlorobutane, bromobutane, chloropentane, bromopentane, chlorohexane, bromohexane, chlorocyclohexane, and bromocyclohexane; halogenated unsaturated hydrocarbons, such as chlorobenzene, dichlorobenzene, and trichlorobenzene; alcohols, such as methanol, ethanol, propanol, isopropanol, butanol, t-butyl alcohol; carboxylic acids, such as, formic acid, acetic acid, and propionic acid; ethers, such as, dimethyl ether, diethyl ether, methyl-t-butyl ether, tetrahydrofuran, tetrahydropyran, and dioxane; amines, such as trimethylamine, triethylamine, N,N,N',N'-tetramethylethylenediamine, and pyridine; amides, such as, N,N-dimethylformamide, N,N-dimethylacetamide, N,N-diethyl acetamide, N-methylmorpholine oxide, and N-methyl-2-pyrrolidone. These may be used alone or a mixture thereof.

As the base used for reaction, exemplified are: lithium hydride, sodium hydride, potassium hydride, methyl lithium, n-butyl lithium, t-butyl lithium, phenyl lithium, lithium diisopropyl amide, lithium hexamethyldisilazide, sodium hexa methyldisilazide, potassium hexamethyl disilazide, etc.

After the reaction, it can be obtained by a usual post-treatment, for example, quenching with water, then extracting by an organic solvent, and distilling of the solvent.

Isolation and purification of the product can be performed by a method, such as recrystallization, distillation, or fractionation by chromatography.

Next, the use of the polymer of the present invention is explained.

The polymer of the present invention has strong fluorescence, and it can be used as a polymeric fluorescent substance. Moreover, since the luminescence from a thin film is used, polymeric fluorescent substances having fluorescence in the solid state are used preferably. Moreover, the polymer has excellent electronic transporting property, and can be used suitably as a polymer LED material, or a charge transporting material. The polymer of the present invention can be used also as a material for electronic devices, and can be used also as a coloring matter for lasers, a solar-battery material, an organic semiconductor for organic transistors, and a conductive thin-film material.

Next, the polymer LED of the present invention will be described. The polymer LED of the present invention, has a light-emitting layer between an anode and a cathode, and the polymer-of the present invention is contained in the light-emitting layer.

As the polymer LED of the present invention, there are listed polymer LEDs having an electron transporting layer disposed between a cathode and a light emitting layer, polymer LEDs having a hole transporting layer disposed between an anode and a light emitting layer, polymer LEDs having an electron transporting layer disposed between a cathode and a light emitting layer and having a hole transporting layer disposed between an anode and a light emitting layer.

Moreover, as the polymer LED of the present invention, there are exemplified: a device having a layer containing a conducting polymer disposed between at least one of the electrodes and a light emitting layer, adjacently to said electrode; and a device having an insulating layer having a thickness of 2 nm or less disposed between at least one of the electrodes and a light emitting layer, adjacently to said electrode.

For example, the following structures a) to d) are specifically exemplified.

a) anode/light emitting layer/cathode
b) anode/hole transporting layer/light emitting layer/cathode
c) anode/light emitting layer/electron transporting layer/cathode
d) anode/hole transporting layer/light emitting layer/electron transporting layer/cathode (wherein, "/" indicates adjacent lamination of layers.)

Herein, the light emitting layer is a layer having function to emit a light, the hole transporting layer is a layer having function to transport a hole, and the electron transporting layer is a layer having function to transport an electron. Herein, the electron transporting layer and the hole transporting layer are generically called a charge transporting layer. The light emitting layer, hole transporting layer and electron transporting layer may also each independently used in two or more layers.

Of charge transporting layers disposed adjacent to an electrode, that having function to improve charge injecting efficiency from the electrode and having effect to decrease driving voltage of an device are particularly called sometimes a charge injecting layer (hole injecting layer, electron injecting layer) in general.

For enhancing adherence with an electrode and improving charge injection from an electrode, the above charge injecting layer or insulation layer having a thickness of 2 nm or less may also be provided adjacent to an electrode, and further, for enhancing adherence of the interface, preventing mixing and the like, a thin buffer layer may also be inserted into the interface of a charge transporting layer and light emitting layer.

The order and number of layers laminated and the thickness of each layer can be appropriately applied while considering light emitting efficiency and life of the device.

In the present invention, as the polymer LED having a charge injecting layer (electron injecting layer, hole injecting layer) provided, there are listed a polymer LED having a charge injecting layer provided adjacent to a cathode and a polymer LED having a charge injecting layer provided adjacent to an anode.

For example, the following structures e) to p) are specifically exemplified.

e) anode/charge injecting layer/light emitting layer/cathode
f) anode/light emitting layer/charge injecting layer/cathode
g) anode/charge injecting layer/light emitting layer/charge injecting layer/cathode
h) anode/charge injecting layer/hole transporting layer/light emitting layer/cathode
i) anode/hole transporting layer/light emitting layer/charge injecting layer/cathode
j) anode/charge injecting layer/hole transporting layer/light emitting layer/charge injecting layer/cathode
k) anode/charge injecting layer/light emitting layer/electron transporting layer/cathode
l) anode/light emitting layer/electron transporting layer/charge injecting layer/cathode
m) anode/charge injecting layer/light emitting layer/electron transporting layer/charge injecting layer/cathode
n) anode/charge injecting layer/hole transporting layer/light emitting layer/electron transporting layer/cathode
o) anode/hole transporting layer/light emitting layer/electron transporting layer/charge injecting layer/cathode
p) anode/charge injecting layer/hole transporting layer/light emitting layer/electron transporting layer/charge injecting layer/cathode As the specific examples of the charge injecting layer, there are exemplified: layers containing an conducting polymer; layers which are disposed between an anode and a hole transporting layer and contain a material having an ionization potential between the ionization potential of an anode material and the ionization potential of a hole transporting material contained in the hole transporting layer, and the like.

When the above charge injecting layer is a layer containing an conducting polymer, the electric conductivity of the conducting polymer is preferably $10^{-5}$ S/cm or more and $10^3$ S/cm or less, and for decreasing the leak current between light emitting pixels, more preferably $10^{-5}$ S/cm or more and $10^2$ S/cm or less, further preferably $10^{-5}$ S/cm or more and $10^1$ S/cm or less.

Usually, to provide an electric conductivity of the conducting polymer of $10^{-5}$ S/cm or more and $10^3$ S/cm or less, a suitable amount of ions are doped into the conducting polymer.

Regarding the kind of an ion to be doped, an anion is used for a hole injecting layer and a cation is used for an electron injecting layer. As examples of the anion, a polystyrene sulfonate ion, alkylbenzene sulfonate ion, camphor sulfonate ion and the like are exemplified, and as examples of the cation, a lithium ion, sodium ion, potassium ion, tetrabutyl ammonium ion and the like are exemplified.

The thickness of the charge injecting layer is for example, from 1 nm to 100 nm, preferably from 2 nm to 50 nm.

Materials used in the charge injecting layer may be selected appropriately according to the relation with the electrode materials and adjacent layers, and there are exemplified conducting polymers such as polyaniline and derivatives thereof, polythiophene and derivatives thereof, polypyrrole and derivatives thereof, poly(phenylene vinylene) and derivatives thereof, poly(thienylene vinylene) and derivatives thereof, polyquinoline and derivatives thereof, polyquinoxaline and derivatives thereof, polymers containing aromatic amine structures in the main chain or the side chain, and the like, and metal phthalocyanine (copper phthalocyanine and the like), carbon and the like.

The insulation layer having a thickness of 2 nm or less has function to make charge injection easy. As the material of the above insulation layer, metal fluoride, metal oxide, organic insulation materials and the like are listed. As the polymer LED having an insulation layer having a thickness of 2 nm or less, there are listed polymer LEDs having an insulation layer having a thickness of 2 nm or less provided adjacent to a cathode, and polymer LEDs having an insulation layer having a thickness of 2 nm or less provided adjacent to an anode.

Specifically, there are listed the following structures q) to ab) for example.

q) anode/insulation layer having a thickness of 2 nm or less/light emitting layer/cathode
r) anode/light emitting layer/insulation layer having a thickness of 2 nm or less/cathode
s) anode/insulation layer having a thickness of 2 nm or less/light emitting layer/insulation layer having a thickness of 2 nm or less/cathode
t) anode/insulation layer having a thickness of 2 nm or less/hole transporting layer/light emitting layer/cathode
u) anode/hole transporting layer/light emitting layer/insulation layer having a thickness of 2 nm or less/cathode
v) anode/insulation layer having a thickness of 2 nm or less/hole transporting layer/light emitting layer/insulation layer having a thickness of 2 nm or less/cathode
w) anode/insulation layer having a thickness of 2 nm or less/light emitting layer/electron transporting layer/cathode
x) anode/light emitting layer/electron transporting layer/insulation layer having a thickness of 2 nm or less/cathode
y) anode/insulation layer having a thickness of 2 nm or less/light emitting layer/electron transporting layer/insulation layer having a thickness of 2 nm or less/cathode
z) anode/insulation layer having a thickness of 2 nm or less/hole transporting layer/light emitting layer/electron transporting layer/cathode
aa) anode/hole transporting layer/light emitting layer/electron transporting layer/insulation layer having a thickness of 2 nm or less/cathode
ab) anode/insulation layer having a thickness of 2 nm or less/hole transporting layer/light emitting layer/electron transporting layer/insulation layer having a thickness of 2 nm or less/cathode In producing a polymer LED, when a film is formed from a solution by using such polymer soluble in an organic solvent, only required is removal of the solvent by drying after coating of this solution, and even in the case of mixing of a charge transporting material and a light emitting material, the same method can be applied, causing an extreme advantage in production. As the film forming method from a solution, there can be used coating methods such as a spin coating method, casting method, micro gravure coating method, gravure coating method, bar coating method, roll coating method, wire bar coating method, dip coating method, spray coating method, screen printing method, flexo printing method, offset printing method, inkjet printing method and the like.

Regarding the thickness of the light emitting layer, the optimum value differs depending on material used, and may properly be selected so that the driving voltage and the light emitting efficiency become optimum values, and for example, it is from 1 nm to 1 µm, preferably from 2 nm to 500 nm, further preferably from 5 nm to 200 nm.

In the polymer LED of the present invention, light emitting materials other than the above polymeric fluorescent substance can also be mixed in a light emitting layer. Further, in the polymer LED of the present invention, the light emitting layer containing light emitting materials other than the above polymeric fluorescent substance may also be laminated with a light emitting layer containing the above polymeric fluorescent substance.

As the light emitting material, known materials can be used. In a compound having lower molecular weight, there can be used, for example, naphthalene derivatives, anthracene or derivatives thereof, perylene or derivatives thereof; dyes such as polymethine dyes, xanthene dyes, coumarine dyes, cyanine dyes; metal complexes of 8-hydroxyquinoline or derivatives thereof, aromatic amine, tetraphenylcyclopentane or derivatives thereof, or tetraphenylbutadiene or derivatives thereof, and the like.

Specifically, there can be used known compounds such as those described in JP-A Nos. 57-51781, 59-195393 and the like, for example.

When the polymer LED of the present invention has a hole transporting layer, as the hole transporting materials used, there are exemplified polyvinylcarbazole or derivatives thereof, polysilane or derivatives thereof, polysiloxane derivatives having an aromatic amine in the side chain or the main chain, pyrazoline derivatives, arylamine derivatives, stilbene derivatives, triphenyldiamine derivatives, polyaniline or derivatives thereof, polythiophene or derivatives thereof, polypyrrole or derivatives thereof, poly(p-phenylenevinylene) or derivatives thereof, poly(2,5-thienylenevinylene) or derivatives thereof, or the like.

Specific examples of the hole transporting material include those described in JP-A Nos. 63-70257, 63-175860, 2-135359, 2-135361, 2-209988, 3-37992 and 3-152184.

Among them, as the hole transporting materials used in the hole transporting layer, preferable are polymer hole transporting materials such as polyvinylcarbazole or derivatives thereof, polysilane or derivatives thereof, polysiloxane derivatives having an aromatic amine compound group in the side chain or the main chain, polyaniline or derivatives thereof, polythiophene or derivatives thereof, poly(p-phenylenevinylene) or derivatives thereof, poly(2,5-thienylenevinylene) or derivatives thereof, or the like, and further preferable are polyvinylcarbazole or derivatives thereof, polysilane or derivatives thereof and polysiloxane derivatives having an aromatic amine compound group in the side chain or the main chain. In the case of a hole transporting material having lower molecular weight, it is preferably dispersed in a polymer binder for use.

Polyvinylcarbazole or derivatives thereof are obtained, for example, by cation polymerization or radical polymerization from a vinyl monomer.

As the polysilane or derivatives thereof, there are exemplified compounds described in Chem. Rev., 89, 1359 (1989) and GB 2300196 published specification, and the like. For synthesis, methods described in them can be used, and a Kipping method can be suitably used particularly.

As the polysiloxane or derivatives thereof, those having the structure of the above hole transporting material having lower molecular weight in the side chain or main chain, since the siloxane skeleton structure has poor hole transporting property. Particularly, there are exemplified those having an aromatic amine having hole transporting property in the side chain or main chain.

The method for forming a hole transporting layer is not restricted, and in the case of a hole transporting layer having lower molecular weight, a method in which the layer is formed from a mixed solution with a polymer binder is exemplified. In the case of a polymer hole transporting material, a method in which the layer is formed from a solution is exemplified.

The solvent used for the film forming from a solution is not particularly restricted providing it can dissolve a hole transporting material. As the solvent, there are exemplified chlorine solvents such as chloroform, methylene chloride, dichloroethane and the like, ether solvents such as tetrahydrofuran and the like, aromatic hydrocarbon solvents such as toluene, xylene and the like, ketone solvents such as acetone, methyl ethyl ketone and the like, and ester solvents such as ethyl acetate, butyl acetate, ethylcellosolve acetate and the like.

As the film forming method from a solution, there can be used coating methods such as a spin coating method, casting method, micro gravure coating method, gravure coating method, bar coating method, roll coating method, wire bar coating method, dip coating method, spray coating method, screen printing method, flexo printing method, offset printing method, inkjet printing method and the like, from a solution.

The polymer binder mixed is preferably that does not disturb charge transport extremely, and that does not have strong absorption of a visible light is suitably used. As such polymer binder, polycarbonate, polyacrylate, poly(methyl acrylate), poly(methyl methacrylate), polystyrene, poly(vinyl chloride), polysiloxane and the like are exemplified.

Regarding the thickness of the hole transporting layer, the optimum value differs depending on material used, and may properly be selected so that the driving voltage and the light emitting efficiency become optimum values, and at least a thickness at which no pin hole is produced is necessary, and too large thickness is not preferable since the driving voltage of the device increases. Therefore, the thickness of the hole transporting layer is, for example, from 1 nm to 1 µm, preferably from 2 nm to 500 nm, further preferably from 5 nm to 200 nm.

When the polymer LED of the present invention has an electron transporting layer, known compounds are used as the electron transporting materials, and there are exemplified oxadiazole derivatives, anthraquinonedimethane or derivatives thereof, benzoquinone or derivatives thereof, naphthoquinone or derivatives thereof, anthraquinone or derivatives thereof, tetracyanoanthraquinodimethane or derivatives thereof, fluorenone derivatives, diphenyldicyanoethylene or derivatives thereof, diphenoquinone derivatives, or metal complexes of 8-hydroxyquinoline or derivatives thereof, polyquinoline and derivatives thereof, polyquinoxaline and derivatives thereof, polyfluorene or derivatives thereof, and the like.

Specifically, there are exemplified those described in JP-A Nos. 63-70257, 63-175860, 2-135359, 2-135361, 2-209988, 3-37992 and 3-152184.

Among them, oxadiazole derivatives, benzoquinone or derivatives thereof, anthraquinone or derivatives thereof, or metal complexes of 8-hydroxyquinoline or derivatives thereof, polyquinoline and derivatives thereof, polyquinoxaline and derivatives thereof, polyfluorene or derivatives thereof are preferable, and 2-(4-biphenyl)-5-(4-t-butylphenyl)-1,3,4-oxadiazole, benzoquinone, anthraquinone, tris(8-quinolinol)aluminum and polyquinoline are further preferable.

The method for forming the electron transporting layer is not particularly restricted, and in the case of an electron transporting material having lower molecular weight, a vapor deposition method from a powder, or a method of film-forming from a solution or melted state is exemplified, and in the case of a polymer electron transporting material, a method of film-forming from a solution or melted state is exemplified, respectively. At the time of film forming from a solution or a molten state, a polymer binder can be used together.

The solvent used in the film-forming from a solution is not particularly restricted provided it can dissolve electron transporting materials and/or polymer binders. As the solvent, there are exemplified chlorine solvents such as chloroform, methylene chloride, dichloroethane and the like, ether solvents such as tetrahydrofuran and the like, aromatic hydrocarbon solvents such as toluene, xylene and the like, ketone solvents such as acetone, methyl ethyl ketone and the like, and ester solvents such as ethyl acetate, butyl acetate, ethylcellosolve acetate and the like.

As the film-forming method from a solution or melted state, there can be used coating methods such as a spin coating method, casting method, micro gravure coating method, gravure coating method, bar coating method, roll coating method, wire bar coating method, dip coating method, spray coating method, screen printing method, flexo printing method, offset printing method, inkjet printing method and the like.

The polymer binder to be mixed is preferably that which does not extremely disturb a charge transport property, and that does not have strong absorption of a visible light is suitably used. As such polymer binder, poly(N-vinylcarbazole), polyaniline or derivatives thereof, polythiophene or derivatives thereof, poly(p-phenylene vinylene) or derivatives thereof, poly(2,5-thienylene vinylene) or derivatives thereof, polycarbonate, polyacrylate, poly(methyl acrylate), poly(methyl methacrylate), polystyrene, poly(vinyl chloride), polysiloxane and the like are exemplified.

Regarding the thickness of the electron transporting layer, the optimum value differs depending on material used, and may properly be selected so that the driving voltage and the light emitting efficiency become optimum values, and at least a thickness at which no pin hole is produced is necessary, and too large thickness is not preferable since the driving voltage of the device increases. Therefore, the thickness of the electron transporting layer is, for example, from 1 nm to 1 µm, preferably from 2 nm to 500 nm, further preferably from 5 nm to 200 nm.

The substrate forming the polymer LED of the present invention may preferably be that does not change in forming an electrode and layers of organic materials, and there are exemplified glass, plastics, polymer film, silicon substrates and the like. In the case of a opaque substrate, it is preferable that the opposite electrode is transparent or semitransparent.

In the present invention, at least one of an anode or a cathode is transparent or semitransparent, and it is preferable that the anode is transparent or semitransparent. As the material of this anode, electron conductive metal oxide films, semitransparent metal thin films and the like are used. Specifically, there are used indium oxide, zinc oxide, tin oxide, and films (NESA and the like) fabricated by using an electron conductive glass composed of indium-tin-oxide (ITO), indium.zinc.oxide and the like, which are metal oxide complexes, and gold, platinum, silver, copper and the like are used, and among them, ITO, indium.zinc.oxide, tin oxide are preferable. As the fabricating method, a vacuum vapor deposition method, sputtering method, ion plating method, plating method and the like are used. As the anode, there may also be used organic transparent conducting films such as polyaniline or derivatives thereof, polythiophene or derivatives thereof and the like.

The thickness of the anode can be appropriately selected while considering transmission of a light and electric conductivity, and for example, from 10 nm to 10 µm, preferably from 20 nm to 1 µm, further preferably from 50 nm to 500 nm.

Further, for easy charge injection, there may be provided on the anode a layer comprising a phthalocyanine derivative conducting polymers, carbon and the like, or a layer having an average film thickness of 2 nm or less comprising a metal oxide, metal fluoride, organic insulating material and the like.

As the material of a cathode used in the polymer LED of the present invention, that having lower work function is preferable. For example, there are used metals such as lithium, sodium, potassium, rubidium, cesium, beryllium, magnesium, calcium, strontium, barium, aluminum, scandium, vanadium, zinc, yttrium, indium, cerium, samarium, europium, terbium, ytterbium and the like, or alloys comprising two of more of them, or alloys comprising one or more of them with one or more of gold, silver, platinum, copper, manganese, titanium, cobalt, nickel, tungsten and tin, graphite or graphite intercalation compounds and the like. Examples of alloys include a magnesium-silver alloy, magnesium-indium alloy, magnesium-aluminum alloy, indium-silver alloy, lithium-aluminum alloy, lithium-magnesium alloy, lithium-indium alloy, calcium-aluminum alloy and the like. The cathode may be formed into a laminated structure of two or more layers.

The thickness of the cathode can be appropriately selected while considering transmission of a light and electric conductivity, and for example, from 10 nm to 10 µm, preferably from 20 nm to 1 µm, further preferably from 50 nm to 500 nm.

As the method for fabricating a cathode, there are used a vacuum vapor deposition method, sputtering method, lamination method in which a metal thin film is adhered under heat and pressure, and the like. Further, there may also be provided, between a cathode and an organic layer, a layer comprising an conducting polymer, or a layer having an average film thickness of 2 nm or less comprising a metal oxide, metal fluoride, organic insulation material and the like, and after fabrication of the cathode, a protective layer may also be provided which protects the polymer LED. For stable use of the polymer LED for a long period of time, it is preferable to provide a protective layer and/or protective cover for protection of the device in order to prevent it from outside damage.

As the protective layer, there can be used a polymer, metal oxide, metal fluoride, metal borate and the like. As the protective cover, there can be used a glass plate, a plastic plate the surface of which has been subjected to lower-water-permeation treatment, and the like, and there is suitably used a method in which the cover is pasted with an device substrate by a thermosetting resin or light-curing resin for sealing. If space is maintained using a spacer, it is easy to prevent an device from being injured. If an inner gas such as nitrogen and argon is sealed in this space, it is possible to prevent oxidation of a cathode, and further, by placing a desiccant such as barium oxide and the like in the above space, it is easy to suppress the damage of an device by moisture adhered in the production process. Among them, any one means or more are preferably adopted.

The polymer LED of the present invention can be suitably used as a flat light source, segment display apparatus, dot-matrix display apparatus, and back light of a liquid crystal display.

For obtaining light emission in plane form using the polymer LED of the present invention, an anode and a cathode in the plane form may properly be placed so that they are laminated each other. Further, for obtaining light emission in pattern form, there are a method in which a mask with a window in pattern form is placed on the above plane light emitting device, a method in which an organic layer in non-light emission part is formed to obtain extremely large thickness providing substantial non-light emission, and a method in which any one of an anode or a cathode, or both of them are formed in the pattern. By forming a pattern by any of these methods and by placing some electrodes so that independent on/off is possible, there is obtained a display device of segment type which can display digits, letters, simple marks and the like. Further, for forming a dot matrix device, it may be advantageous that anodes and cathodes are made in the form of stripes and placed so that they cross at right angles. By a method in which a plurality of kinds of polymers emitting different colors of lights are placed separately or a method in which a color filter or luminescence converting filter is used, area color displays and multi color displays are obtained. A dot matrix display can be driven by passive driving, or by active driving combined with TFT and the like. These display devices can be used as a display of a computer, television, portable terminal, portable telephone, car navigation, view finder of a video camera, and the like.

Further, the above light emitting device in plane form is a thin self-light-emitting one, and can be suitably used as a flat light source for back-light of a liquid crystal display, or as a flat light source for illumination. Further, if a flexible plate is used, it can also be used as a curved light source or a display.

EXAMPLES

Hereafter, examples are shown in order to explain the present invention in detail, but the present invention should not be construed to be limited thereto.

In the examples, the number average molecular weight and the weight average molecular weight were determined by gel permeation chromatography (GPC) using chloroform solvent as the polystyrene reduced number average molecular weight and the weight average molecular weight, respectively.

Synthetic Example 1

Synthesis of 2,2'-dibromo-5,5'-dioctyloxy-1,1'-biphenyl

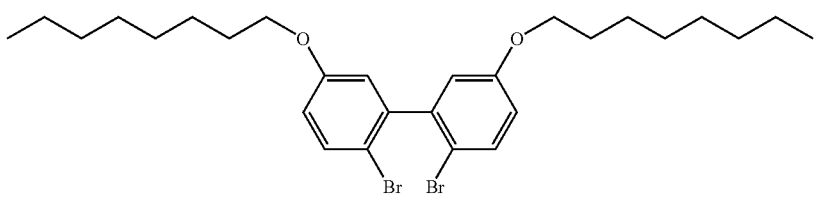

3,3'-dioctyloxy-1,1'-biphenyl which is a raw material was synthesized by Yamamoto coupling, after dioctylation of 3-bromophenol in ethanol.

The above 3,3'-dioctyloxy-1,1'-biphenyl 133 g was dissolved in dried N,N-dimethylformamide 1820 ml. At 0° C. (dry ice-methanol bath), a solution of N-bromosuccinimide 117.5 g/N,N-dimethylformamide 910 ml was added dropwise for 60 minutes. After the dropwise adding, the reaction liquid was brought back to a room temperature and stirred overnight. The reaction liquid was charged into water and extracted with n-hexane, and then the solvent was distilled off and 179 g of crude product was obtained.

ecrystallization was repeated using 2-propanol, and 122 g of 2,2'-dibromo-5,5'-dioctyloxy-1,1'-biphenyl was obtained.

$^1$H-NMR (300 MHz/CDCl$_3$):

δ (ppm)=0.88 [t, 6H], 1.2~1.8 [m, 24H], 3.95 [t, 4H], 6.7~6.8 [m, 4H], 7.52 [d, 2H]

Synthetic Example 2

Synthesis of 2,2'-di-iodo-5,5'-dioctyloxy-1,1'-biphenyl

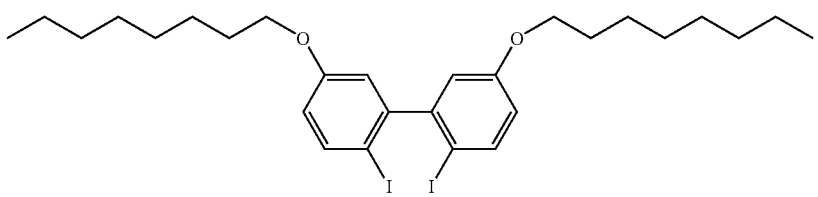

Flaky magnesium 4.05 g was put in a 500 ml three-necked flask under nitrogen atmosphere. Tetrahydrofuran solution 200 ml of the above 2,2'-dibromo-5,5'-dioctyloxy-1,1'-biphenyl 45 g was prepared in another flask, and 20 ml of the solution was added in the flask containing magnesium. Five drops of 1,2-dibromoethane as the initiator was added, and heated. When the exothermic reaction started, the remaining solution was added dropwise for 30 minutes. After the dropwise addition, the reaction was conducted for 1 hour with-refluxing. Then, it was cooled to 0° C., and tetrahydrofuran 150 ml solution of iodine 44.2 g was added dropwise. After the dropwise adding, the reaction liquid was stirred overnight.

The reaction liquid was charged into water and extracted with chloroform, and washed with sodium-thiosulfate aqueous solution and saturated NaCl aqueous solution. After being dried with sodium sulfate, the solvent was distilled off, and 53 g of crude product was obtained.

By recrystallization using 2-propanol, 43 g of 2,2'-di-iodo-5,5'-dioctyloxy-1,1'-biphenyl was obtained.

$^1$H-NMR (200 MHz/CDCl$_3$)

δ (ppm)=0.90 [t, 6H], 1.2~1.8 [m, 24H], 3.93 [t, 4H], 6.6~6.8 [m, 4H], 7.74 [d, 2H]

MS(APCI(+)):M$^+$ 662

Synthetic Example 3

Synthesis of 4,4'-dibromo-2,2'-di-iodo-5,5'-dioctyloxy-1,1'-biphenyl

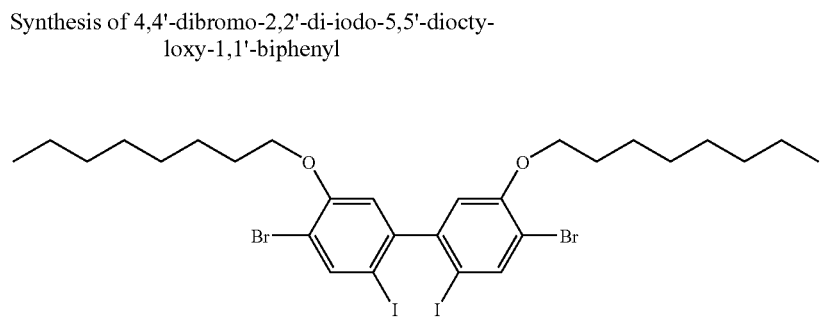

The above 2,2'-di-iodo-5,5'-dioctyloxy-1,1'-biphenyl 37 g was charged into 1L flask under nitrogen atmosphere, and trimethyl phosphate 800 ml was added and dissolved. Iodine 10.6 g was further added, trimethyl phosphate 70 ml of bromine 19 g was added dropwise. After stirring for 4 hours, trimethyl phosphate 35 ml of bromine 9.5 g was added dropwise. Then, it was stirred overnight. The reaction liquid was charged into water and extracted with chloroform, and washed with sodium-thiosulfate aqueous solution and saturated NaCl aqueous solution. After being dried with sodium sulfate, the solvent was distilled off, and 46 g of crude product was obtained. By purification using silica gel chromatography (cyclohexane:toluene=20:1), 4,4'-dibromo-2,2'-di-iodo-5,5'-dioctyloxy-1,1'-biphenyl 20.5 g was obtained.

$^1$H-NMR (200 MHz/CDCl$_3$):

δ (ppm)=0.88 [t, 6H], 1.2~1.9 [m, 24H], 3.99 [m, 4H], 6.70 [s, 2H], 8.03 [s, 2H]

MS(APCI(+)):M$^+$ 820

Synthetic Example 4

Synthesis of Compound A

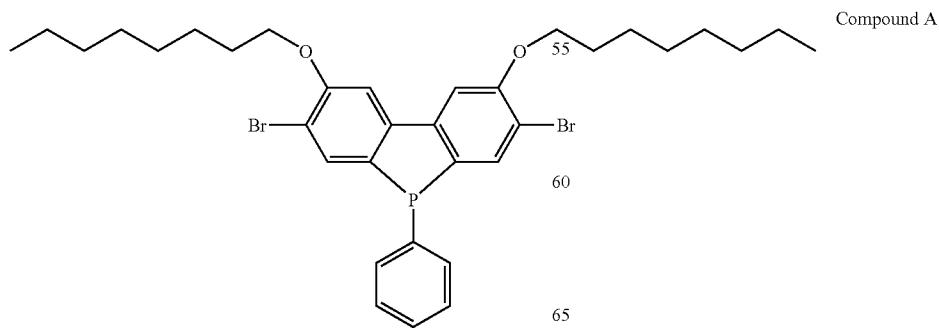

Compound A

The above 4,4'-dibromo-2,2'-di-iodo-5,5'-dioctyloxy-1,1'-biphenyl 1.00 g (appearance mole number 1.22 mmols) was put in a 100 ml three-necked flask which was flame dried and argon gas substituted, and dissolved in dehydrated diethyl ether 10 ml. This solution was cooled to −90° C. by methanol/liquid nitrogen, and n-BuLi 1.7 ml (1.6M n-hexane solution, 2.7 mmol) was added dropwise. After keeping the temperature for 1 hour, diethyl-ether solution (5 ml) of dichlorophenyl phosphine (0.22 g, 1.22 mmol) was added dropwise. After having temperature raised to a room temperature and stirring for 15 hours, it was cooled at 0° C. and 5% $NaHCO_3$ aqueous solution was added dropwise. The aqueous phase was extracted with toluene, the organic layer was collected, and washed with water and then saturated NaCl aqueous solution. The solvent was distilled off and 1.11 g of crude product was obtained. By purification using Silica gel column chromatography (eluent hexane:ethylacetate=100:1 (0.1% triethylamine)), and Compound A was obtained in 0.52 g (purity 96.1% and yield 68.5%).

$^1$H-NMR ($CDCl_3$, 300 MHz):

δ 7.77 (d, 2H), 7.31-7.13 (m, 7H), 4.198t, 4H), 1.96-1.87 (m, 4H), 1.69-1.52 (m, 4H), and 1.35-1.26 (m, 16H) and 0.90 (t, 6H)

Synthetic Example 5

Synthesis of Compound B

The above 4,4'-dibromo-2,2'-di-iodo-5,5'-dioctyloxy-1,1'-biphenyl 5.00 g (apparent mole number 6.1 mmols) was put in a 300 ml three-necked flask which was flame dried and argon gas substituted, and dissolved in dehydrated diethyl ether 50 ml. This solution was cooled to −90° C. by methanol/liquid nitrogen, and n-BuLi 8.4 ml (1.6M n-hexane solution, 13.4 mmol) was added dropwise. After keeping the temperature for 1 hour, sulfur 0.20 g (6.1 mmol) was added. After having the temperature raised to a room temperature, and stirring for 3.5 hours, sulfur 2.00 g (61 mmol) was added and stirred further 4 hours. Then, it was cooled at 0° C. and 15 ml of 1N hydrochloric acid was added dropwise. The aqueous phase was extracted with diethylehter, the organic layer was collected, and washed with water and then saturated NaCl aqueous solution. After being dried with sodium sulfate, the solvent was distilled off and 6.26 g of crude product was obtained. By purification using Silica gel column chromatography (eluent hexane:ethylacetate=20:1), and Compound B was obtained in 0.91 g (p. 87.3%, y.20.7%).

$^1$H-NMR ($CDCl_3$, 300 MHz):

δ 7.69 (s, 2H), 7.08 (s, 2H), 4.09 (t, 4H), 1.92-1.81 (m, 4H), 1.58-1.26 (m, 20H), 0.88 (t, 6H)

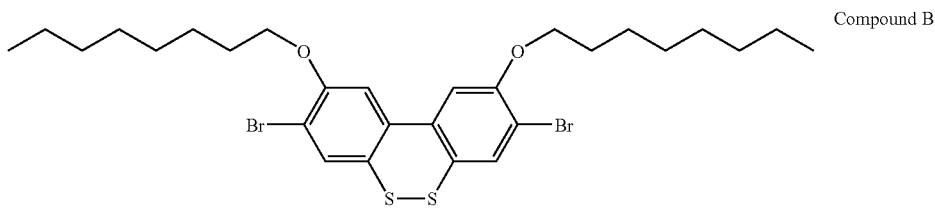

Compound B

Synthetic Example 6

Synthesis of Compound C

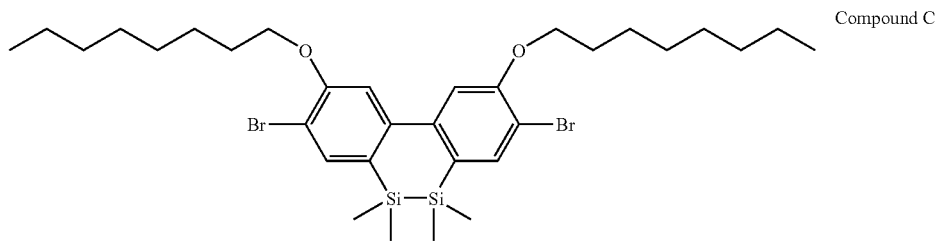

Compound C

The above 4,4'-dibromo-2,2'-di-iodo-5,5'-dioctyloxy-1,1'-biphenyl 5.0 g was charged into a 100 ml flask under nitrogen atmosphere, and tetrahydrofuran 50 ml was added to dissolve it. It was cooled at 90° C. and 8.4 ml of N-Butyl Lithium/

1.6M-hexane solution was added dropwise. After 1.5 hours stirring, tetrahydrofuran solution 61 g of magnesium-bromide 3.38 g was added, and raised the temperature to a room temperature, and further stirred for 1.5 hours. It was cooled to −90° C. again, and 1,2-dichlorotetramethyl disilane 1.60 g was added. Then the temperature was raised and reacted for 8.5 hours with refluxing.

After having distilled off the solvent, toluene 100 ml was charged and stirred, and then insoluble matters were filtrated. The solvent was distilled off again and a crude product was obtained. The crude product was purified by silica gel chromatography (eluent hexane:triethylamine toluene=800:5), and 0.24 g of Compound C was obtained.

$^1$H-NMR (300 MHz/CDCl$_3$):

δ (ppm)=0.20 [s, 12H], 0.89 [t, 6H], 1.1~1.6 [m, 20H], 1.89 [m, 4H], 4.08 [t, 4H], 6.92 [s, 2H], 7.57 [s, 2H]

Synthetic Example 7

Synthesis of Compound D into a three-necked flask under an inert atmosphere. Using a dropping funnel, the above 3-(3,7-dimethyloctyloxy)-bromobenzene 90 g was added dropwise for 50 minutes. After the dropwise adding, dried tetrahydrofuran 200 ml was added and heat-stirring was carried out for 2 hours with refluxing to prepare a Grignard reagent. After the heating, it was left standing to cool to a room temperature. Trimethyl borate 38 g and dried tetrahydrofuran 300 ml were charged into another three-necked flask, and the flask was cooled by a dry ice-acetone bath. Using a dropping funnel, the above Grignard reagent solution was added dropwise for 35 minutes. After the dropwise adding the reaction liquid was heated to a room temperature. After having added the reaction liquid to a dilute sulfuric acid (sulfuric acid 12 ml/water 360 ml) and stirring, it was divided into two portions, and each of them was extracted with 150 ml and 100 ml of ethyl acetate. The organic layers were collected together and divided into three portions, and each of them was washed with 100 ml of water. The organic layers after washing were collected together and the

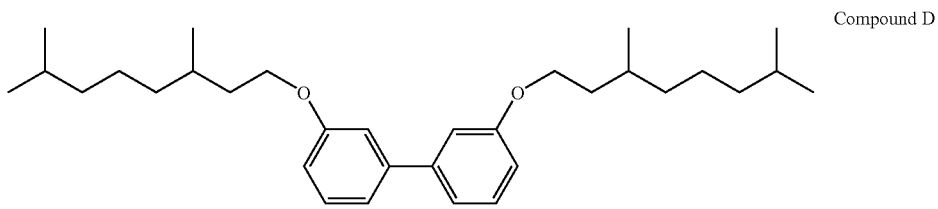

Compound D

In an inert atmosphere, 3-bromophenol 90 g was dissolved in ethanol 600 ml. 39 g of potassium hydroxide was added further, and dissolved at 70° C. 1-bromo-3,7-dimethyloctane 126 g was added dropwise from a dropping funnel for 15 minutes. After the dropwise adding, the temperature was raised to 84° C., and stirring with heating was carried out for about 22 hours.

After the heating, it was standing to cool to a room temperature. The reaction liquid was divided into two portions, each of which was added into 500 ml of water, and ethanol was distilled off with using evaporator. After distilling off the ethanol, the residual solutions were collected together and into three portions. To each of the portions, 300 ml of ethyl acetate was added and partitioned, respectively, and the organic layer was washed with 200 ml of water twice. After having collected the organic layers and distilling off the solvent using an evaporator, drying was carried out at 90° C. for 5 hours under reduced pressure using a rotary pump. About 150 g of 3-(3,7-dimethyloctyloxy)-bromobenzene was obtained as an oily product. Dried tetrahydrofuran 100 ml, magnesium 7.5 g and small quantity of iodine were charged solvent was distilled off using an evaporator. A suspension of the solid content was produced by adding 100 ml of hexane and filtrated. Further, it washed with 100 ml of hexane. White solid of 3-(3,7-dimethyloctyloxy)-phenyl boric acid 63 g was obtained. Under an inert atmosphere, to a three-necked flask, the above 3-(3,7-dimethyloctyloxy)-bromobenzene 60 g, toluene 250 ml, water 250 ml, potassium carbonate 62 g and tetrakis (triphenylphosphine)palladium complex 1.2 g were charged. After bubbling of the solution with argon for 20 minutes to deaerate oxygen, the above 3-(3,7-dimethyloctyloxy)-phenyl boric acid 63 g was added, the temperature was raised to 90° C., and stirring with heating was carried out for 8 hours. After the heating, it was left to stand for cooling to a room temperature. After partitioning the toluene layer, coloring components were removed with silica gel chromatography. The solvent was distilled off and 98 g of Compound D was obtained as an oily product.

$^1$H-NMR (200 MHz/CDCl$_3$):

ä (ppm)=0.87 [d, 12H], 0.94 [d, 6H], 1.1~1.8 [m, 20H], 4.04 [t, 4H], 6.88 [d, 2H], 7.1~7.3 [m, 4H], 7.32 [t, 2H]

Synthetic Example 8

Synthesis of Compound E

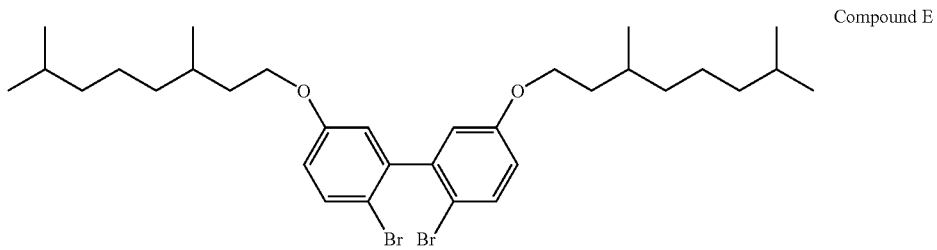

Compound E

The above compound D 20 g was dissolved in dried N,N-dimethylformamide 400 ml. A solution of N-bromosuccinimide 15.5 g/N,N-dimethylformamide 300 ml was added dropwise for 90 minutes with ice cooling. After the dropwise adding, the ice bath was removed and stirred overnight. After distilling off the solvent, it was dissolved in toluene 200 ml, and washed with 200 ml of water 3 times, and the solvent was distilled off. 26 g of oily product was obtained. From the measurement result of a LC-MS spectrum, isomers having different bromo substituted positions were observed, and the purity of Compound E was about 65% (LC area percentage).

$^1$H-NMR (200 MHz/CDCl$_3$):

ä (ppm)=0.86[d, 12H], 0.93[d, 6H], 1.1~1.8[m, 20H], 3.97 [t, 4H], 6.79[d, 2H], 6.82[d, 2H], 7.52[d, 2H]

MS(APCI (+)):M$^+$ 624

Synthetic Example 9

Synthesis of Compound F this solution, n-butyllithium 11 ml (17.6 mmol, 1.6M hexane solution) was added dropwise, and stirred for 3.5 hours. This solution was added dropwise to an ether solution 500 ml of tetrachlorosilane 25.8 g (152 mmol) cooled at −78° C. After stirring for 1 hour, the temperature was raised to a room temperature, and it was stirred for 15 hours. The reaction liquid was filtered under argon atmosphere, and the filtrate was condensed to give a crude product 4.52 g. The resultant crude product was put into a 500 ml three-necked flask whose inside was replaced with argon gas, and dissolved in 90 ml dehydrated ether, and cooled to −78° C. Phenyl lithium 23 ml (24 mmol, 1.06M cyclopentane/ether solution) was added dropwise to this solution. After stirring for 20 minutes, it was raised to a room temperature and stirred for 4 hours. Water was added and partitioned and the aqueous layer was extracted with diethyl ether. The organic layers were collected together and washed with saturated sodium hydrogencarbonate aqueous solution and saturated NaCl aqueous solution. After drying with sodium hydrogensulfate, the solvent was distilled off, and 6.66 g of a crude product of Compound F was obtained.

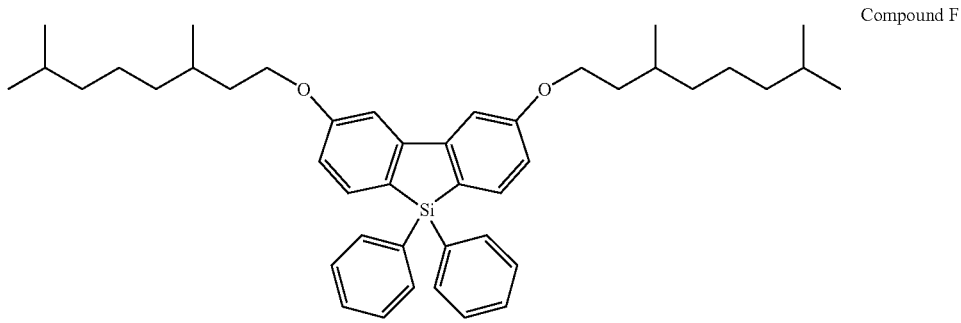

Compound F

In a 200 ml four-necked flask whose inside atmosphere was replaced with argon, Compound E 5.00 g(8.0 mmol) was dissolved in 80 ml dehydrated ether, and cooled to −78° C. To ä 0.86 (d, 12H), 0.97 (d, 6H), 1.16~1.90 (m, 20H), 4.09 (br, 4H), 6.84~6.88 (m, 2H), 7.29~7.66 (m, 28H)

MS(APCI(+)):M$^+$ 647.4

Synthetic Example 10

Synthesis of Compound G

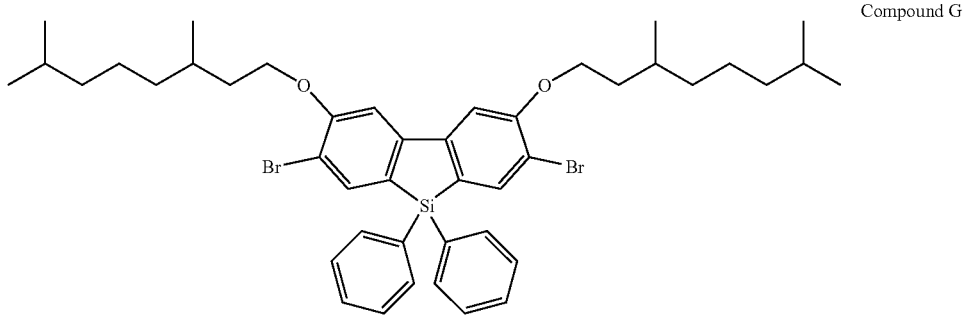

Compound G

In a 300 ml three-necked flask whose inside atmosphere was replaced with argon, Compound F 5.00 g (purity 85.1%, 6.6 mmol) was put in and dissolved in dehydrated DMF 65 ml. N-bromosuccinimide 2.45 g (13.8 mmol) was charged to this solution. After stirring at a room temperature for 5 hours, it was extracted with hexane (80 ml×5) in a glove box. The solvent was distilled off, and 14.02 g of a crude product (LC area percentage 19.9% including DMF) was obtained. After separation with reversed-phase silica gel column chromatography (acetonitrile:toluene=20:1), fractions were extracted with hexane (in order to remove a minute amount of acetic acid in acetonitrile), and washed by 5% sodium-hydrogencarbonate aqueous solution and saturated NaCl aqueous solution. After drying with sodium sulfate, the solvent was distilled off, and 0.30 g (LC area percentage 58%, yield 3.3%) of Compound G was obtained.

$^1$H-NMR (300 MHz/acetone-d6):

δ 0.86 (d, 12H), 0.99 (d, 6H), 1.17~1.95 (m, 20H), 4.31 (br, 4H), 7.37~7.50 (m, 2H), 7.68~7.71 (m, 28H), 7.81 (s, 2H), 8.00 (s, 2H)

MS(APCI(+)):M$^+$ 804.9

Synthetic Example 11

Synthesis of Compound H

Compound F 3.91 g (purity 85.1%, 5.1 mmol) was put in a 200 ml three necked flask whose inside was replaced with argon gas, and dissolved in dehydrated DMF 50 ml. NCS 1.47 g (10.8 mmol) was charged into this solution. NCS was added, with pursuing the reaction by LC. (total 2.62 g). After stirring for 60 hours at a room temperature, it was extracted with hexane (100 ml×5) in a glove box. The solvent was distilled off, and 12.73 g (LC area percentage 34.1%, including DMF) of a crude product was obtained. After separation with reversed-phase silica gel column chromatography (acetonitrile:toluene=20:1), the fractions were extracted with hexane, and washed with 5% sodium-hydrogencarbonate aqueous solution and saturated NaCl aqueous solution (in order to remove the minute amount of acetic acid in acetonitrile). After drying with sodium sulfate, the solvent was distilled off, and 0.18 g (82.5% of LC area percentage, 3.6% of yield) Compound H was obtained.

$^1$H-NMR (300 MHz/acetone-d6):

δ 0.87 (d, 12H), 0.99 (d, 6H), 1.10~1.94 (m, 20H), 4.28 (br, 4H), 7.30~7.71 (m, 10H), 7.83 (br, 4H)

MS(APCI(+)):M$^+$ 715.3

Example 1

Condensation polymerization of Compound A

<Synthesis of Polymer 1>

Compound A 0.59 g, N,N'-bis(4-bromophenyl)-N,N'-bis(4-n-butyl phenyl)-1,4-phenylenediamine 0.26 g, 2,2'-bipyridyl 0.48 g were charged into a reaction vessel, and the atmosphere of the reaction system was replaced with nitrogen gas. To this, 35 ml of tetrahydrofuran (dehydrated solvent)

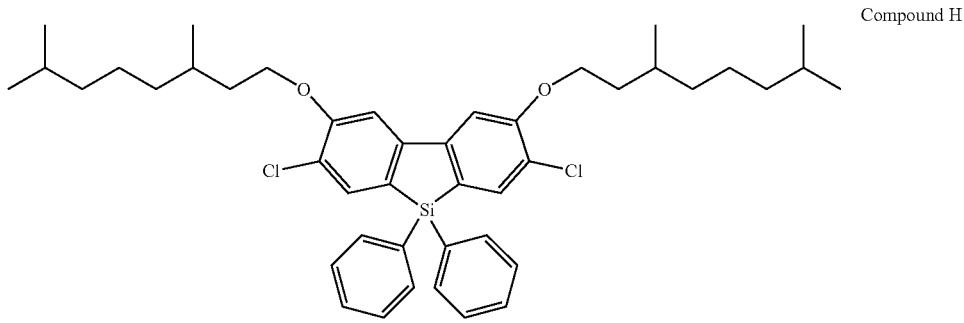

Compound H which was deaerated beforehand by bubbling with argon gas was added. Next, bis(1,5-cyclo octadiene) nickel (0) 0.85 g was added to this mixed solution, and reacted at 60° C. for 3 hours. The reaction was performed in nitrogen-gas atmosphere. After the reaction, this solution was cooled and then poured into a mixed solution of 25% aqueous-ammonia 10 ml/methanol 120 ml/ion-exchanged water 50 ml, and stirred for about 1 hour. Next, resulting precipitate was collected by filtration. The precipitate was washed with ethanol, and dried at a reduced pressure for 2 hours. Next, this precipitate was dissolved in toluene 30 mL, after the addition of 1N hydrochloric-acid 30 mL, it was stirred for 1 hour. The aqueous layer was removed, and 4% aqueous-ammonia 30 mL was added to an organic layer, and after stirring for 1 hour, the aqueous layer was removed. The organic layer was added dropwise to methanol 200 mL, and stirred for 1 hour. The deposited precipitate was filtered and dried for 2 hours at a reduced pressure, and then dissolved in toluene 30 mL. Then, it was purified by passing through alumina column (20 g of alumina). The collected toluene solution was added dropwise to methanol 250 mL, stirred for 1 hour, and deposited precipitate was filtered and dried for 2 hours at a reduced pressure. The yield of the resulting polymer was 0.06 g. This polymer is referred to as Polymer 1.

The polystyrene reduced number average molecular weight of Polymer 1 was $5.0 \times 10^2$, and the polystyrene reduced weight average molecular weight was $6.2 \times 10^3$.

Example 2

Condensation polymerization of Compound B

<Synthesis of Polymer 2>

Compound B 0.35 g, N,N'-bis(4-bromophenyl)-N,N'-bis(4-n-butyl phenyl)-1,4-phenylenediamine 0.16 g, 2,2'-bipyridyl 0.37 g were charged into a reaction vessel, and the atmosphere of the reaction system was replaced with nitrogen gas. To this, 28 ml of tetrahydrofuran (dehydrated solvent) which was deaerated beforehand by bubbling with argon gas was added. Next, bis(1,5-cyclo octadiene) nickel (0) 0.70 g was added to this mixed solution, and reacted at 60° C. for 3 hours. The reaction was performed in nitrogen-gas atmosphere. After the reaction, this solution was cooled and then poured into a mixed solution of 25% aqueous-ammonia 10 ml/methanol 120 ml/ion-exchanged water 50 ml, and stirred for about 1 hour. Next, resulting precipitate was collected by filtration. The precipitate was washed with ethanol, and dried at a reduced pressure for 2 hours. Next, this precipitate was dissolved in toluene 30 mL, after the addition of 1N hydrochloric-acid 30 mL, it was stirred for 1 hour. The aqueous layer was removed, and 4% aqueous-ammonia 30 mL was added to an organic layer, and after stirring for 1 hour, the aqueous layer was removed. The organic layer was added dropwise to methanol 200 mL, and stirred for 1 hour. The deposited precipitate was filtered and dried for 2 hours at a reduced pressure, and then dissolved in toluene 30 mL. Then, it was purified by passing through alumina column (20 g of alumina). The collected toluene solution was added dropwise to methanol 250 mL, stirred for 1 hour, and deposited precipitate was filtered and dried for 2 hours at a reduced pressure. The yield of the resulting polymer was 0.13 g. This polymer is referred to as Polymer 2.

The polystyrene reduced number average molecular weight of Polymer 2 was $6.2 \times 10^3$, and the polystyrene reduced weight average molecular weight was $5.1 \times 10^4$.

Example 3

Condensation polymerization of Compound C

Synthesis of Polymer 3

Compound C 0.30 g, N,N'-bis(4-bromophenyl)-N,N'-bis(4-n-butyl phenyl)-1,4-phenylenediamine 0.13 g, 2,2'-bipyridyl 0.30 g were charged into a reaction vessel, and the atmosphere of the reaction system was replaced with nitrogen gas. To this, 20 ml of tetrahydrofuran (dehydrated solvent) which was deaerated beforehand by bubbling with argon gas was added. Next, bis(1,5-cyclo octadiene) nickel (0) 0.52 g was added to this mixed solution, and reacted at 60° C. for 3 hours. The reaction was performed in nitrogen-gas atmosphere. After the reaction, this solution was cooled and then poured into a mixed solution of 25% aqueous-ammonia 10 ml/methanol 120 ml/ion-exchanged water 50 ml, and stirred for about 1 hour. Next, resulting precipitate was collected by filtration. The precipitate was washed with ethanol, and dried at a reduced pressure for 2 hours. Next, this precipitate was dissolved in toluene 30 mL, after the addition of 1N hydrochloric-acid 30 mL, it was stirred for 1 hour. The aqueous layer was removed, and 4% aqueous-ammonia 30 mL was added to an organic layer, and after stirring for 1 hour, the aqueous layer was removed. The organic layer was added dropwise to methanol 200 mL, and stirred for 1 hour. The deposited precipitate was filtered and dried for 2 hours at a reduced pressure, and then dissolved in toluene 30 mL. Then, it was purified by passing through alumina column (20 g of alumina). The collected toluene solution was added dropwise to methanol 250 mL, stirred for 1 hour, and deposited precipitate was filtered and dried for 2 hours at a reduced pressure. The yield of the resulting polymer was 0.11 g. This polymer is referred to as Polymer 3.

The polystyrene reduced number average molecular weight of Polymer 3 was $1.4 \times 10^3$, and the polystyrene reduced weight average molecular weight was $4.9 \times 10^4$.

Example 4

Condensation polymerization of Compound G

<Synthesis of Polymer 4>

Compound G 0.20 g, N,N'-bis(4-bromophenyl)-N,N'-bis(4-n-butyl phenyl)-1,4-phenylenediamine 0.07, 2,2'-bipyridyl 0.17 g were charged into a reaction vessel, and the atmosphere of the reaction system was replaced with nitrogen gas. To this, 20 ml of tetrahydrofuran (dehydrated solvent) which was deaerated beforehand by bubbling with argon gas was added. Next, bis(1,5-cyclo octadiene) nickel (0) 0.3 g was added to this mixed solution, and stirred at a room temperature for 10 minutes, and reacted at 60° C. for 3 hours. The reaction was performed in nitrogen-gas atmosphere. After the reaction, this solution was cooled and then poured into a mixed solution of methanol 120 ml/ion-exchanged water 200 ml, and stirred for about 1 hour. Next, resulting precipitate was collected by filtration. The precipitate was dried and dissolved in chloroform. The solution was filtered to remove insoluble matters, and the chloroform was distilled off to give a solid product. This solid product was washed with methanol and dried at a reduced pressure to yield a polymer 0.08 g. This polymer is referred to as Polymer 4.

The polystyrene reduced number average molecular weight of Polymer 4 was 1.5×10³, and the polystyrene reduced weight average molecular weight was 5.0×10³.

Example 5

Polymerization of Compound H

<Synthesis of Polymer 5>

Compound H 0.21 g, N,N'-bis(4-bromophenyl)-N,N'-bis (4-n-butyl phenyl)-1,4-phenylenediamine 0.10, 2,2'-bipyridyl 0.27 g were charged into a reaction vessel, and the atmosphere of the reaction system was replaced with nitrogen gas. To this, 20 ml of tetrahydrofuran (dehydrated solvent) which was deaerated beforehand by bubbling with argon gas was added. Next, bis(1,5-cyclo octadiene) nickel (0) 0.5 g was added to this mixed solution, and stirred at a room temperature for 10 minutes, and reacted at 60° C. for 3 hours. The reaction was performed in nitrogen-gas atmosphere. After the reaction, this solution was cooled and then poured into a mixed solution of methanol 100 ml/ion-exchanged water 200 ml, and stirred for about 1 hour. Next, resulting precipitate was collected by filtration. The precipitate was dried and dissolved in toluene. The solution was filtered to remove insoluble matters, and the toluene was distilled off to give a solid product. This solid product was washed with ethanol and dried at a reduced pressure to yield a polymer 0.09 g. This polymer is referred to as Polymer 5.

The polystyrene reduced number average molecular weight of Polymer 5 was 1.6×10³, and the polystyrene reduced weight average molecular weight was 5.4×10³.

Example 6

<Fluorescence Characteristics>

Each of the 2wt % chloroform solutions of Polymers 1 to 5 were spin coated respectively on quartz, and thin films of polymeric fluorescent substance were produced. The fluorescence spectrum of these thin films were measured using a spectrophotometer (Hitachi 850). All of them have strong fluorescence and they respectively showed fluorescence peak wavelengthes shown in Table 1.

TABLE 1

| Polymer | Fluorescence peak wavelength (nm) |
|---------|-----------------------------------|
| Polymer 1 | 516 |
| Polymer 2 | 468 |
| Polymer 3 | 458 |
| Polymer 4 | 466 |
| Polymer 5 | 458 |

Calculation Examples

Calculation examples of bond-distance ratio are shown below. The calculation was performed using Gaussian 98 (b3lyp/6-31 g*).

Calculation Example 1

Comparison of a Monomer with a Trimer

The bond-distance ratio of a monomer having hydrogen atoms at the bonding positions in polymerization was compared with that of the trimer.

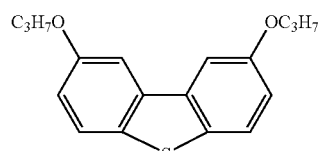

Calculation compound 1

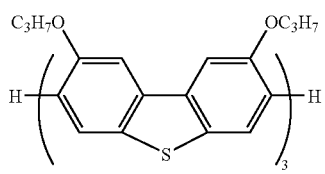

Calculation compound 2

| Calculation compound | Bond-distance ratio |
|----------------------|---------------------|
| Calculation compound 1 | 1.254 |
| Calculation compound 2 (Center) | 1.256 |
| Calculation compound 2 (Terminal) | 1.254 |

The difference of the bond-distance ratios was small, and the bond-distance ratio of a polymer can be approximated by that of the monomer having hydrogen atoms at the bonding position in polymerization.

Calculation Example 2

Comparison of the Side Chains

The bond-distance ratios were compared between a compound having methoxy group as the alkyloxy group side chain and a compound having n-octyloxy group.

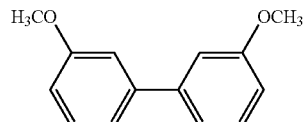

Calculation compound 3

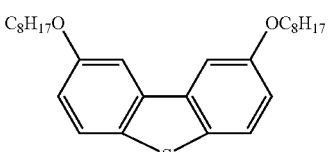

Calculation compound 4

| Calculation compound | Bond-distance ratio |
|----------------------|---------------------|
| Calculation compound 3 | 1.254 |
| Calculation compound 4 | 1.254 |

The difference of the bond-distance ratios was small, and the bond-distance ratio of a compound having n-octyloxy group can be approximated by that of the compound having methoxy group.

Calculation Example 3

Calculation of the Compounds Produced in Examples

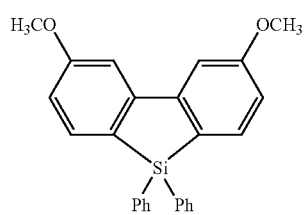

Calculation compound 5

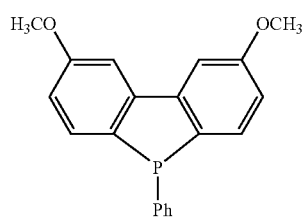

Calculation compound 6

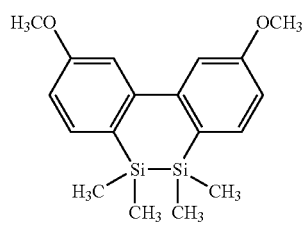

Calculation compound 7

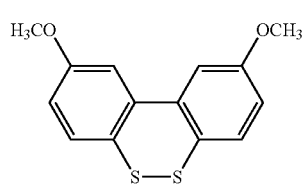

Calculation compound 8

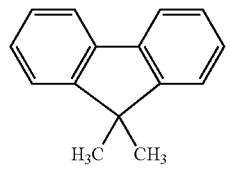

Comparative Example 1

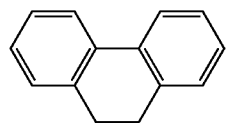

Comparative Example 2

In the formula, Ph represents a phenyl group.

| Calculation compound | Bond-distance ratio |
|---|---|
| Calculation compound 5 | 1.329 |
| Calculation compound 6 | 1.304 |

-continued

| Calculation compound | Bond-distance ratio |
|---|---|
| Calculation compound 7 | 1.338 |
| Calculation compound 8 | 1.268 |
| Comparative Example 1 | 1.085 |
| Comparative Example 2 | 1.071 |

The polymer of the present invention is a new polymer which can be used as a light-emitting material, a charge transporting material, etc.

What is claimed is:

1. A polymer having a polystyrene reduced number average molecular weights of $10^3$-$10^8$, and comprising a repeating unit represented by formula (1),

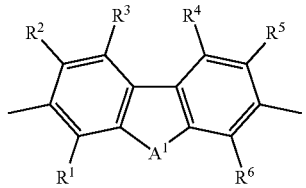

(1)

wherein, $R^1$, $R^2$, $R^3$, $R^4$, $R^5$, and $R^6$, each independently represent a hydrogen atom, a halogen atom, an alkyl group, alkenyl group, alkynyl group, alkyloxy group, alkylthio group, an alkylamino group, aryl group, aryloxy group, arylthio group, arylamino group, arylalkyl group, arylalkyloxy group, aryl alkylthio group, arylalkylamino group, substituted silyl group, acyl group, acyloxy group, imino group, amide group, arylalkenyl group, arylalkynyl group, monovalent heterocyclic group, or cyano group; $R^2$ and $R^3$ may be connected to form a ring; and $R^4$ and $R^5$ may be connected to form a ring;

$A^1$ is a divalent group represented by formula (3), (4), (5) or (6),

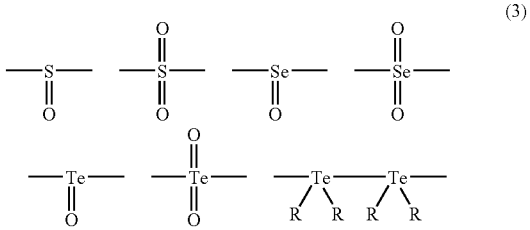

(3)

R in the above formula (3) each independently represent a hydrogen atom, a halogen atom, an alkyl group, alkyloxy group, alkylthio group, alkylamino group, aryl group, aryloxy group, arylthio group, arylamino group, arylalkyl group, arylalkyloxy group, arylalkylthio group, arylalkylamino group, substituted silyl group, acyl group, acyloxy group, imino group, amide group, arylalkenyl group, arylalkynyl group, monovalent heterocyclic group, or cyano group,

(4)

wherein, $R^7$ represents an alkyloxy group, alkylthio group, alkylamino group, aryl group, aryloxy group, arylthio group, arylamino group, arylalkyl group, arylalkyloxy group, arylalkylthio group, arylalkyl amino group, acyl group, acyloxy group, amide group, or monovalent heterocyclic group,

—S—S—   (5)

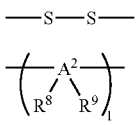
(6)

wherein, $A^2$ represents Si, Ge, or Sn; $R^8$ and $R^9$ each independently represent an alkyl group, alkyloxy group, alkylthio group, alkylamino group, aryl group, aryloxy group, arylthio group, arylamino group, arylalkyl group, arylalkyloxy group, arylalkylthio group, arylalkylamino group, acyloxy group, amide group, or monovalent heterocyclic group; l represents 2, and the polymer further comprises a repeating unit represented by formula (7) or formula (8),

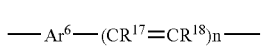
(7)

wherein, $Ar^6$ represents an arylene group or a divalent heterocyclic group; $R^{17}$ and $R^{18}$ each independently represent a hydrogen atom, an alkyl group, aryl group, monovalent heterocyclic group, or cyano group; and n represents 0 or 1,

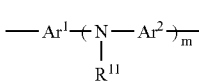
(8)

wherein, $Ar^1$ and $Ar^2$ each independently represent an arylene group or a divalent heterocyclic group; $R^{11}$ represents a group represented by an alkyl group, aryl group, monovalent heterocyclic group, and a group represented by the below formula (9) or (10); and m represents an integer of 1-4,

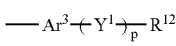
(9)

wherein, $Ar^3$ represents an arylene group or a divalent heterocyclic group; $R^{12}$ represents a hydrogen atom, an alkyl group, aryl group, monovalent heterocyclic group, or a group represented by the below formula (10); Y1 represents —$CR^{13}$=$CR^{14}$—, or —C≡C—; $R^{13}$ and $R^{14}$ each independently represent a hydrogen atom, an alkyl group, aryl group, monovalent heterocyclic group, or cyano group; and p represents an integer of 0-2,

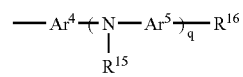
(10)

wherein, $Ar^4$ and $Ar^5$ each independently represent an arylene group or a divalent heterocyclic group; $R^{15}$ represents an alkyl group, aryl group, or monovalent heterocyclic group; $R^{16}$ represents a hydrogen atom, an alkyl group, aryl group, or monovalent heterocyclic group;

and q represents an integer of 1-4.

2. A polymer according to claim 1, wherein $A^1$ is a divalent group represented by the above formula (4).

3. A polymer according to claim 1, wherein $A^1$ is a divalent group represented by the above formula (5).

4. A polymer according to claim 1, wherein $A^1$ is a divalent group represented by formula (6), in which $A^2$ is Si, and l is 2.

5. A polymer according to claim 1, wherein $R^2$ and $R^5$ each independently represent an alkyloxy group, alkylthio group, alkylamino group, aryloxy group, arylthio group, arylamino group, arylalkyloxy group, arylalkylthio group, or arylalkylamino group.

6. A polymer according to claim 5, wherein $R^2$ and $R^5$ each independently represent alkyloxy group, aryloxy group, or arylalkyloxy group.

7. A process for producing a polymer according to claims 1, 2, 3, 4, 5, or 6, wherein a condensation polymerization is carried out using a compound represented by the below formula (11),

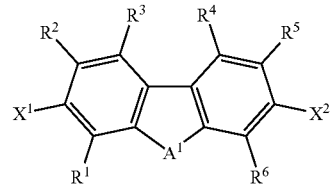
(11)

wherein, $R^1$, $R^2$, $R^3$, $R^4$, $R^5$, $R^6$, and $A^1$ respectively represent the same groups as those in formula (1); $x^1$ and $x^2$ each independently represent a substituent capable of condensation polymerization.

8. A process for producing a polymer according to claim 7, wherein $X^1$ and $X^2$ each independently represent a halogen atom, alkyl sulfonate group, aryl sulfonate group or arylalkyl sulfonate group and wherein the condensation polymerization is carried out using a palladium catalyst or a nickel catalyst.

9. A polymer electronic device including a polymer according to claims 1, 2, 3, 4, 5, or 6.

10. A polymeric fluorescent substance consisting of a polymer according to claims 1, 2, 3, 4, 5, or 6.

11. A polymer light-emitting device having a light emitting layer between the electrodes consisting of an anode and a cathode, wherein said light-emitting layer contains the polymer according to claims 1, 2, 3, 4, 5, or 6.

12. A flat light source comprising a polymer light-emitting device according to claim 11.

13. A segment display apparatus comprising a polymer light-emitting device according to claim 11.

14. A dot-matrix display apparatus comprising a polymer light-emitting device according to claim 11.

15. A liquid crystal display comprising a polymer light-emitting device according to claim 11 as a back light.

16. A compound represented by formula (11),

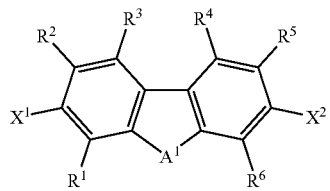

wherein, $R^1, R^2, R^3, R^4, R^5, R^6$, each independently represent a hydrogen atom, a halogen atom, an alkyl group, alkenyl group, alkynyl group, alkyloxy group, alkylthio group, an alkylamino group, aryl group, aryloxy group, arylthio group, arylamino group, arylalkyl group, arylalkyloxy group, aryl alkylthio group, arylalkylamino group, substituted silyl group, acyl group, acyloxy group, imino group, amide group, arylalkenyl group, arylalkynyl group, monovalent heterocyclic group, or cyano group; $R^2$ and $R^3$ may be connected to form a ring; and $R^4$ and $R^5$ may be connected to form a ring;

$A^1$ is a divalent group represented by formula (3), (4), (5) or (6),

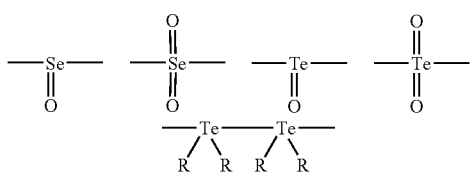

R in the above formula (3) each independently represent a hydrogen atom, a halogen atom, an alkyl group, alkyloxy group, alkylthio group, alkylamino group, aryl group, aryloxy group, arylthio group, arylamino group, arylalkyl group, arylalkyloxy group, arylalkylthio group, arylalkylamino group, substituted silyl group, acyl group, acyloxy group, imino group, amide group, arylalkenyl group, arylalkynyl group, monovalent heterocyclic group, or cyano group,

wherein, $R^7$ represents an alkyloxy group, alkylthio group, alkylamino group, aryl group, aryloxy group, arylthio group, arylamino group, arylalkyl group, arylalkyloxy group, arylalkylthio group, arylalkyl amino group, acyl group, acyloxy group, amide group, or monovalent heterocyclic group,

wherein, $A^2$ represents Si, Ge, or Sn; $R^8$ and $R^9$ each independently represent an alkyl group, alkyloxy group, alkylthio group, alkylamino group, aryl group, aryloxy group, arylthio group, arylamino group, arylalkyl group, arylalkyloxy group, arylalkylthio group, arylalkylamino group, acyloxy group, amide group, or monovalent heterocyclic group; 1 represents 2; and wherein $X^1$ and $X^2$ each independently represent a substituent capable of condensation polymerization.

17. A compound according to claim 16, wherein $A^1$ is a divalent group represented by formula (4).

18. A compound according to claim 16, wherein $A^1$ is a divalent group represented by formula (5),

19. A compound according to claim 16, wherein $A^1$ is a divalent group represented by formula (6),

wherein $R^8$ and $R^9$ each independently represent an alkyl group, alkyloxy group, alkylthio group, alkylamino group, aryl group, aryloxy group, arylthio group, arylamino group, arylalkyl group, arylalkyloxy group, arylalkylthio group, arylalkylamino group, acyloxy group, amide group, or monovalent heterocyclic group, $A^2$ is Si, and 1 is 2.

20. A compound according to claim 16, wherein $R^2$ and $R^5$ each independently represent an alkyloxy group, alkylthio group, alkylamino group, aryloxy group, arylthio group, arylamino group, arylalkyloxy group, arylalkylthio group, or arylalkylamino group.

21. A compound according to claim 20, wherein $R^2$ $R^5$ and each independently represent an alkyloxy group, aryloxy group, or arylalkyloxy group.

22. A compound according to claim 16, wherein $X^1$ and $X^2$ each independently represent a halogen atom, alkyl sulfonate group, aryl sulfonate group, or arylalkyl sulfonate group.

23. A compound according to claim 16, wherein $X^1$ and $X^2$ each independently represent a halogen atom.

24. A process for producing a compound according to any one of claims 17 or 20 to 23 wherein two iodine atoms in the compound represented by the below formula (13) are selectively metalated, and then reacted with a dihalogenated phosphorous compound represented by the below formula (14),

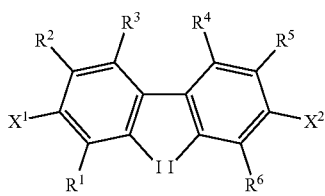

(13)

wherein, $R^1$, $R^2$, $R^3$, $R^4$, $R^5$ and $R^6$ each independently represent a hydrogen atom, a halogen atom, an alkyl group, alkenyl group, alkynyl group, alkyloxy group, alkylthio group, an alkylamino group, aryl group, aryloxy group, arylthio group, arylamino group, arylalkyl group, arylalkyloxy group, aryl alkylthio group, arylalkylamino group, substituted silyl group, acyl group, acyloxy group, imino group, amide group, arylalkenyl group, arylalkynyl group, monovalent heterocyclic group, or cyano group; $R^2$ and $R^3$ may be connected to form a ring; and $R^4$ and $R^5$ may be connected to form a ring, and $X^1$ and $X^2$ respectively each independently represent a substituent capable of condensation polymerization,

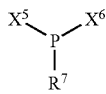

(14)

wherein, $R^7$ represents an alkyl group, alkyloxy group, alkylthio group, alkylamino group, aryl group, aryloxy group, arylthio group, arylamino group, arylalkyl group, arylalkyloxy group, arylalkylthio group, arylalkyl amino group, acyl group, acyloxy group, amide group, or monovalent heterocyclic group; $X^5$ and $X^6$ each independently represent a chlorine atom, bromine atom, or iodine atom.

25. A process for producing a compound according to any one of claims 18 or 20 to 23, wherein two iodine atoms of the compound represented by formula (13),

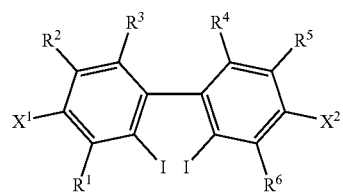

(13)

are selectively metalated, and then reacted with sulfur, wherein in formula (13), $R^1$, $R^2$, $R^3$, $R^4$, $R^5$, and $R^6$, each independently represent a hydrogen atom, a halogen atom, an alkyl group, alkenyl group, alkynyl group, alkyloxy group, alkylthio group, an alkylamino group, aryl group, aryloxy group, arylthio group, arylamino group, arylalkyl group, arylalkyloxy group, aryl alkylthio group, arylalkylamino group, substituted silyl group, acyl group, acyloxy group, imino group, amide group, arylalkenyl group, arylalkynyl group, monovalent heterocyclic group, or cyano group; $R^2$ and $R^3$ may be connected to form a ring; and $R^4$ and $R^5$ may be connected to form a ring; $X^{1\ and\ X2}$ each independently represent a substituent capable of condensation polymerization.

26. A process for producing a disilyl compound according to any one of claims 19-23 wherein two iodine atoms in the compound represented by the above formula (13) are selectively metalated, and then reacted with a dihalogenated disilyl compound represented by the below formula (22),

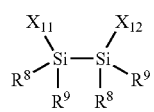

(22)

wherein, $R^8$ and $R^9$ represent respectively represent the same groups as those in formula (6); $X^{11}$ and $X^{12}$ each independently represent a chlorine atom, bromine atom, or iodine atom.

* * * * *